United States Patent
Rao et al.

(10) Patent No.: US 7,786,142 B2
(45) Date of Patent: Aug. 31, 2010

(54) HETEROCYCLIC COMPOUNDS AS PSTAT3/IL-6 INHIBITORS

(75) Inventors: Siripragada Mahender Rao, Chennai (IN); Akella Satya Surya Visweswara Srinvas, Chennai (IN); Shikha Rani, Chennai (IN); Gaddam Om Reddy, Chennai (IN); Sriram Rajagopal, Chennai (IN); Uma Ramachandran, Chennai (IN); Duddu Savaraiah Sharada, Chennai (IN); Rajagopalan Nirmala, Chennai (IN); Velaiah Sivasudar, Chennai (IN); Lakshmanan Manikandan, Chennai (IN); Ramachandran Balaji, Chennai (IN)

(73) Assignee: Orchid Research Laboratories, Ltd., Chennai (IN)

( * ) Notice: Subject to any disclaimer, the term of this patent is extended or adjusted under 35 U.S.C. 154(b) by 211 days.

(21) Appl. No.: 11/546,299

(22) Filed: Oct. 12, 2006

(65) Prior Publication Data

US 2007/0111998 A1 May 17, 2007

(30) Foreign Application Priority Data

Oct. 13, 2005 (IN) .................. 1471/CHE/2005

(51) Int. Cl.
*A61K 31/4468* (2006.01)
*A61K 31/403* (2006.01)
*C07D 405/14* (2006.01)
*C07D 209/88* (2006.01)

(52) U.S. Cl. ............... 514/323; 514/411; 546/200; 548/444

(58) Field of Classification Search .......... 514/411; 548/444
See application file for complete search history.

(56) References Cited

U.S. PATENT DOCUMENTS

| | | | |
|---|---|---|---|
| 4,503,067 A | 3/1985 | Wiedemann et al. | |
| 6,140,352 A | 10/2000 | Crowell et al. | |
| 6,506,901 B2 * | 1/2003 | Steffan et al. | 546/192 |
| 2002/0032222 A1 | 3/2002 | Malamas et al. | |
| 2005/0049299 A1 | 3/2005 | Aggarwal | |

FOREIGN PATENT DOCUMENTS

| | | |
|---|---|---|
| DE | 35 24 955 A1 | 1/1986 |
| EP | 0 004 920 | 8/1981 |
| WO | WO 98/07321 | 2/1998 |
| WO | WO 98/09625 A1 | 3/1998 |
| WO | WO 00/44774 | 8/2000 |
| WO | WO 01/62705 A2 | 8/2001 |
| WO | WO 02/06221 A2 | 1/2002 |
| WO | WO 02/06232 A1 | 1/2002 |
| WO | WO 02/06274 | 1/2002 |
| WO | WO 02/074298 A1 | 9/2002 |
| WO | WO 02/094770 A2 | 11/2002 |
| WO | WO 2004/002472 A1 | 1/2004 |
| WO | WO 2004/024145 A1 | 3/2004 |
| WO | WO 2004/080394 A2 | 9/2004 |
| WO | WO 2004/113296 A1 | 12/2004 |
| WO | WO 2005/058829 A1 | 6/2005 |
| WO | WO 2006/012625 A2 | 2/2006 |
| WO | WO 2006/060122 A2 | 6/2006 |

OTHER PUBLICATIONS

Vippagunta et al., Crystalline solids, 2001, Advanced Drug Delivery Reviews, 48, pp. 3 and 18.*
Wang et al., Synthesis and bioactivity of 1-(9H-carbazol-4-yloxy)-3-substituted amino-2-propanol compounds, 2001, Zhongguo Yaoke Daxube Xuebao, 32(6), p. 408.*
Rudolph et al., Synthesis of the glucuronide of Carazolol, 1988, Carbohydrate Research, 176, 155-159.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
D. Parkin et al., "Global Cancer Statistics, 2002", CA Cancer J. Clin., vol. 55, (2005) pp. 74-108.
A. Matter, "Tyrosine Kinase Inhibitors in Cancer Drug Discovery", International Symposium on Predictive Oncology and Intervention Strategies, (Feb. 2002) Section on Molecular Basis of Oncogenesis.
A. Bharti et al., "Curcumin (Diferuloylmethane) Inhibits Constitutive and IL-6-Inducible STAT3 Phosphorylation in Human Multiple Myeloma Cells", The Journal of Immunology, vol. 171, (2003) pp. 3863-3871.

(Continued)

*Primary Examiner*—Kamal A Saeed
*Assistant Examiner*—Kristin Bianchi
(74) *Attorney, Agent, or Firm*—Oliff & Berridge, PLC

(57) ABSTRACT

The present invention relates to novel heterocyclic compounds of the general formula (I), as IL-6 inhibitors, their derivatives, their analogs, their tautomeric forms, their stereoisomers, their polymorphs, their hydrates, their solvates, their pharmaceutically acceptable salts and compositions, their metabolites and prodrugs thereof. The present invention more particularly provides novel heterocyclic compounds of the general formula (I). Also included is a method for treatment of cancer, cancer cachexia and inflammatory diseases including immunological diseases, particularly those mediated by cytokines such as IL-6, through pSTAT3 inhibition, in a mammal comprising administering an effective amount of a compound of formula (I) as described above (I)

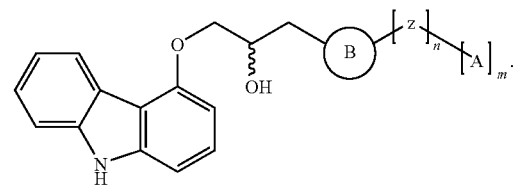

18 Claims, 4 Drawing Sheets

OTHER PUBLICATIONS

A. Verma et al., "Jak Family of Kinases in Cancer", Cancer and Metastasis Reviews, vol. 22, (2003) pp. 423-434.

I. Kerr et al., "Of JAK's, STATs, Blind Watchmakers, Jeeps and Trains", FEBS Letters, vol. 546, (2003) pp. 1-5.

R. Catlett-Falcone et al., "Constitutive Activation of Stat3 Signaling Confers Resistance to Apoptosis in Human U266 Myeloma Cells", Immunity, vol. 10, (Jan. 1999) pp. 105-115.

S. Alas et al., "Inhibition of Constitutive STAT3 Activity Sensitizes Resistant Non-Hodgkin's Lymphoma and Multiple Myeloma to Chemotherapeutic Drug-Mediated Apoptosis", Clinical Cancer Research, vol. 9, (Jan. 2003) pp. 316-326.

L. Burdelya et al., "Combination Therapy With AG-490 and Interleukin 12 Achieves Greater Antitumor Effects Than Either Agent Alone", Molecular Cancer Therapeutics, vol. 1, (Sep. 2002) pp. 893-899.

B. Klein et al., "Murine Anti-Interleukin-6 Monoclonal Antibody Therapy for a Patient With Plasma Cell Leukemia", Blood, vol. 78, No. 5, (Sep. 1, 1991) pp. 1198-1204.

Z. Y. Lu et al., "High Amounts of Circulating Interleukin (IL)-6 in the Form of Monomeric Immune Complexes During Anti-IL-6 Therapy. Towards a New Methodology for Measuring Overall Cytokine Production in Human In Vivo" (Abstract), European Journal of Immunology, vol. 22, Issue 11, (1992) pp. 2819-2824.

M. Hallek et al., "Multiple Myeloma: Increasing Evidence for a Multistep Transformation Process", Blood, vol. 91, No. 1, (Jan. 1, 1998) pp. 3-21.

P. Selvanayagam et al., "Alteration and Abnormal Expression of the c-myc Oncogene in Human Multiple Myeloma", Blood, vol. 71, No. 1, (Jan. 1988) pp. 30-35.

N. Meydan et al., "Inhibition of Acute Lymphoblastic Leukaemia by a Jak-2 Inhibitor", Nature, vol. 379, (Feb. 15, 1996) pp. 645-648.

G. Constantin et al., "Tyrphostin AG490, a Tyrosine Kinase Inhibitor, Blocks Actively Induced Experimental Autoimmune Encephalomyelitis" (Abstract), European Journal of Immunology, vol. 28, Issue 11, (1998) pp. 3523-3529.

J. Ihle et al., "Jaks and Stats in Signaling by the Cytokine Receptor Superfamily", TIG, vol. 11, No. 2, (Feb. 1995) pp. 69-74.

C. Schindler et al., "Transcriptional Responses to Polypeptide Ligands: The JAK-STAT Pathway", Annu. Rev. Biochem., vol. 64, (1995) pp. 621-651.

C. M. Horvath et al., "The State of the STATs: Recent Developments in the Study of Signal Transduction to the Nucleus", Current Opinion in Cell Biology, vol. 9, (1997) pp. 233-239.

G. Stark et al., "How Cells Respond to Interferons", Annu. Rev. Biochem., vol. 67, (1998) pp. 227-264.

J. Irie-Sasaki et al., "CD45 is a JAK Phosphatase and Negatively Regulates Cytokine Receptor Signalling", Nature, vol. 409, (Jan. 18, 2001) pp. 349-354.

M. Myers et al., "TYK2 and JAK2 Are Substrates of Protein-Tyrosine Phosphatase 1B", The Journal of Biological Chemistry, vol. 276, No. 51, (Dec. 21, 2001) pp. 47771-47774.

D. C. Lefebvre et al., "The Noncatalytic Domains of Lck Regulate Its Dephosphorylation by CD45", Biochimica et Biophysica Acta 1650, (2003) pp. 40-49.

U. Lehmann et al., "SHP2 and SOCS3 Contribute to Tyr-759-Dependent Attenuation of Interleukin-6 Signaling Through gp130", The Journal of Biological Chemistry, vol. 278, No. 1, (Jan. 3, 2003) pp. 661-671.

T. Bowman et al., "STAT Proteins and Cancer", Cancer Control, vol. 6, No. 6, (1999) pp. 615-619.

J. Turkson et al., "STAT Proteins: Novel Molecular Targets for Cancer Drug Discovery", Oncogene, vol. 19, (2000) pp. 6613-6626.

D. Sinibaldi et al., "Induction of p21 $^{WAF1/CIP1}$ and Cyclin D1 Expression by the Src Oncoprotein in Mouse Fibroblasts: Role of Activated STAT3 Signaling", Oncogene, vol. 19, (2000) pp. 5419-5427.

Y. Aoki et al., "Inhibition of STAT3 Signaling Induces Apoptosis and Decreases Survivin Expression in Primary Effusion Lymphoma", Blood, vol. 101, No. 4, (Feb. 15, 2003) pp. 1535-1542.

G. Niu et al., "Roles of Activated Src and Stat3 Signaling in Melanoma Tumor Cell Growth", Oncogene, vol. 21, (2002) pp. 7001-7010.

D. Wei et al., "Stat3 Activation Regulates the Expression of Vascular Endothelial Growth Factor and Human Pancreatic Cancer Angiogenesis and Metastasis", Oncogene, vol. 22, (2003) pp. 319-329.

T. Wang et al., "Regulation of the Innate and Adaptive Immune Responses by Stat-3 Signaling in Tumor Cells", Nature Medicine, vol. 10, No. 1, (Jan. 2004) pp. 48-54.

K. Shuai et al., "Enhancement of Antiproliferative Activity of Gamma Interferon by the Specific Inhibition of Tyrosine Dephosphorylation of Stat1", Molecular and Cellular Biology, vol. 16, No. 9, (Sep. 1996) pp. 4932-4941.

R. Garcia et al., "Constitutive Activation of Stat3 in Fibroblasts Transformed by Diverse Oncoproteins and in Breast Carcinoma Cells", Cell Growth & Differentiation, vol. 8, (Dec. 1997) pp. 1267-1276.

L. Mora et al., "Constitutive Activation of Stat3 in Human Prostate Tumors and Cell Lines: Direct Inhibition of Stat3 Signaling Induces Apoptosis of Prostate Cancer Cells", Cancer Research, vol. 62, (Nov. 15, 2002) pp. 6659-6666.

G. Niu et al., "Constitutive Stat3 Activity Up-Regulates VEGF Expression and Tumor Angiogenesis", Oncogene, vol. 21, (2002) pp. 2000-2008.

T. Bowman et al., "STATs in Oncogenesis", Oncogene, vol. 19, (2000) pp. 2474-2488.

T. N. Dechow et al., "Requirement of Matrix Metalloproteinase-9 for the Transformation of Human Mammary Epithelial Cells by Stat3-C", PNAS, vol. 101, No. 29, (Jul. 20, 2004) pp. 10602-10607.

P. Real et al., "Resistance to Chemotherapy Via Stat3-Dependent Overexpression of Bcl-2 in Metastatic Breast Cancer Cells", Oncogene, vol. 21, (2002) pp. 7611-7618.

P.K. Epling-Burnette et al., "Inhibition of STAT3 Signaling Leads to Apoptosis of Leukemia Large Granular Lymphocytes and Decreased Mcl-1 Expression", The Journal of Clinical Investigation, vol. 107, No. 3, (Feb. 2001) pp. 351-361.

M Neilson et al., "Inhibition of Constitutively Activated Stat3 Correlates With Altered Bcl-2/Bax Expression and Induction of Apoptosis in Mycosis Fungoides Tumor Cells", Leukemia, vol. 13, (1999) pp. 735-738.

M. Hamasaki et al., "Azaspirane (N-N-Diethyl-8,8-Dipropyl-2-Azaspiro [4.5] Decane-2-Propanamine) Inhibits Human Multiple Myeloma Cell Growth in the Bone Marrow Milieu In Vitro and In Vivo", Blood, vol. 105, No. 11, (Jun. 1, 2005) pp. 1-28 (Internet version).

W. Kammer et al., "Homodimerization of Interleukin-4 Receptor Chain Can Induce Intracellular Signaling", The Journal of Biological Chemistry, vol. 271, No. 39, (Sep. 27, 1996) pp. 23634-23637.

A. Lischke et al., "The Interleukin-4 Receptor Activates STAT5 by a Mechanism That Relies Upon Common γ-Chain", The Journal of Biological Chemistry, vol. 273, No. 47, (Nov. 20, 1998) pp. 31222-31229.

P. L. Bergsagel et al., "IgH Translocations in Multiple Myeloma: A Nearly Universal Event that Rarely Involves c-myc", Curr. Top. Microbiol. Immunol. vol. 224, (1997) pp. 283-287.

H. Jernberg-Wiklund et al., "Expression of myc-Family Genes in Established Human Multiple Myeloma Cell Lines: L-myc But Not c-myc Gene Expression in the U-266 Myeloma Cell Line", Int. J. Cancer, vol. 51, (1992) pp. 116-123.

David C. Cuellar et al., "Alpha1-adrenoceptor Antagonists Radiosensitize Prostate Cancer Cells via Apoptosis Induction", Anticancer Research, May-Jun. 2002, vol. 22, No. 3, pp. 1673-1680. (Abstract Only).

Kexin Xu et al., "Growth Inhibiting Effects of Terazosin on Androgen-independent Prostate Cancer Cell Lines", Chinese Medical Journal (English Edition), Nov. 2003, vol. 116, No. 11, pp. 1673-1677. (Abstract Only).

Anastasios Tahmatzopoulos et al., "Effect of Terazosin on Tissue Vascularity and Apoptosis in Transitional Cell Carcinoma of Bladder", Urology, May 2005, vol. 65, No. 5, pp. 1019-1023. (Abstract Only).

Kasper Keledjian et al., "Doxazosin Inhibits Human Vascular Endothelial Cell Adhesion, Migration, and Invasion", Journal of Cellular Biochemistry, Feb. 1, 2005, vol. 94, No. 2, pp. 374-388. (Abstract Only).

Anastasios Tahmatzopoulos et al., "Apoptotic Impact of Alpha1-blockers on Prostate Cancer Growth: A Myth or an Inviting Reality?", Prostate, Apr. 1, 2004, vol. 59, No. 1, pp. 91-100. (Abstract Only).

Cynthia M. Benning et al., "Quinazoline-derived Alpha1-adrenoceptor Antagonists Induce Prostate Cancer Cell Apoptosis via an Alpha1-adrenoceptor-independent Action", Cancer Research, Jan. 15, 2002, vol. 62, No. 2, pp. 597-602. (Abstract Only).

Michael Maes et al., "The Effects of Noradrenaline and Alpha-2 Adrenoceptor Agents on the Production of Monocytic Products", Psychiatry Research, Nov. 20, 2000, vol. 96, No. 3, pp. 245-253. (Abstract Only).

C. E. Rothwell et al., "Chronic Toxicity and Carcinogenicity Studies with the Beta-Adrenoceptor Antagonist Levobunolol", Fundamental and Applied Toxicology, 1992, vol. 18, No. 3, pp. 353-359. (Abstract Only).

J. V. Partin et al., "Quinazoline-based Alpha1-adrenoceptor Antagonists Induce Prostate Cancer Cell Apoptosis via TGF-beta Signalling and IkappaBalpha Induction", British Journal of Cancer, May 19, 2003, vol. 88, No. 10, pp. 1615-1621. (Abstract Only).

Baihua Hu et al., "Novel (4-Piperidin-1-yl)-phenyl Sulfonamides as Potent and Selective Human $\beta_3$ Agonists", Bioorganic & Medicinal Chemistry, 2001, pp. 2045-2059.

Silvère Aubriot et al., "New Series of Aryloxypropanolamines with Both Human $\beta_3$-Adrenoceptor Agonistic Activity and Free Radical Scavenging Properties", Bioorganic & Medicinal Chemistry Letters, 2002, pp. 209-212.

Lei Zheng et al., "Synthesis, Binding Properties, and $^{18}$F Labeling of Fluorocarazolol, a High-Affinity $\beta$-Adrenergic Receptor Antagonist", Journal of Medicinal Chemistry, 1994, vol. 37, No. 20, pp. 3219-3230.

Lichen Wang et al., "Synthesis and Bioactivity of 1-(9H-carbazol-4-yloxy)-3-substituted amino-2-propanol Compounds", Zhongguo Yaoke Daxue Xuebeo, 2001, vol. 32, No. 6, pp. 408-411. (Abstract Only).

* cited by examiner

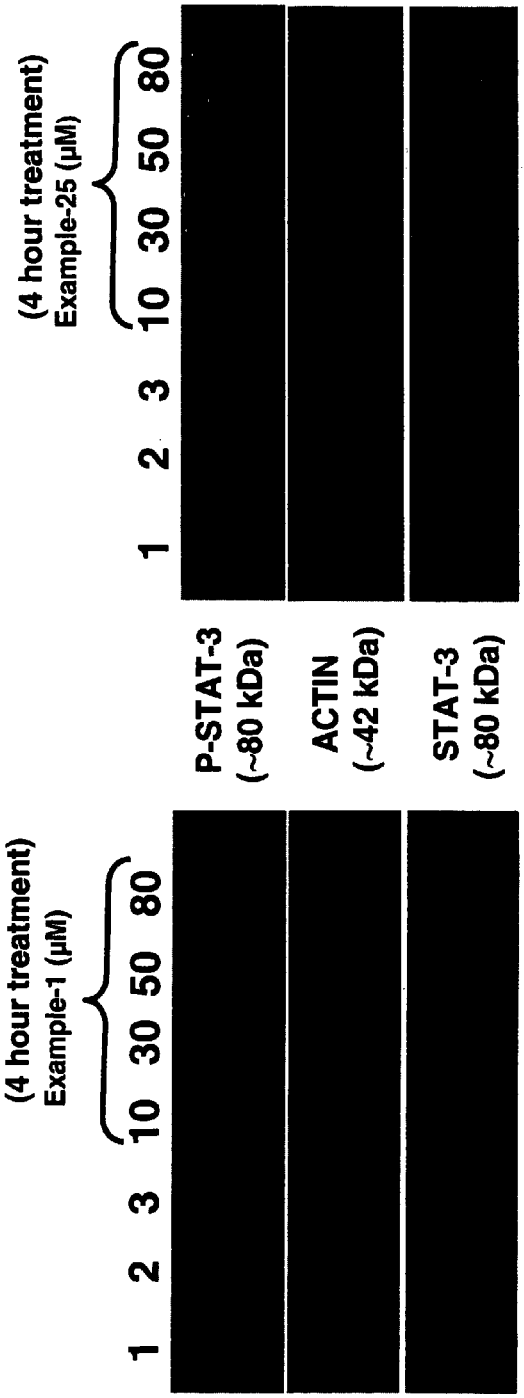

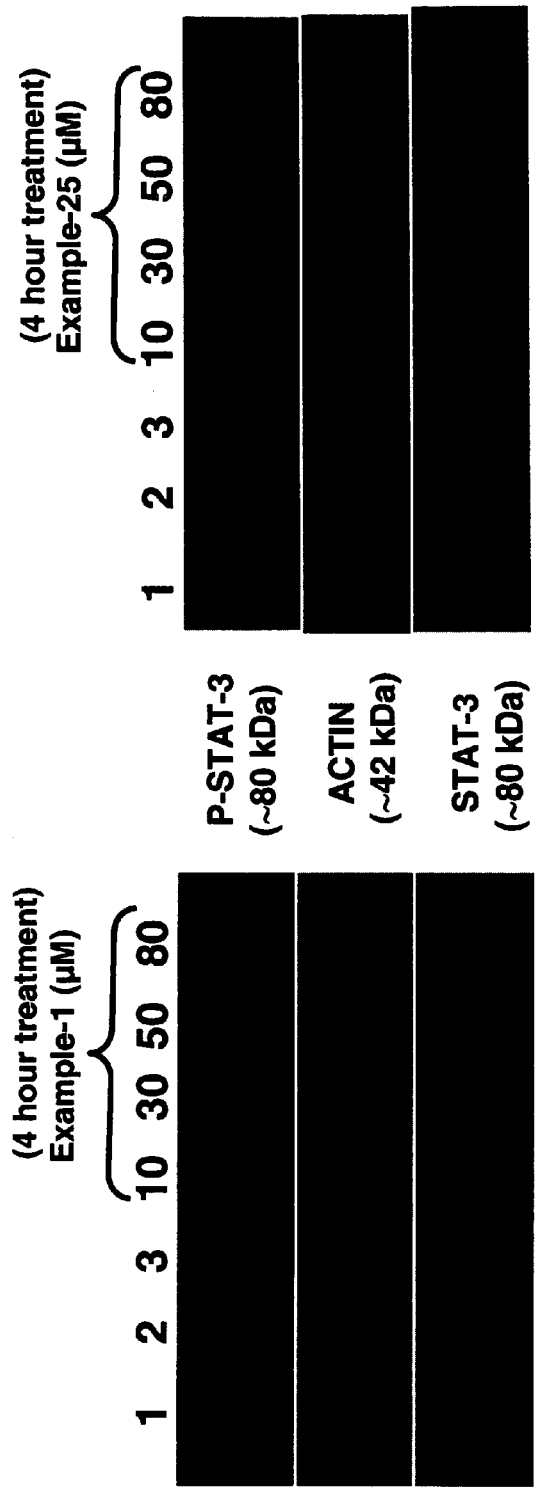

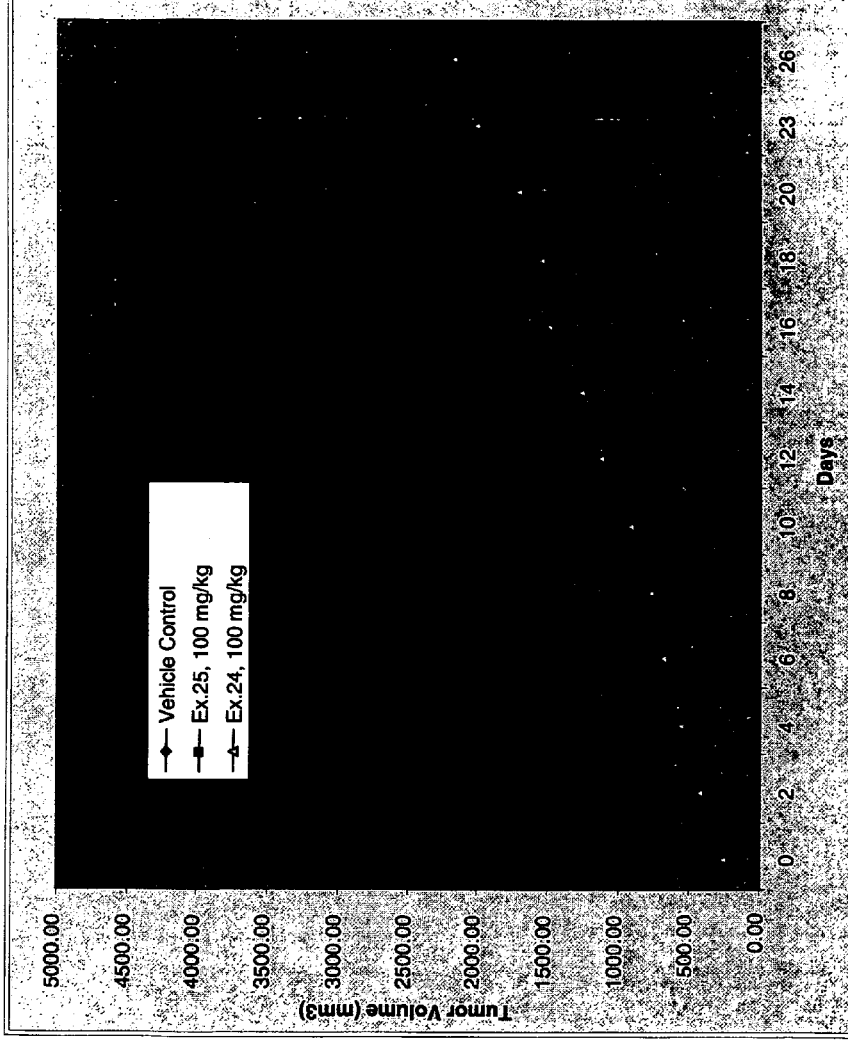
Figure: 3
Xenograft study: Evaluation of Anticancer activity of Examples 24 and 25 in NCI-H460 tumor bearing SCID mice

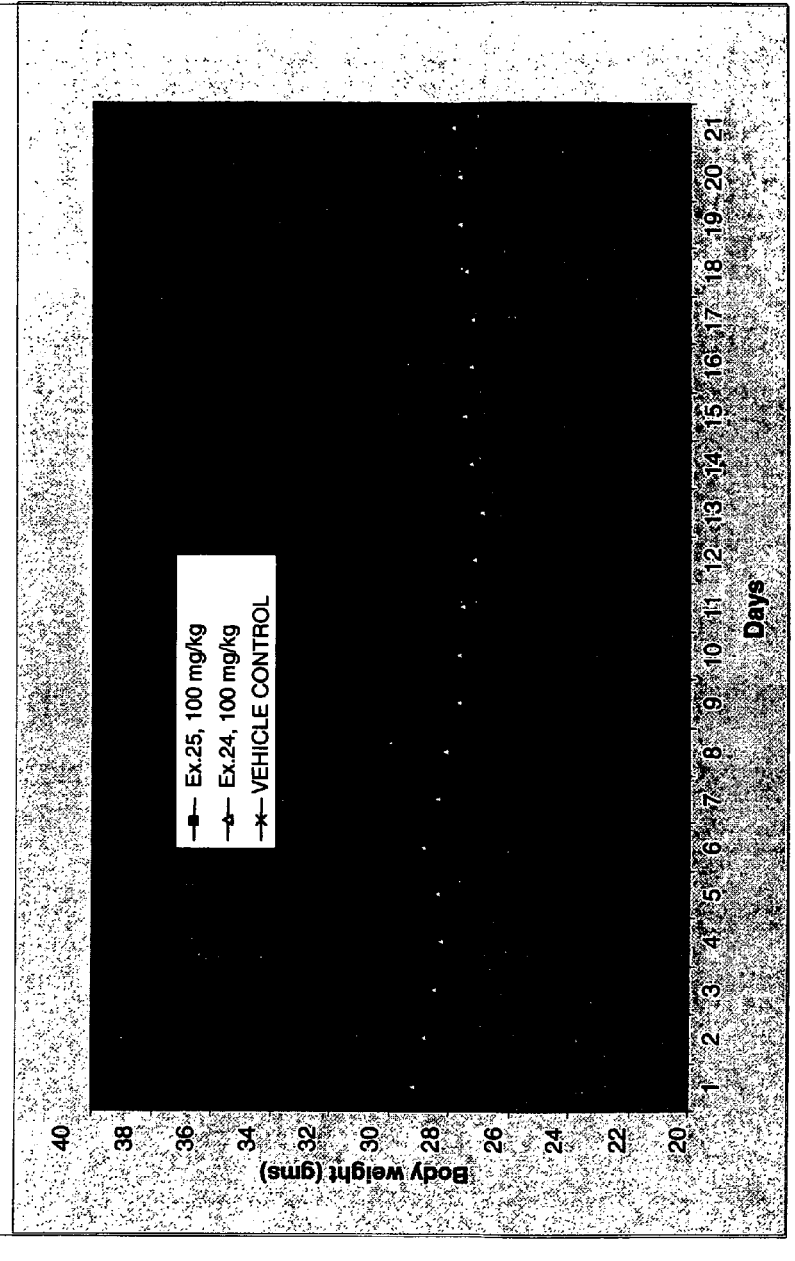
Figure : 4
Effect of Examples 24 and 25 on body weight change in NCI-H460 tumor bearing SCID mice during treatment period

HETEROCYCLIC COMPOUNDS AS PSTAT3/IL-6 INHIBITORS

FIELD OF THE INVENTION

The present invention relates to novel heterocyclic compounds of the general formula (I), as pSTAT3/IL-6 inhibitors, their derivatives, analogs, tautomeric forms, stereoisomers, polymorphs, hydrates, solvates, pharmaceutically acceptable salts and compositions, metabolites and prodrugs thereof.

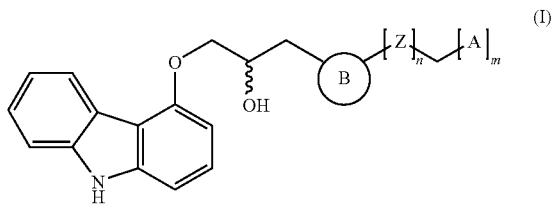

The present invention also provides a process for the preparation of the above said novel heterocyclic compounds of the formula (I), their derivatives, analogs, tautomeric forms, stereoisomers, polymorphs, hydrates, solvates, pharmaceutically acceptable salts and compositions, metabolites and prodrugs thereof. This invention also relates to intermediates useful in the preparation of such compounds.

The present invention relates generally to novel heterocyclic compounds and pharmaceutical compositions and more particularly to pSTAT3/IL-6 inhibitors, their use as modulators of the immune system, and as anticancer agents.

BACKGROUND OF THE INVENTION

Cancer may affect people at all ages, but risk tends to increase with age, due to the fact that DNA damage becomes more apparent in aging DNA. It is one of the principal causes of death in developed countries, more than 11 million people are diagnosed with cancer every year, and it is estimated that there will be 16 million new cases every year by 2020. Cancer causes 7 million deaths every year or 12.5% of deaths worldwide. Cancer is a leading cause of death worldwide particularly affecting major portion of people in industrialized world than in the non-industrialized world. From a total of 58 million deaths worldwide in 2005, cancer accounts for 7.6 million (or 13%) of all deaths. The main types of cancer leading to overall cancer mortality are Lung (1.3 million deaths/year), Stomach (almost 1 million deaths/year), Liver (662,000 deaths/year), Colon (655,000 deaths/year) and Breast (502,000 deaths/year). Deaths from cancer in the world are projected to continue rising, with an estimated 9 million people dying from cancer in 2015 and 11.4 million dying in 2030 (Parkin D et al, 2002)

Every cell constantly faces decisions. Should it divide? Or should it differentiate? Or should it die (Apoptosis)? Proper development and tissue homeostasis rely on the correct balance between division and apoptosis. Too much apoptosis leads to tissue atrophy such as in Alzheimer's disease. Too much proliferation or too little apoptosis leads to cancer. Cancer is a disease of multifactorial origin characterized by uncontrolled division of cells; when the cancer cell faces spatial restrictions, due to uncontrolled proliferation in an organ of the body, the ability of the cell to invade other distinct tissues occurs by a process defined as "Metastasis" the stage in which cancer cells are transported through the bloodstream or lymphatic system.

The most common treatment for easily accessible cancer is surgical removal of diseased tissues and radiation. The choice of treatment for in-accessible tumors is chemotherapy. Also chemotherapy is given as additional insurance for most cancer as it is difficult to access the extent of metastasis.

Most clinically revelant anticancer drugs currently used in clinic, interfere with cell division and hence are not highly selective to cancer cells and there are potential chances, that chemotherapy can lead to secondary cancers in due course of time. Also the quality of life is hampered in the patients upon chemotherapy, hence there is an unmet medical need for treating cancer patients without affecting the quality of life. (Hill R P et al., 2005 & Kleinsmith, L J, 2006).

The cell cycle deregulation and the molecular basis of cancer cell growth has been thoroughly exploited in the recent years. Inhibition of signal transduction has become a viable and attractive avenue in biomedical cancer research based on the discovery of a large number of somatic mutations in many different types of cancer that lead to deregulated growth signal transduction and subsequent aberrant growth, invasion, tumor-derived angiogenesis and metastasis. Most of the non-cytotoxic drugs that have been recently developed include Protein kinase inhibitors such as Gleevec, Iressa and Tarceva, Tyrosine kinase inhibitors like leflunomide. Glivec™ (STI571), is an inhibitor of the bcr-abl kinase and CML. PKI66, on the other hand, is a dual inhibitor of EGF receptor (HER 1) as well as erbB (HER 2). EGF-receptor and PTK787, potent inhibitors of VEGF-receptor 2 (KDR) are able to suppress tumor growth via suppression of tumor angiogenesis and also these agents have entered clinical trials in tumor patients (Alex Matter, M.D., 2002). These types of orally active and relatively well-tolerated compounds can be used in the clinics; either as single agents or in combination with other well established cytotoxic agents.

Cytokines play an important role in the communication between cells of multicellular organisms. Early studies indicate that B cells lineage tend to secrete IL6 in response to host immune defense mechanisms, but in recent decades studies have indicated elevated levels of IL6 in various cancer phenotypes. IL6 promotes survival and proliferation of certain cancerous cell lines through the phosphorylation of STAT3 (Bharti et al., Verma et al., Kerr et al.). Inhibitors of Jak/Stat pathway likely represent potential therapeutic target for cancer (Catlett Falcone et al., 1999; Alas and Bonavida, 2003; Burdelya et al., 2002)

IL6 has been found to be a growth factor for multiple myeloma cells; anti IL6 antibodies were shown to block myeloma cell proliferation in a leukemic patients (Lkein et al., Blood, 78, (5), pp 1198-1204, 1991 and Lu et al., Eur. J. Immunol., 22. 2819-24, 1992). A need exists for a compound that blocks IL6 mediated Stat3 activation at lower concentration and suppresses expression of proto-oncogene like c-myc, which is overexpressed, rearranged or mutated in many malignancies (Hallek et al., 1998; Selvanayagam et al., 1988; Jernberg-Wiklund et al., 1992; Kuehl et al., 1997).

Elevation of inflammatory cytokine levels, particularly IL-6 and TNF-α also appears to be associated with the Cancer-related cachexia, a syndrome involving loss of adipose and skeletal muscle tissue, and one that is not responsive to increased caloric intake. Cachexia may also be related to the role of acute phase proteins. The acute phase response and production of acute phase proteins (e.g., C-reactive protein [CRP]) are mediated by IL-6. Studies correlate elevated levels of IL-6 elevate acute phase proteins, which, interestingly, are also associated with increased weight loss and decreased survival. Thus, with elevated IL-6 levels, amino acid metabolism is directed away from peripheral tissues to the liver for production of acute phase proteins. This in turn leads to muscle wasting, which is a component of cachexia. Accordingly, the cytokine-induced acute phase response may be a primary component of cancer-related cachexia. Moreover, diminishing or blocking IL-6 activity in animal models attenuates cachexia, further demonstrating the essential role IL-6 plays in the development of this syndrome.

AG490 is a kinase inhibitor that inhibits Jak2/Stat3 signaling. Targeted inhibition of the Jak/Stat pathway with AG490 inhibits tumor cell growth and increases sensitivity to an apoptotic stimulus. AG490 has limited activity in animal studies and must be used at high concentration (~50-100 µM) to show Jak/Stat3 signaling inhibition and anti-tumor activity (Burdelya et al., 2002; Meydan et al., 1996; Constantin et al., 1998). Thus having an IL6 inhibitory activity, compound may be useful for various inflammatory diseases, sepsis, multiple myeloma, plasmacytoid leukemia, osteoporosis, cachexia, psoriasis, Nephritis, Kaposi's sarcoma, rheumatoid arthritis autoimmune disease, endometriosis and solid cancer (PCT: WO02/074298 A1)

Signal Transducers and Activators of Transcription (STATs):

STAT proteins convey signals from activated cytokines and growth factor receptors to target genes by translocating from the cytoplasm to the nucleus. STAT3 regulates genes involved in cell cycle progression and cell survival, and is commonly hyper-activated in human tumors, suggesting that STAT3 is a validated, and attractive, promising cancer target.

Signal transducers and activators of transcription (STATs) are a family of seven proteins (STATs 1, 2, 3, 4, 5a, 5b, and 6) unique in their ability both to transduce extracellular signals and regulate transcription directly. STATs transduce extracellular signals from cytokines such as interleukin-6 and interferons or growth factors such as platelet-derived growth factor (PDGF) and epidermal growth factor (EGF). Upon activation of these receptors, STATs are recruited to the plasma membrane where they become activated via phosphorylation of conserved tyrosine residues either directly by receptor tyrosine kinases.

In normal cells STAT proteins have been identified as important regulators of diverse physiological functions such as immune response, inflammation, proliferation, differentiation, development, cell survival, and apoptosis (Ihle and Kerr, 1995; Schindler and Darnell, 1995; Horvath and Darnell, 1997; Stark et al., 1998). STAT signaling is tightly regulated in normal cells, either through inhibition of upstream signaling proteins (e.g., internalization of receptors) or negative regulators of Src and JAK proteins, such as SOCS proteins, and Src family and JAK phosphatases (e.g., CD45 and SHP-2) (Irie-Sasaki et al., 2001; Myers et al., 2001; Lefebvre et al., 2003; Lehmann et al., 2003). However, in tumor cells and tissues, disregulation and constitutive activation of STATs, especially STAT3 and STAT5, have been demonstrated to be important to the proliferation and antiapoptotic activity of tumor cells (Bowman and Jove, 1999; Turkson and Jove, 2006).

STATs have been shown to play active roles at all levels of tumorigenesis. STATs are responsible for generating proproliferative signals (e.g., Cyclin D1, survivin; Sinibaldi et al., 2000; Aoki et al., 2003) and have been shown to upregulate antiapoptotic proteins (e.g., Bcl-XL, Bcl-2; Catlett-Falcone et al., 1999).

In addition, STAT3 has been demonstrated to upregulate VEGF expression, which is necessary for angiogenesis and the maintenance of tumor vasculature (Niu et al., 2002). Most tumors cannot sustain their growth unless they are supplied with oxygen and nutrients from newly formed blood vessels. One of the most potent angiogenesis inducing signals is vascular endothelial growth factor (VEGF). This usually produced by cancer cells in higher levels and VEGF binds to a transmembrane receptor tyrosine kinase on endothelial cells, activates endothelial-cell migration and proliferation to form new blood vessels. This STAT3 has been shown to be a direct transcription factor of the VEGF gene. Blocking STAT3 signaling has been shown to inhibit SRC and IL6 induced VEGF upregulation and might therefore also abrogate the induction of VEGF by other tyrosine kinase pathways that lie upstream (Niu et al., Oncogene, 21:2000-2008, 2002 and Wei, D et al., Oncogene 22: 319-329, 2003). Finally, STAT3 has been implicated in the inhibition of immune responses to tumor growth by blocking expression of proinflammatory factors (Wang et al., 2004).

Unregulated activation of STAT3 and STAT5 has been demonstrated in a variety of tumor types, including breast carcinoma, prostrate cancer, melanoma, multiple myeloma, and leukemia among others (Shuai et al., 1996; Garcia et al., 1997, 2001; Catlett-Falcone et al., 1999; Mora et al., 2002; Niu et al., 2002a). The constitutive activation of Stat3 is frequently detected in breast carcinoma cell lines but not in normal breast epithelial cells (Gracia et al., Cell. Growth. Differ. 8:1267 (1997); Bowman et al., Oncogene 19:2474, 2000). It has been reported that approximately 60 percent of breast tumors contains persistently activated STAT3 (Dechow et al., Proc. Natl. Acad. Sci USA 101:10602, 2004).

Activated STAT3 signaling directly contributes to malignant progression of cancer. STAT3 oncogenic function acts through the pro-survival proteins such as Mcl-1, Bcl-2, and BCl-XL and results in the prevention of apoptosis (Real et al., Oncogene 21:7611 (2002); Aoki et al., Blood 101:1535 (2003); Epling-Burnette et al., J. Clin. Invest. 107:351 (2001); Neilsen et al., Leukemia 13:735, 1999).

STAT3 as a molecular target has been further elucidated using an antisense approach (WO 2006/012625 A2) and as a vaccine candidate (WO2004/080394 A2).

Compositions containing STAT3 Decoy Oligonucleotides are useful in treating cancers in which STAT3 is activated, such as squamous cell carcinomas including squamous cell carcinoma of the head and neck (WO 2006/012625 A2).

STAT3 Antagonists and their use as Vaccines against Cancer: Ex vivo immunotherapeutic methods for treating and preventing cancer comprise decreasing STAT3 expression and/or function in tumor cells and the administration of such cells to a subject in need of treatment and/or prevention. This method also comprises activating T-cells by co-culturing the T-cells with the tumor cells with decreased STAT3 expression or function. It further encompasses methods comprising decreasing STAT3 expression or function in antigen-presenting cells and co-administering tumor cells and the antigen presenting cells with decreased STAT3 function to a patient (WO2004/080394 A2).

Atiprimod (N—N-diethl-8,8-dipropyl-2-azaspiro[4.5]decane-2-propanamine) is an orally bioavailable cationic amphiphilic compound which significantly inhibits production of interleukin (IL)-6 and inflammation in rat arthritis and autoimmune animal models. The effect of Atiprimod on human multiple myeloma (MM) cells has been characterized. Atiprimod significantly inhibited growth and induced caspase-mediated apoptosis in drug-sensitive and drug-resistant MM cell lines, as well as patient MM cells. Atiprimod inhibits STAT3 and Akt, but not ERK1/2, phosphorylation triggered by IL-6. It also inhibits NFkB p65 phosphorylation triggered by tumor necrosis factor (TNF-α). Importantly, Atiprimod inhibits both IL-6 and vascular endothelial growth factor (VEGF) secretion in BMSCs triggered by MM cell binding, and also inhibits angiogenesis on human umbilical vein cells (HUVEC). Finally, Atiprimod demonstrates in vivo antitumor activity against human MM cell growth in SCID mice. (Makoto Hamasaki et al, Blood First Edition Online Feb. 10, 2005; DOI 10.1182/blood-2004-09-3794)

Curcumin (chemically diferuloylmethane) a natural compound has been demonstrated as a pharmacologically safe agent in humans, inhibited IL6 induced STAT3 phosphorylation and consequent STAT3 translocation, and thus plays a role in the suppression of proliferation of MM. The constitutive phosphorylation of STAT3 found in certain multiple myeloma cells was also abrogated by the treatment of curcumin. Also this inhibition was reversible. (U.S. 2005/0049299 A1).

Attempts have also been made to inhibit STAT3 upstream regulators such as Janus kinases, especially Jak2 (Blaskovich et al., Cancer Res. 63:1270 (2000). There is a need to develop a small molecule inhibitor of STAT3 based on the structure of STAT3 with high cell permeability, stability that directly blocks STAT3 activation.

Few Prior Art References, which Disclose the Closest Compounds, are Given Here:

i) WO 98/09625 discloses compounds of formula (I) as Selective β3 adrenergic agonists

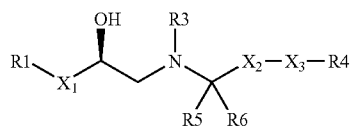

wherein, $X_1$ is —$OCH_2$—, —$SCH_2$, or a bond; $X_2$ is a bond, or a 1 to 5 carbon straight or branched alkylene; $X_3$ is O, S, or a bond; $R_1$ is a fused heterocycle of the formula

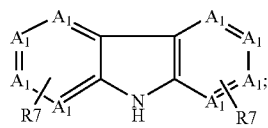

$R_3$ is hydrogen or $C_1$-$C_4$ alkyl; $R_4$ is an optionally substituted heterocycle or a moiety selected from the group consisting of structures cited therein; $R_5$ is hydrogen or $C_1$-$C_4$ alkyl; $R_6$ represents hydrogen, alkyl etc.

ii) U.S. Pat. No. 4,503,067 discloses carbazolyl-(4)-oxypropanolamine compounds of the formula (I)

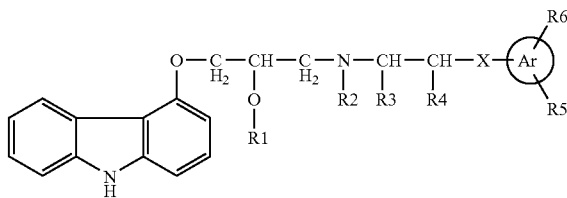

wherein, $R_1$ is hydrogen, lower alkanoyl or aroyl; $R_2$ is hydrogen, lower alkyl or arylalkyl; $R_3$ is hydrogen or lower alkyl; $R_4$ is hydrogen or lower alkyl, or when X is oxygen, $R_4$ together with $R_5$ can represent —$CH_2$—O—; X is a valency bond, —$CH_2$—, oxygen or sulfur; Ar is mono- or bicyclic aryl or pyridyl; $R_5$ and $R_6$ are individually selected from hydrogen, halogen, hydroxyl, lower alkyl, aminocarbonyl, lower alkoxy, aralkyloxy, lower alkylthio, lower alkylsulphinyl or lower alkylsulphonyl; $R_5$ and $R_6$ together can represent methylenedioxy; and the salts thereof with physiologically acceptable acids are outstandingly effective in the treatment and prophylaxis of circulatory and cardiac diseases e.g., hypertension and angina pectoris.

iii) WO 01/62705 discloses compounds of formula (I), as useful amino alcohol derivatives and salts thereof which have gut selective sympathomimetic, anti-ulcerous, anti-pancreatitis, lipolytic, anti-urinary incontinence and anti-pollakiuria activities,

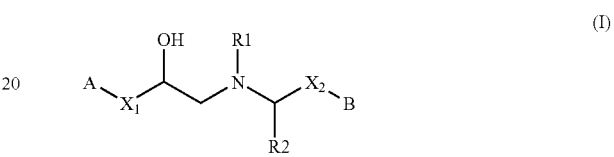

wherein, $X_1$ is bond or —$O(CH_2)m$- (m is an integral of 1, 2 or 3), $X_2$ is bond, —$(CH_2)n$- or —$CH_2O$—) (n is an integral of 1, 2, or 3) $R_1$ is hydrogen or an amino protective group; $R_2$ is hydrogen, (lower) alkyl or (lower) alkoxy or (lower) alkyl; A is phenyl, pyridyl, indolyl or carbazolyl, each of which may be substituted and B is phenyl or pyridyl each of which may be substituted with one or two substituents selected from the group consisting of halogen, hydroxyl, nitro, etc.; and a pharmaceutically acceptable salt thereof which is useful as a medicament.

OBJECTIVE OF THE INVENTION

Due to unmet medical needs and also as all of us know, cancer is one of the leading causes of death in the present society, we focused our attention to identify novel small molecule anticancer agents, particularly focusing on pSTAT3 and IL-6 inhibitors. Our sustained efforts have resulted in novel anticancer agents of the formula (I). STAT activation is dependent on tyrosine phosphorylation, which induces dimerization via, reciprocal phosphotyrosine (pTyr)-SH2 interactions between two STAT monomers and is a requirement for binding to specific DNA response elements. For example some of the molecules like AG-490, NSC-521777, JSI-124, ISS-221, ISS-637, ISS-610 and ISS-593 were reported in the literature as STAT inhibitors and all are in the pre-clinical stage. Because a variety of human cancers are associated with constitutively active pSTAT3, pSTAT3 represents an attractive target for cancer therapy. Most of the anticancer agents induce resistance through activation of anti-apoptotic genes upon treatment with cytotoxic drugs. Many of the anti-apoptotic gene targets are under the control of phospho-STAT3 hence a small molecule inhibitor of pSTAT3 will synergistically act with clinically relevant cytotoxic anticancer agents. Based on these literature references and our urge to develop a small molecule inhibitor we chose pSTAT3 as a molecular target for this project.

Another objective of the present invention is to provide novel heterocyclic compounds of the formula (I), and their pharmaceutically acceptable salts and compositions having enhanced activity, without toxic effect or with reduced toxic effect.

Yet another objective of the present invention is to provide a process for the preparation of novel heterocyclic compounds of the formula (I), and their pharmaceutically acceptable salts and compositions.

SUMMARY OF THE INVENTION

The present invention, relates to novel heterocyclic compounds of the formula (I), as pSTAT3/IL-6 inhibitors,

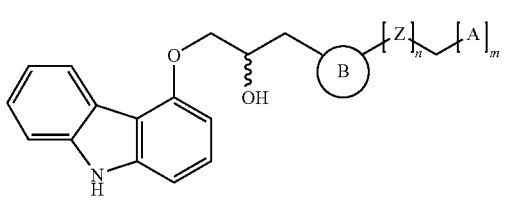

their derivatives, analogs, tautomeric forms, stereoisomers, polymorphs, hydrates, solvates, and pharmaceutically acceptable salts and compositions, wherein B represents substituted or unsubstituted groups selected from

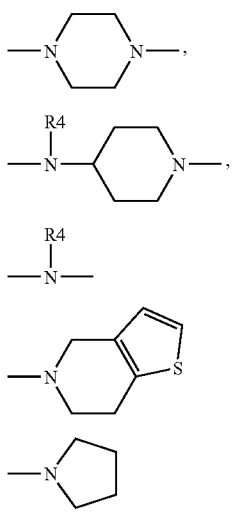

and $R_4$ represents hydrogen, alkyl, and benzyl; wherein Z represents —$CH_2$—, —CH—$CH_3$,

—C=O,

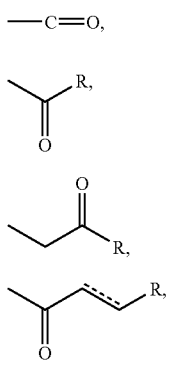

wherein - - - represents an optional bond,

and R represents $CH_2$, alkyl, and $NR_5$, wherein $R_5$ represents hydrogen, and alkyl; wherein n is an integer selected from 0 to 2; wherein ring A represents hydrogen, alkoxy, substituted or unsubstituted groups selected from aryl, aralkyl, aryloxy, heteroaryl, heterocyclyl, and cycloalkyl; wherein m is an integer selected from 0 to 1.

The foregoing merely summarizes certain aspects of the invention and is not intended, nor should it be construed, as limiting the invention in any way. All patents and other publications recited herein are hereby incorporated by reference in their entirety.

BRIEF DESCRIPTION OF DRAWINGS

FIG. 1: Shows IL-6 inhibition using compound of Example 1.

FIG. 2: Shows p-STAT-3 Inhibition in SKOV-3 cells using compound of Example 1.

FIG. 3: Shows Xenograft study: It is an Evaluation of Anticancer activity using compounds of Examples 24 and 25.

FIG. 4: Shows Effect of compounds of Examples 24 and 25 on body weight change in NCI-H460 tumor bearing SCID mice.

DETAILED DESCRIPTION OF THE INVENTION

The present invention relates to novel heterocyclic compounds of the formula (I), as pSTAT3/IL-6 inhibitors,

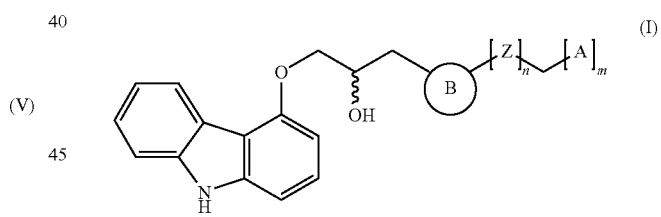

their derivatives, analogs, tautomeric forms, stereoisomers, polymorphs, hydrates, solvates, and pharmaceutically acceptable salts and compositions, wherein B represents substituted or unsubstituted groups selected from

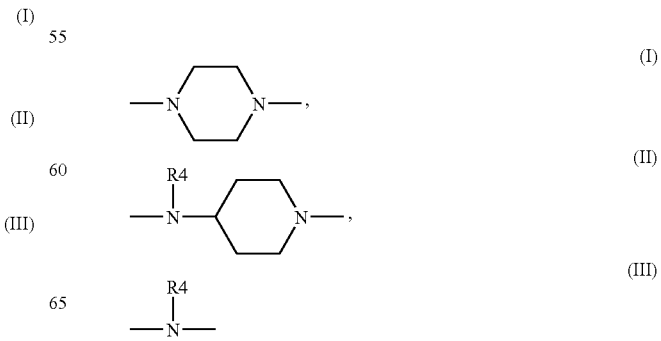

-continued

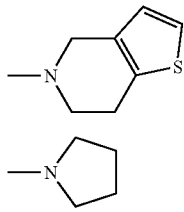
(IV)

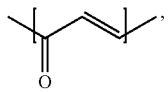
(V)

and $R_4$ represents hydrogen, alkyl, and benzyl.

Wherein Z represents

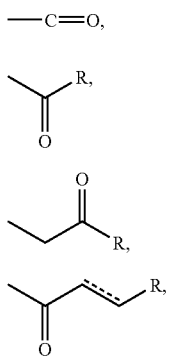

wherein - - - represents an optional bond, and R represents $CH_2$, alkyl, and $NR_5$, wherein $R_5$ represents hydrogen, and alkyl Wherein n is an integer selected from 0 to 2.

Wherein A represents, hydrogen, alkoxy groups such as linear or branched ($C_1$-$C_4$) alkoxy groups such as methoxy, ethoxy, n-propoxy, isopropoxy and the like; substituted or unsubstituted groups selected from aryl groups such as phenyl, naphthyl, benzyl, and the like; aralkyl groups such as benzyl and the like which may be substituted; aryloxy groups such as phenoxy, napthoxy and the like, which may be substituted; heteroaryl groups such as pyridyl, thienyl, furyl, pyrrolyl, oxazolyl, thiazolyl, thiadiazolyl, imidazolyl, oxadiazolyl, triazolyl, tetrazolyl, pyrimidinyl, pyrazinyl, pyrazolyl, indolyl, indolinyl, benzothiazolyl, benzothiadiazolyl, benzimidazolyl, benzodioxolyl, benzopyrazinyl and the like, which may be substituted; heterocyclyl groups such as pyrrolidinyl, N-methylpyrrolidinyl, thiazolidinyl, oxazolidinyl, morpholinyl, thiomorpholinyl, piperidinyl, piperazinyl and the like, which may be substituted; cycloalkyl groups such as cyclopropyl, cyclobutyl, cyclopentyl and the like which may be may be substituted; heterocyclyl groups such as pyrrolidinyl, thiazolidinyl, oxazolidinyl, morpholinyl, thiomorpholinyl, piperidinyl, piperazinyl, and the like, which may be substituted.

Wherein m is an integer selected from 0 to 1.

Furthermore A which is a cyclic ring represents substituted or unsubstituted 5 to 10 membered ring systems, and also the rings may be monocyclic or bicyclic, saturated or partially saturated or aromatic containing 1 to 4 hetero atoms selected from O, S and N and the like.

The ring A when substituted, the term substituted means that one or more hydrogen atoms are replaced by a substituent including, but not limited to, halogens (such as fluorine, chlorine, bromine, iodine), hydroxy, nitro, cyano, azido, nitroso, amino, amidino, hydrazine, formyl, alkyl groups such as methyl, ethyl, n-propyl, isopropyl, n-butyl and the like; aryl, cycloalkyl, alkoxy groups, such as methoxy, ethoxy, n-propoxy, isopropoxy and the like; aryloxy groups such as phenoxy, napthoxy and the like; aralkyl (e.g., benzyl), aralkoxy (e.g., benzyloxy), acyl, acyloxyacyl, carboalkoxy (e.g., acyloxy), carboxyalkyl (e.g., esters), carboxamido, aminocarbonyl, carbonyl, alkylenedioxy, heterocyclyl, heteroaryl groups such as pyridyl, thienyl, furyl, pyrrolyl, oxazolyl, thiazolyl, thiadiazolyl, imidazolyl, oxadiazolyl, triazolyl, tetrazolyl, pyrimidinyl, pyrazinyl, pyrazolyl, indolyl, indolinyl, benzothiazolyl, benzothiadiazolyl, benzimidazolyl, benzodioxolyl, benzopyrazinyl and the like; heteroaralkyl, heteroaryloxy, heteroaralkoxy, monoalkylamino, dialkylamino, acylamino, alkoxycarbonyl, aryloxycarbonyl, alkylsulfonyl, arylsulfonyl, alkylsulfinyl, arylsulfinyl, alkylthio, arylthio, sulfanyl, sulfinyl, sulfonyl, sulfamoyl, thiol, alkoxyalkyl groups, carboxylic acids and its derivatives. In addition, the substituents may be further substituted by groups such as nitro, halogens.

The term analog includes a compound, which differs from the parent structure by one or more C, N, O or S atoms. Hence, a compound in which one of the N atoms in the parent structure is replaced by an S atom is an analog of the former.

The term stereoisomer includes isomers that differ from one another in the way the atoms are arranged in space, but whose chemical formulas and structures are otherwise identical. Stereoisomers include enantiomers and diastereoisomers.

The term tautomers include readily interconvertible isomeric forms of a compound in equilibrium. The enol-keto tautomerism is an example.

The term polymorphs include crystallographically distinct forms of compounds with chemically identical structures.

The term pharmaceutically acceptable solvates includes combinations of solvent molecules with molecules or ions of the solute compound.

The term derivative refers to a compound obtained from a compound according to formula (I), an analog, tautomeric form, stereoisomer, polymorph, hydrate, pharmaceutically acceptable salt or pharmaceutically acceptable solvate thereof, by a simple chemical process converting one or more functional groups, such as, by oxidation, hydrogenation, alkylation, esterification, halogenation, and the like.

Pharmaceutically acceptable salts of the present invention include alkali metal salts like Li, Na, and K salts, alkaline earth metal salts like Ca and Mg salts, salts of organic bases such as diethanolamine, α-phenylethylamine, benzylamine, piperidine, morpholine, pyridine, hydroxyethylpyrrolidine, hydroxyethylpiperidine, guanidine, choline and the like, ammonium or substituted ammonium salts, aluminum salts. Salts also include amino acid salts such as glycine, alanine, cysteine, lysine, arginine, phenylalanine etc. Salts may include sulphates, nitrates, phosphates, perchlorates, borates, hydrohalides, acetates, tartrates, maleates, citrates, succinates, oxalates, palmoates, methanesulphonates, tosylates, benzoates, salicylates, hydroxynaphthoates, benzenesulfonates, ascorbates, glycerophosphates, ketoglutarates and the like. Pharmaceutically acceptable solvates may be hydrates or comprising of other solvents of crystallization such as alcohols.

Particularly Useful Compounds According to the Invention Include 1. 1-(9H-carbazol-4-yloxy)-3-[(2,4-dimethoxybenzyl)-amino]propan-2-ol;
2. 1-(9H-carbazol-4-yloxy)-3-{[2-(4-methylphenoxy)ethyl] amino}propan-2-ol;
3. 1-(9H-carbazol-4-yloxy)-3-piperazin-1-ylpropan-2-ol;
4. 1-(9H-carbazol-4-yloxy)-3-(6,7-dihydrothieno[3,2-c]pyridin-5(4H)-yl)propan-2-ol;
5. 1-(9H-carbazol-4-yloxy)-3-[benzyl(methyl)amino]propan-2-ol;
6. 1-(9H-carbazol-4-yloxy)-3-pyrrolidin-1-ylpropan-2-ol;
7. 3-[(4-Benzylpiperazin-1-yl)]-1-(9H-carbazol-4-yloxy) propan-2-ol;
8. 1-(9H-carbazol-4-yloxy)-3-(3,4,5-trimethoxyphenyl)propan-2-ol;
9. 1-(9H-carbazol-4-yloxy)-3-{[(1R)-1-phenylethyl] amino}propan-2-ol;
10. 1-(4-Acetylpiperazin-1-yl)-3-(9H-carbazol-4-yloxy)propan-2-ol;
11. t-Butyl 4-[2-hydroxy-3-(9H-carbazol-4-yloxy)propyl] piperazine-1-carboxylate;
12. 3-[(1-Benzylpiperidin-4-yl)amino]-1-(9H-carbazol-4-yloxy)pro-pan-2-ol;
13. 2-[(3-(9H-carbazol-4-yloxy)-2-hydroxypropyl)amino]-4-nitrophenol;
14. 1-(9H-carbazol-4-yloxy)-3-(cyclopropylamino)propan-2-ol;
15. 1-(9H-carbazol-4-yloxy)-3-[(4,6-dimethylpyrimidin-2-yl)amino]propan-2-ol;
16. 4-{[(3-(9H-carbazol-4-yloxy)-2-hydroxypropyl)amino] methyl}benzoic acid;
17. 1-[4-(1,3-Benzodioxol-5-ylmethyl)piperazin-1-yl]-3-(9H-carbazol-4-yloxy)propan-2-ol;
18. 1-[Benzyl-2,4-(dimethoxybenzyl)amino]-3-(9H-carbazol-4-yloxy)propan-2-ol;
19. 1-(1H-Benzimidazol-2-ylamino)-3-(9H-carbazol-4-yloxy)propan-2-ol;
20. 3-(9H-carbazol-4-yloxy)-1-[(5-mercapto-1,3,4-thiadiazol-2-yl)amino]propan-2-ol;
21. 3-(9H-carbazol-4-yloxy)-1-{[5-(2-furyl)-1H-pyrazol-3-yl]amino}propan-2-ol;
22. 3-(9H-carbazol-4-yloxy)-1-(2,1,3-benzothiadiazol-5-ylamino)propan-2-ol;
23. 1-(9H-carbazol-4-yloxy)-3-benzylaminopropan-2-ol;
24. (2R)-1-(9H-carbazol-4-yloxy)-3-[(2,4-dimethoxy-benzyl)amino]propan-2-ol;
25. (2S)-1-(9H-carbazol-4-yloxy)-3-[(2,4-dimethoxy-benzyl)amino]propan-2-ol;
26. 1-(9H-carbazol-4-yloxy)-3-{4-[(5-nitro-2-furyl)methyl] piperazin-1-yl}propan-2-ol;
27. 1-(9H-carbazol-4-yloxy)-3-{4-[(5-nitro-2-thienyl)methyl]piperazin-1-yl}propan-2-ol;
28. 1-(9H-carbazol-4-yloxy)-3-{4-[(thiazol-2-yl)methyl] piperazin-1-yl}propan-2-ol;
29. 1-(9H-carbazol-4-yloxy)-3-[4-(cyclopropylmethyl)piperazin-1-yl]propan-2-ol;
30. 1-(9H-carbazol-4-yloxy)-3-[4-(3,5-dimethoxybenzyl) piperazin-1-yl]propan-2-ol;
31. 1-(9H-carbazol-4-yloxy)-3-[4-(3,4-difluorobenzyl)piperazin-1-yl]propan-2-ol
32. 1-(9H-carbazol-4-yloxy)-3-[4-(4-bromo-2-fluorobenzyl) piperazin-1-yl]propan-2-ol
33. 1-(9H-carbazol-4-yloxy)-3-[4-(4-methylthiobenzyl)piperazin-1-yl]propan-2-ol;
34. 1-(9H-carbazol-4-yloxy)-3-[4-(2,4,6-trimethoxybenzyl) piperazin-1-yl]propan-2-ol;
35. 1-(9H-carbazol-4-yloxy)-3-{4-(5-nitro-2-furoyl)piperazin-1-yl}propan-2-ol;
36. 1-(9H-carbazol-4-yloxy)-3-[4-(5-nitro-1H-pyrazole-3-carbonyl)piperazin-1-yl]propan-2-ol;
37. 1-(9H-carbazol-4-yloxy)-3-[4-(2-furoyl)piperazin-1-yl] propan-2-ol;
38. 1-(9H-carbazol-4-yloxy)-3-[4-(1H-indole-2-carbonyl) piperazin-1-yl]propan-2-ol;
39. 1-(9H-carbazol-4-yloxy)-3-[4-(thiophene-2-carbonyl) piperazin-1-yl]propan-2-ol;
40. 1-(9H-carbazol-4-yloxy)-3-{4-[5-(4-nitrophenyl)-2-furoyl]piperazin-1 yl}propan-2-ol;
41. 1-(9H-carbazol-4-yloxy)-3-[4-(pyrazine-2-carbonyl)piperazin-1-yl]propan-2-ol;
42. 1-(9H-carbazol-4-yloxy)-3-[4-(3,4-dimethoxybenzoyl) piperazin-1-yl]propan-2-ol;
43. 1-(9H-carbazol-4-yloxy)-3-{4-[(4-methoxyphenyl) acetyl]piperazin-1-yl}propan-2-ol;
44. 1-(9H-carbazol-4-yloxy)-3-[4-(pentafluorophenyl) acetylpiperazin-1-yl]propan-2-ol;
45. 1-(9H-carbazol-4-yloxy)-3-{4-[(2E)-3-(1,3-benzodioxol-5-yl)acryloyl]piperazin-1-yl}propan-2-ol;
46. 1-(9H-carbazol-4-yloxy)-3-[4-(quinoxaline-2-carbonyl) piperazin-1-yl]propan-2-ol;
47. 1-(9H-carbazol-4-yloxy)-3-[4-(6-cyanonicotine-3-carbonyl)piperazin-1-yl]propan-2-ol;
48. 1-(9H-carbazol-4-yloxy)-3-[4-(pyridin-3-ylacetyl)piperazin-1-yl]propan-2-ol;
49. 1-(9H-carbazol-4-yloxy)-3-[4-(thiophen-3-ylacetyl)piperazin-1-yl]propan-2-ol;
50. 1-(9H-carbazol-4-yloxy)-3-[4-(1,3-benzodioxol-5-ylcarbonyl)piperazin-1-yl]propan-2-ol;
51. 1-(9H-carbazol-4-yloxy)-3-{4-[3-(1H-indole-2-carbonyl)propanoyl]piperazin-1-yl}propan-2-ol;
52. 1-(9H-carbazol-4-yloxy)-3-[4-(4-fluoro-1H-indole-2-carbonyl)piperazin-1-yl]propan-2-ol;
53. 1-(9H-carbazol-4-yloxy)-3-[4-(3-fluoro-4-hydroxyphenyl)acetylpiperazin-1-yl]propan-2-ol;
54. 3-[4-(1-Benzofuran-2-ylcarbonyl)piperazin-1-yl]-1-(9H-carbazol-4-yloxy)propan-2-ol;
55. 1-(9H-carbazol-4-yloxy)-3-[4-(4-fluorophenyl) acetylpiperazin-1-yl]propan-2-ol;
56. 3-[4-(5-Bromothiophene-2-carbonyl)piperazin-1-yl]-1-(9H-carbazol-4-yloxy) propan-2-ol;
57. 3-[4-(3-aminopropanoyl)piperazin-1-yl]-1-(9H-carbazol-4-yloxy)propan-2-ol;
58. 2-{4-[3-(9H-carbazol-4-yloxy)-2-hydroxypropyl]-piperazin-1-yl}-N-(5-methyl-1,3-thiazol-2-yl)acetamide;
59. 2-{4-[3-(9H-carbazol-4-yloxy)-2-hydroxypropyl]-piperazin-1-yl}-N-(4-methyl-1,3-benzothiazol-2-yl)acetamide;
60. 2-{4-[3-(9H-carbazol-4-yloxy)-2-hydroxypropyl]-piperazin-1-yl}-N-(4-methyl-1,3-thiazol-2-yl)acetamide;
61. 2-{4-[3-(9H-carbazol-4-yloxy)-2-hydroxypropyl]-piperazin-1-yl}-N-(4-methoxy-1,3-benzothiazol-2-yl)acetamide;
62. 2-{4-[3-(9H-carbazol-4-yloxy)-2-hydroxypropyl]-piperazin-1-yl}-N-phenyl acetamide;
63. 2-{4-[3-(9H-carbazol-4-yloxy)-2-hydroxypropyl]-piperazin-1-yl}-N-(2,4-dimethoxybenzyl)acetamide;

64. 1-(9H-carbazol-4-yloxy)-3-{[1-(5-nitro-2-furoyl)piperidin-4-yl]amino}propan-2-ol;
65. 1-(9H-carbazol-4-yloxy)-3-{[1-(1-methyl-1H-pyrrole-2-carbonyl)piperidin-4-yl]amino}propan-2-ol;
66. 1-(9H-carbazol-4-yloxy)-3-{[1-(4-fluorophenyl)acetyl) piperidin-4-yl]amino}propan-2-ol;
67. 1-(9H-carbazol-4-yloxy)-3-{[1-(3,4-dimethoxybenzoyl) piperidin-4-yl]amino}propan-2-ol;
68. 3-{[1-(1,3-Benzodioxol-5-ylcarbonyl)piperidin-4-yl] amino}-1-(9H-carbazol-4-yloxy)propan-2-ol;
69. 1-(9H-carbazol-4-yloxy)-3-{[1-(pentafluorophenyl) acetylpiperidin-4-yl]amino}propan-2-ol;
70. 1-(9H-carbazol-4-yloxy)-3-{[1-(6-cyanonicotine-3-carbonyl)piperidin-4-yl]amino}propan-2-ol;
71. 1-(9H-carbazol-4-yloxy)-3-{[1-(4-methoxyphenylacetyl)piperidin-4-yl]amino}propan-2-ol;
72. N-[3-(9H-carbazol-4-yloxy)-2-hydroxypropyl]-3,4-dimethoxy-N-methylbenzamide;
73. 1-(9H-carbazol-4-yloxy)-3-[3,5-dimethoxybenzyl(methyl)amino]propan-2-ol;
74. 1-(9H-carbazol-4-yloxy)-3-[4-(3-trifluoromethylphenylsulfonyl)piperazin-1-yl]propan-2-ol and
75. 3-[4-(4-Acetylphenylsulfonyl)piperazin-1-yl]-1-(9H-carbazol-4-yloxy)propan-2-ol.

Preferred salts for the list of compounds above are hydrochloride, citrate, phosphonate, mesylate, besylate, tosylate, and oxalate.

According to another feature of the present invention, there is provided a process as shown in the following schemes, for the preparation of novel heterocyclic compounds of the general formula (I), wherein all the groups are as defined earlier.

1(c), which was further reacted with an amine of formula 1(d), in the presence of a suitable base like pyridine, triethylamine, sodium carbonate, potassium carbonate, sodium hydroxide, potassium hydroxide in a suitable solvent like methanol, ethanol, propanol, isopropanol, chloroform, dichloromethane, ethyl acetate, THF, acetone to yield a compound of formula 1.

The compound of formula 1(c) on reaction with methylamine in the presence of a suitable base like pyridine, triethylamine, sodium carbonate, potassium carbonate, sodium hydroxide, potassium hydroxide in a suitable solvent like methanol, ethanol, propanol, isopropanol, chloroform, dichloromethane, ethyl acetate, THF, acetone afforded the compound of formula 1(e), which on further reaction with acids in the presence of EDCI, HOBt, DIPEA, and in the presence of solvents like THF, DMF, ethyl acetate yielded the compound of formula 1.

Alternatively the compound of formula 1(e) on reaction with aldehydes in the presence of triacetoxysodiumborohydride, triethylamine, acetic acid in a suitable solvent like THF, DCM, methanol, ethanol yielded a compound of formula 1.

The compound of formula 1(c) was further reacted with 4-amino-1-benzylpiperidine in the presence of a suitable base like pyridine, triethylamine, sodium carbonate, potassium carbonate, sodium hydroxide, potassium hydroxide in a suitable solvent like methanol, ethanol, propanol, isopropanol, chloroform, dichloromethane, ethyl acetate, THF, acetone to yield a compound of formula 1(f). Debenzylation of compound of formula 1(f) using Pd/C under $H_2$ pressure in pres-

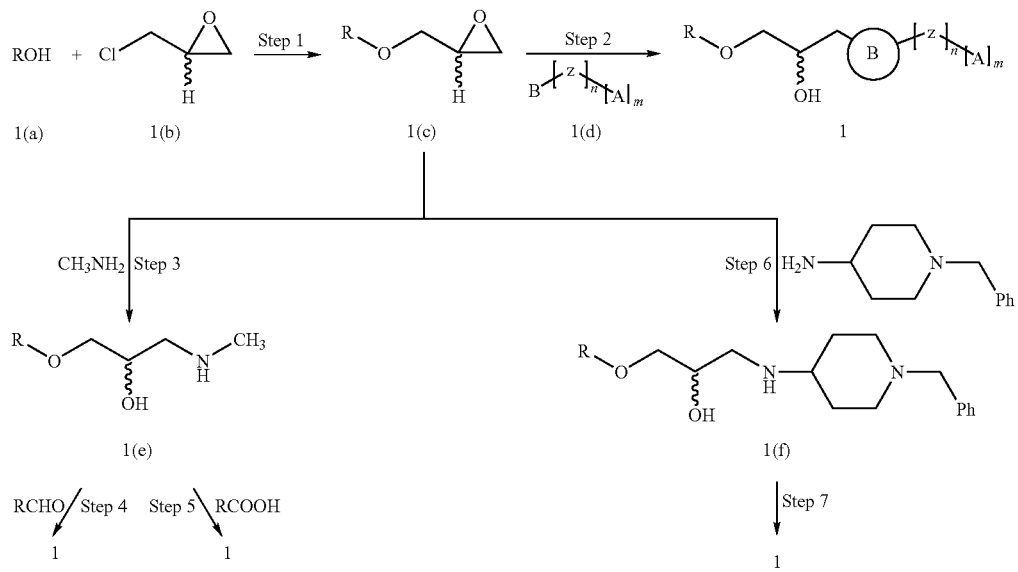

Scheme 1:

The condensation of compound of formula 1(a) with the compound of formula 1(b) using a suitable base such as pyridine, triethylamine, DIPEA, potassium carbonate, sodium carbonate, sodium hydroxide, potassium hydroxide, sodium hydride in a suitable solvent like methanol, ethanol, propanol, isopropanol, chloroform, dichloromethane, ethyl acetate, DMSO, acetonitrile yielded a compound of formula ence of a suitable solvent such as methanol, ethanol, isopropanol or reaction with 1-chloroethyl chloroformate in the presence of solvents like methanol, ethanol, propanol, isopropanol, chloroform, dichloromethane, ethyl acetate, THF, acetone, followed by coupling with acids in the presence of EDCI, HOBt, DIPEA, and in the presence of solvents like THF, DMF, ethyl acetate yielded the compound of formula 1.

Scheme 2:

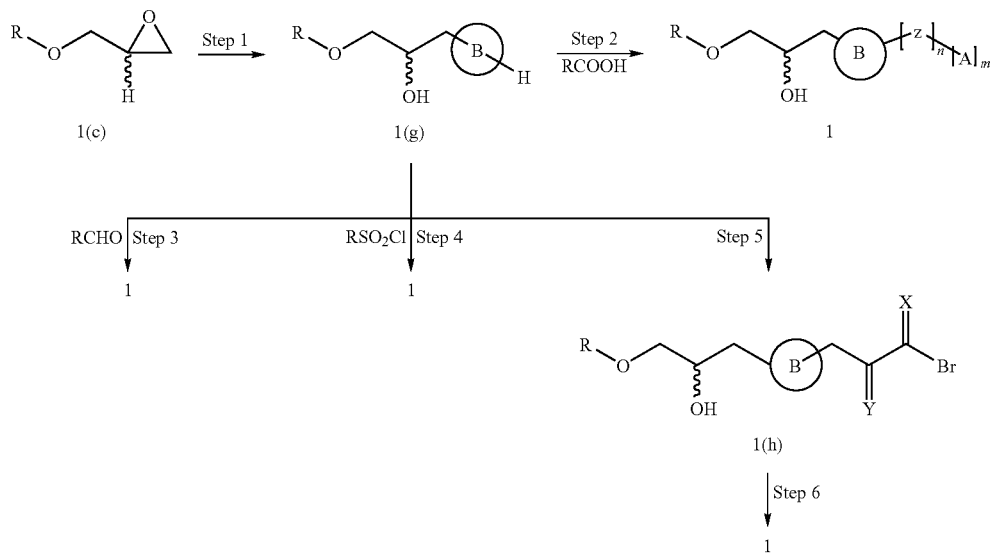

The compound of formula 1(c) was reacted with

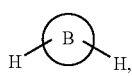

in the presence of a suitable base like pyridine, triethylamine, sodium carbonate, sodium hydroxide, potassium carbonate, potassium hydroxide in a suitable solvent like methanol, ethanol, propanol, isopropanol, chloroform, dichloromethane, ethyl acetate, to yield a compound of formula 1(g), which on further reaction with acids in the presence of EDCI, HOBt, DIPEA, and in the presence of solvents like THF, DMF, ethyl acetate yielded a compound of formula 1.

Alternatively the compound of formula 1(g) on reaction with aldehydes in the presence of triacetoxysodiumborohydride, triethylamine, acetic acid in a suitable solvent like THF, DCM, methanol, ethanol yielded a compound of formula 1.

The reaction of compound of formula 1(g) with $RSO_2Cl$ in the presence of a suitable base like pyridine, triethylamine, sodium carbonate, sodium hydroxide, potassium carbonate, potassium hydroxide in a suitable solvent like methanol, ethanol, propanol, isopropanol, chloroform, dichloromethane, ethyl acetate, yielded the compound of formula 1.

The compound of formula 1(g) on reaction with bromoacetyl bromide in the presence of a suitable base like pyridine, triethylamine, sodium carbonate, sodium hydroxide, potassium carbonate, potassium hydroxide in a suitable solvent like methanol, ethanol, propanol, isopropanol, chloroform, dichloromethane, ethyl acetate, yielded a compound of formula 1(h), which was further condensed with amines in the presence of a suitable base like pyridine, triethylamine, sodium carbonate, sodium hydroxide, potassium carbonate, potassium hydroxide in a suitable solvent like methanol, ethanol, propanol, isopropanol, chloroform, dichloromethane, ethyl acetate, to yield a compound of formula 1.

EXAMPLE: 1

Synthesis of 1-(9H-carbazol-4-yloxy)-3-[(2,4-dimethoxybenzyl)amino]propan-2-ol

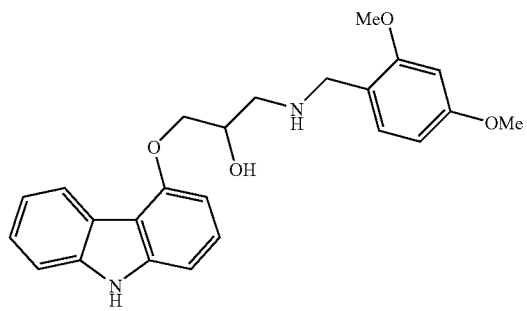

Step 1: Preparation of 4-(Oxiran-2-ylmethoxy)-9H-carbazole

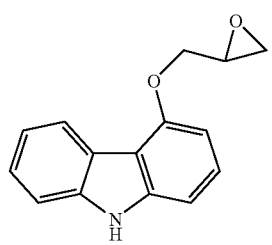

IPA (70 ml) was added to a mixture of 4-Hydroxy carbazole (0.05458 moles, 10 g) and epichlorohydrin (0.10916 moles, 8.5 ml). Potassium carbonate (0.13645 moles, 18.85 g) was added to the above reaction mixture and stirred. Subsequently the reaction mixture was heated to 75-85° C. After 6 hours when the reaction was complete, the reaction mixture was slowly cooled to room temperature and filtered. The filtrate was reduced to 80% of its volume, and stirred at room temperature, when a solid was formed which was filtered to give the product.

Step 2: Preparation of 1-(9H-carbazol-4-yloxy)-3-[(2,4-dimethoxybenzyl)amino]propan-2-ol

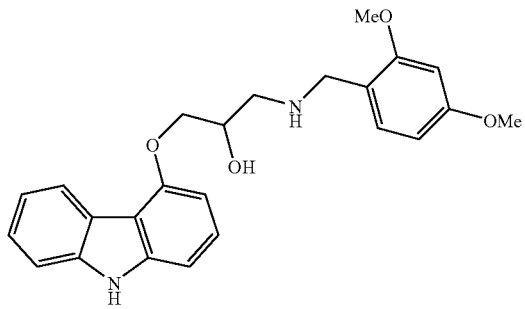

To a stirred solution of Epoxy carbazole (5 gm, 0.0209 mole) in IPA (20 ml), 2,4-dimethoxybenzylamine (9.42 ml, 0.06276 moles) was added, and the reaction mixture was heated to reflux for 3 hours. Subsequently the reaction mixture was cooled and IPA was stripped off. To the semisolid residue obtained, ethyl acetate (50 ml) was added and it was refluxed for 1.5 hours, until everything dissolved. A light yellow colored clear solution was finally obtained, which was stirred at room temperature for 5 hours when it completely crystallized out as a white solid (8 g, 94.2%), m.p: 152-154° C., $^1$H NMR (400 MHz, CDCl$_3$): δ 2.89(m 1H), 2.99(d 1H), 3.74(s 3H), 3.78(s 3H), 3.81(d 2H), 4.27(m, 3H), 6.42(m 2H), 6.65(d 1H), 7.08(d 1H), 7.14(m 2H), 7.29(m 1H), 7.35(d 1H), 7.43(d 1H), 8.22(d 1H), 9.42(s 1H); m/z$^{M+1}$ 406.

Following Compounds were Prepared Following the Procedure Given in Example: 1

| Example | Structure | Analytical data |
|---|---|---|
| 2 | 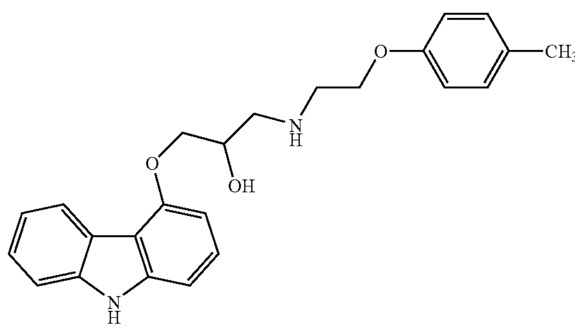 | $^1$H NMR(400 MHz, CDCl$_3$) δ (ppm): 2.28 (s, 2H), 3.01-3.13(m, 4H), 4.06-4.08(m, 2H), 4.24-4.32(m, 3H), 6.68(d, 1H, J=8.0 Hz), 6.80(d, 2H, J=8.0 Hz), 7.05-7.07(m, 3H), 7.20-7.25(m, 1H), 7.30-7.40(m, 3H), 8.09(s, 1H), 8.26(d, 1H, J=8.0 Hz). MS m/z: 392.9(M + 2). |
| 3 | 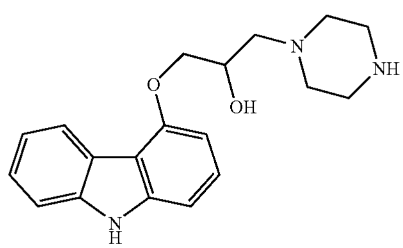 | $^1$H NMR(400 MHz, CDCl$_3$) δ (ppm): 2.25-2.50 (m, 2H), 2.52-2.65(m, 4H), 2.70-2.85 (m, 4H), 4.20-4.35(m, 3H), 6.67(d, 1H, J=8.0 Hz), 7.08(d, 1H, J=8.0 Hz), 7.15-7.25 (m, 1H), 7.28-7.40(m, 2H), 7.44(d, 1H, J=8.0 Hz), 8.28(d, 1H, J=8.0 Hz), 9.39(s, 1H). MS m/z: 326.1(M + 1) |
| 4 | 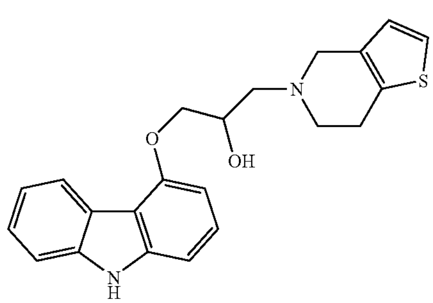 | $^1$H NMR(400 MHz, CDCl$_3$) δ (ppm): 2.80-2.98 (m, 5H), 3.00-3.10(m, 1H), 4.25-4.30 (m, 1H), 4.30-4.42 9m, 2H), 5.29(s, 1H), 6.69(d, 1H, J=8.0 Hz), 6.76(d, 1H, J=8.0 Hz), 7.06(d, 2H, J=8.0 Hz), 7.12(d, 1H, J=5.2 Hz), 7.25-7.52(m, 3H), 8.08(s, 1H), 8.28(d, 1H, J=8.0 Hz). MS m/z: 379.1 (M + 1) |

| Example | Structure | Analytical data |
|---|---|---|
| 5 | (carbazole-O-CH2-CH(OH)-CH2-N(CH3)-CH2-Ph) | $^1$H NMR(400 MHz, CDCl$_3$) δ (ppm): 2.35 (s, 3H), 2.70-2.82(m, 2H), 3.56-3.59(m, 1H), 3.72-3.76(m, 1H), 4.20-4.22(m, 1H), 4.27-4.35(m, 2H), 6.66(d, 1H, J=8.0 Hz), 7.04(d, 1H, J=8.0 Hz), 7.20-7.35(m, 6H), 7.36-7.40(m, 2H), 8.08(s, 1H), 8.24(d, 1H, J=8.0 Hz). MS m/z: 361.0(M + 1) |
| 6 | (carbazole-O-CH2-CH(OH)-CH2-pyrrolidine) | $^1$H NMR(400 MHz, CDCl$_3$) δ (ppm): 1.90-2.04 2.04(m, 4H), 2.65-2.69(m, 2H), 2.80-2.84 (m, 3H), 2.97-3.05(m, 1H), 4.20-4.25(m, 1H), 4.30-4.35(m, 2H), 6.68(d, 1H, J=8.0 Hz), 7.06(d, 1H, J=8.0 Hz), 7.20-7.45(m, 4H), 8.10(s, 1H), 8.27(d, 1H, J=8.0 Hz). MS m/z: 311.1(M + 1) |
| 7 | (carbazole-O-CH2-CH(OH)-CH2-piperazine-CH2-Ph) | $^1$H NMR(400 MHz, CDCl$_3$) δ (ppm): 2.40-2.60 (m, 4H), 2.65-2.80(m, 4H), 3.54(s, 2H), 4.09-4.15(m, 2H), 4.17-4.25(m, 1H), 4.25-4.35(m, 2H), 5.29(s, 1H), 6.67(d, 1H, J=8.0 Hz), 7.04(d, 1H, J=8.0 Hz), 7.20-7.50 (m, 8H), 8.10(s, 1H), 8.26(d, 1H, J=8.0 Hz). MS m/z: 416.2(M + 1) |
| 8 | (carbazole-O-CH2-CH(OH)-CH2-NH-3,4,5-trimethoxyphenyl) | $^1$H NMR(400 MHz, CDCl$_3$) δ (ppm): 2.65 (s, 1H), 3.45-3.49(m, 1H), 3.55-3.62(m, 1H), 3.76(s, 9H), 4.36-4.38(m, 2H), 4.47 (s, 1H), 5.93(s, 2H), 6.69(d, 1H, J=8.0 Hz), 7.09(d, 1H, J=8.0 Hz), 7.20-7.45(m, 4H), 8.15(s, 1H), 8.26(d, 1H, J=8.0 Hz). MS m/z: 423.1(M + 1) |
| 9 | (carbazole-O-CH2-CH(OH)-CH2-NH-CH(CH3)-Ph) | $^1$H NMR(400 MHz, CDCl$_3$) δ (ppm): 1.35-1.44 (m, 3H), 1.75-2.10(m, 1H), 2.85(d, 2H, J=5.2 Hz), 4.08-4.20(m, 3H), 6.62(d, 1H, J=8.0 Hz), 7.00-7.05(m, 1H), 7.22-7.38 (m, 10H), 8.13-8.25(m, 2H). MS m/z: 361.1(M + 1) |

-continued

| Example | Structure | Analytical data |
|---|---|---|
| 10 | 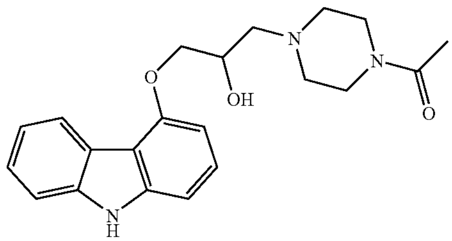 | $^1$H NMR(400 MHz, CDCl$_3$) δ (ppm): 2.04-2.15 (m, 4H), 2.50-2.60(m, 2H), 2.70-2.80 (m, 4H), 3.52(s, 3H), 3.60-3.75(m, 2H), 4.20-4.30(m, 1H), 6.68(d, 1H, J=8.0 Hz), 7.07(d, 1H, J=8.0 Hz), 7.20-7.30(m, 1H), 7.31-7.35(m, 1H), 7.39-7.45(m, 2H), 8.12 (s, 1H), 8.25(d, 1H, J=8.0 Hz). MS m/z: 368.1(M + 1) |
| 11 | 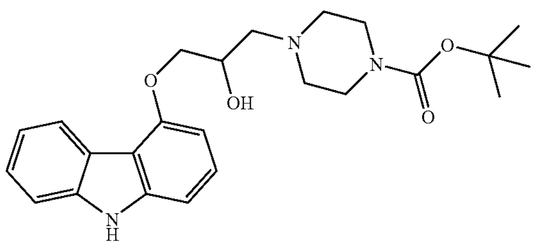 | $^1$H NMR(400 MHz, CDCl$_3$) δ (ppm): 1.23-1.28 (m, 1H), 1.47(s, 1H), 2.45-2.52(m, 2H), 2.60-2.80(m, 4H), 3.45-3.75(m, 4H), 4.25-4.32(m, 3H), 6.67(d, 2H, J=8.0 Hz), 7.06(d, 2H, J=8.0 Hz), 7.21-7.45(m, 4H), 8.17(s, 1H), 8.25(d, 1H, J=8.0 Hz). MS m/z: 426.2(M + 1) |
| 12 | 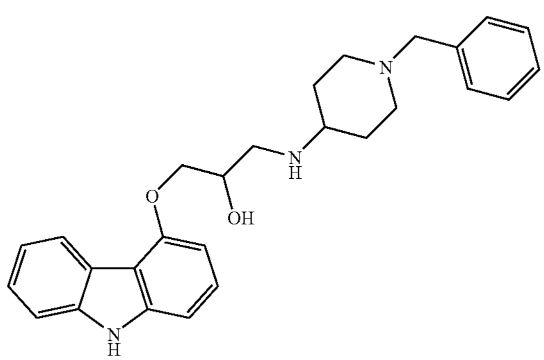 | $^1$H NMR(400 MHz, CDCl$_3$) δ (ppm): 1.60-2.25 (m, 9H), 3.50-3.58(m, 4H), 4.20-4.55 (m, 3H), 6.62-6.67(m, 1H), 7.03-7.39(m, 1H), 8.18-8.25(m, 2H). MS m/z: 430.2 (M + 1) |
| 13 | 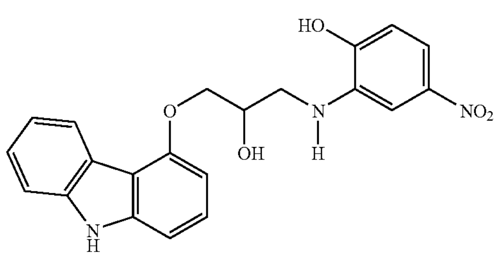 | $^1$H NMR(400 MHz, DMSO) δ (ppm): 3.20-3.40(m, 2H), 4.00-4.40(m, 3H), 6.60-7.00 (m, 2H), 7.05-7.30(m, 2H), 7.35-7.60 (m, 5H). 8.26(d, 1H, J=8.0 Hz), 11.24(d, 1H, J=8.0 Hz). MS m/z: 393.9(M + 1) |
| 14 | 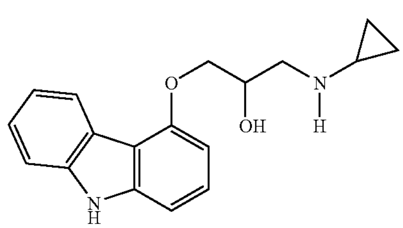 | $^1$H NMR(400 MHz, DMSO) δ (ppm): 1.10-1.40(m, 2H), 1.80-2.05(m, 2H), 2.20-2.40 (m, 2H), 2.98(d, 1H, J=8.0 Hz), 4.00-4.20 (m, 3H), 5.00-5.10(m, 2H), 6.67(d, 1H, J=8.0 Hz), 7.00-7.20(m, 2H), 7.25-7.40 (m, 2H), 7.44(d, 1H, J=8.0 Hz), 7.70-7.80 (m, 1H), 8.21(d, 1H, J=8.0 Hz), 11.24(s, 1H). MS m/z: 297.4(M + 1) |

-continued

| Example | Structure | Analytical data |
|---|---|---|
| 15 | 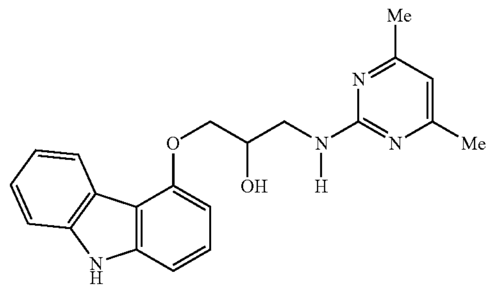 | $^1$H NMR(400 MHz, DMSO) δ (ppm): 3.10-3.70(m, 9H), 3.90-4.40(m, 3H), 6.29 (s, 1H), 6.69(d, 1H, J=8.0 Hz), 7.05-7.13 (m, 2H), 7.25-7.36(m, 2H), 7.45(d, 1H, J=7.6 Hz), 8.34-8.37(m, 1H), 11.36-11.39(m, 1H). MS m/z: 364.1(M + 2) |
| 16 | 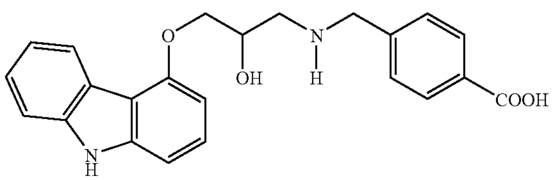 | $^1$H NMR(400 MHz, DMSO) δ (ppm): 2.50-2.70(m, 2H), 3.17(d, 2H, J=4.8 Hz), 4.10-4.40(m, 3H), 6.72(s, 1H), 7.10-7.25 (m, 4H), 7.30-7.50(m, 2H), 7.44(d, 1H, J=7.6 Hz), 7.90-8.40(m, 3H), 11.30-11.40(m, 1H). MS m/z: 392.2(M + 2) |
| 17 | 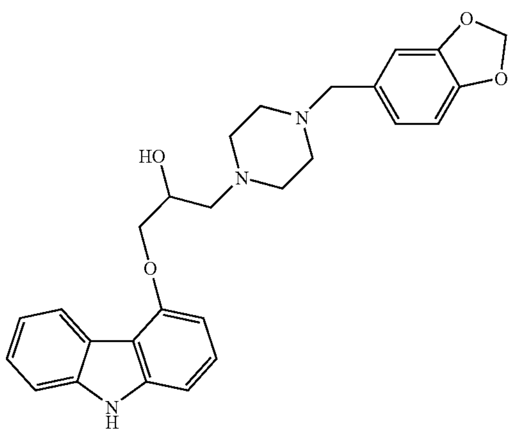 | $^1$H NMR(400 MHz, CDCl$_3$) δ (ppm): 2.40-2.70 (m, 6H), 2.75-2.90(m, 4H), 3.45(s, 1H), 4.20-4.25(m, 1H), 4.30-4.50(m, 2H), 5.94(s, 2H), 6.67(d, 1H, J=8.0 Hz), 6.75 (s, 2H), 6.86(s, 1H), 7.05(d, 1H, J=8.0 Hz), 7.25-7.50(m, 4H), 8.08(s, 1H), 8.26 (d, 1H, J=8.0 Hz). MS m/z: 460.0(M + 1) |
| 18 | 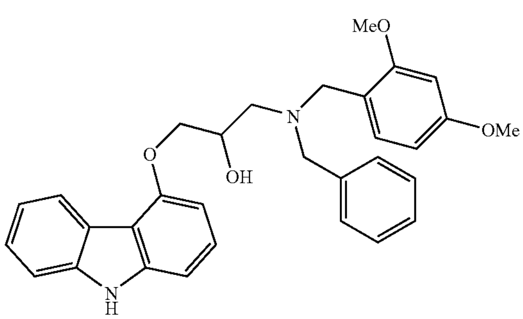 | $^1$H NMR(400 MHz, CDCl$_3$) δ (ppm): 2.75-2.90 (m, 2H), 3.50-3.75(m, 2H), 3.80-4.05 (m, 8H), 4.25-4.30(m, 3H), 6.40-6.60(m, 2H), 6.58(d, 1H, J=8.0 Hz), 7.02(d, 1H, J=8.0 Hz), 7.20-7.30(m, 8H), 7.40-7.50(m, 2H), 8.05(s, 1H), 8.17(d, 1H, J=8.0 Hz). MS m/z: 497.2(M + 1) |
| 19 | 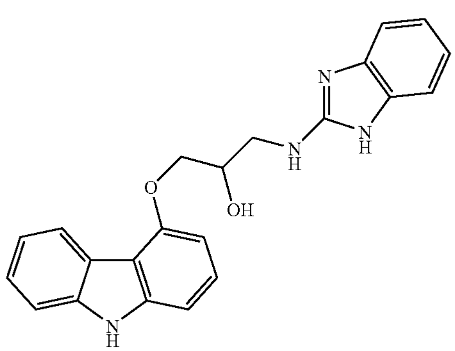 | $^1$H NMR(400 MHz, DMSO) δ (ppm): 4.10-4.50(m, 5H), 5.74(d, 1H, J=8.0 Hz), 6.47(s, 2H), 6.65(d, 1H, J=8.0 Hz), 6.83 (d, 1H, J=8.0 Hz), 6.94(s, 1H), 7.00-7.50 (m, 6H), 7.46(d, 1H, J=8.0 Hz), 8.32(d, 1H, J=8.0 Hz), 11.28(s, 1H). MS m/z: 373.0(M + 1) |

-continued

| Example | Structure | Analytical data |
|---|---|---|
| 20 | (carbazole-O-CH2-CH(OH)-CH2-NH-thiadiazole-SH) | ¹H NMR(400 MHz, DMSO) δ (ppm): 3.25-3.39(m, 1H), 3.50-3.75(m, 1H), 4.10-4.40 (m, 3H), 5.68(d, 1H, J=8.0 Hz), 6.68 (d, 1H, J=8.0 Hz), 7.07(d, 1H, J=8.0 Hz), 7.20-7.30(m, 2H), 7.35-7.40(m, 3H), 7.44 (d, 1H, J=8.0 Hz), 8.19(d, 1H, J=7.6 Hz), 11.25(s, 1H). MS m/z: 373.0(M + 1) |
| 21 | (carbazole-O-CH2-CH(OH)-CH2-NH-pyrazole-furan) | ¹H NMR(400 MHz, DMSO) δ (ppm): 4.05-4.25(m, 5H), 5.28(s, 1H), 5.50-5.80 (m, 2H), 6.40-6.58(m, 2H), 6.64(d, 1H, J=8.0 Hz), 7.00-7.15(m, 2H), 7.20-7.40(m, 3H), 7.46(d, 1H, J=8.0 Hz), 7.60(s, 1H), 8.29(d, 1H, J=8.0 Hz), 11.25(s, 1H). MS m/z: 389.1(M + 1) |
| 22 | (carbazole-O-CH2-CH(OH)-CH2-NH-benzothiadiazole) | ¹H NMR(400 MHz, CDCl₃) δ (ppm): 3.60-3.75 (m, 1H), 3.80-3.90(m, 1H), 4.35-4.49 (m, 2H), 4.60-4.75(m, 1H), 6.51(d, 1H, J=7.6 Hz), 6.69(d, 1H, J=8.0 Hz), 7.10(d, 1H, J=8.0 Hz), 7.25-7.40(m, 3H), 7.45-7.50 (m, 3H), 8.19(s, 1H), 8.26(d, 1H, J=8.0 Hz). MS m/z: 391.1(M + 1) |
| 23 | (carbazole-O-CH2-CH(OH)-CH2-NH-CH2-phenyl) | ¹H NMR(400 MHz, CDCl₃) δ (ppm): 2.94-2.99 (m, 1H), 3.05-3.09(m, 1H), 3.84-3.92 (m, 2H), 4.23-4.32(m, 3H), 6.67(d, 1H, J=8.0 Hz), 7.06(d, 1H, J=2.4 Hz), 7.20-7.21 (m, 1H), 7.28-7.40(m, 8H), 8.09(s, 1H), 8.21(d, 1H, J=8.0 Hz). MS m/z: 347.2 (M + 1). |

The racemic mixture of example 1 consisted of two isomers in the ratio of 49.67:50.33 as observed in the HPLC. We have also synthesized as seen below, the individual isomers starting form optically active epichlorohydrin.

EXAMPLE: 24

Synthesis of (2R)-1-(9H-carbazol-4-yloxy)-3-[(2,4-dimethoxy-benzyl)amino]propan-2-ol

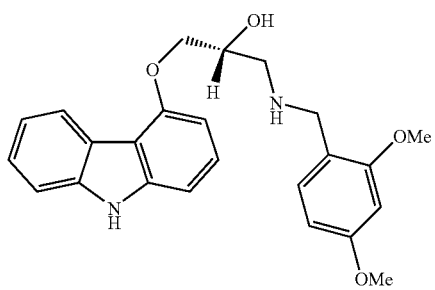

Step 1: Preparation of (R)-(−)-4-(2,3-epoxypropoxy)carbazole

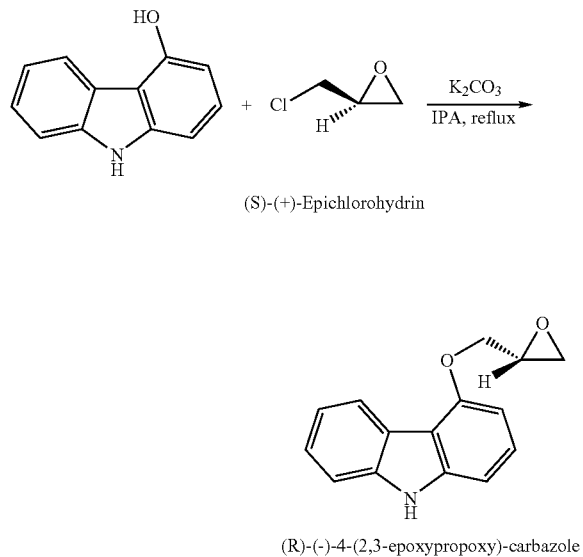

(S)-(+)-Epichlorohydrin (R)-(−)-4-(2,3-epoxypropoxy)-carbazole

To a solution of 4-Hydroxycarbazole (10.98 g, 0.06 mole) in IPA (60 mL) was added $K_2CO_3$ (20.73 g, 0.15 mole), followed by (S)-(+)-epichlorohydrin (7 ml, 0.09 mole) and the reaction mixture was slowly heated to 80-90° C. and then refluxed for 5 hours. Subsequently the reaction mixture was cooled to room temperature and filtered to remove the solid $K_2CO_3$, the filtrate was diluted with EtOAc (100 mL) and washed with water. The organic layer was dried over anhydrous $Na_2SO_4$, concentrated, and dried under vacuum to give a brown colored solid. The solid was dissolved in EtOAc (150 mL) and hexane was added to give a brown colored precipitate, the filtrate was decanted and the brown precipitate was again dissolved in EtOAc and precipitated with hexane. Finally the precipitate was filtered and the combined filtrate was evaporated to give a light brown colored solid, which was further purified by crystallization from EtOAc. The light brown colored crystals were collected; the filtrate was evaporated and further crystallized from EtOAc to give light brown crystals. This repeated crystallization process afforded the required compound as a light brown colored solid (7.1 g, 50%).

Chiral purity: 99.3%

SOR: −54.4 (pyridine)

Reported SOR: −63.4 (c=1; pyridine) (ref: U.S. Pat. No. 4,824,963)

0lp;3pStep 2

Preparation of (2R)-1-(9H-carbazol-4-yloxy)-3-[(2,4-dimethoxybenzyl)amino]propan-2-ol

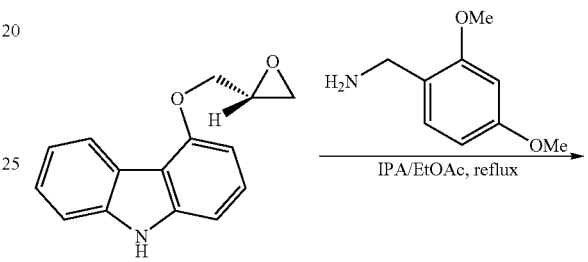

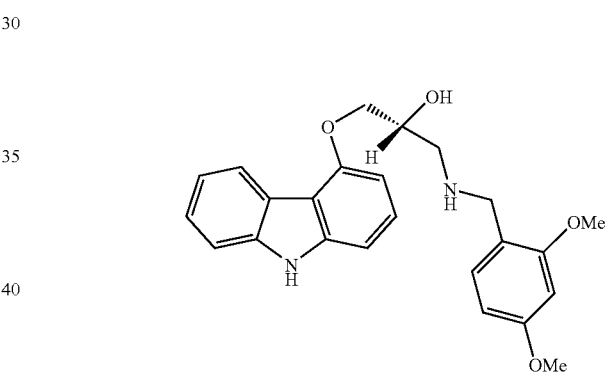

(R-isomer)

To a solution of (R)-(−)-4-(2,3-Epoxypropoxy)-carbazole (7 g, 0.029 mole) in EtOAc/IPA (40/80 mL) was added 2,4-dimethoxybenzylamine (8.7 mL, 0.058 mole) and the reaction mixture was slowly heated to 80-90° C. and then refluxed for 5 hours. Subsequently the reaction mixture was concentrated to half its volume, and cooled to room temperature to give a colorless solid. The solid was filtered, re-dissolved in EtOAc (60 mL) by refluxing, concentrated to 40 mL and the colorless precipitate formed on cooling to room temperature, was filtered and dried. Recrystallization of the residue obtained from the filtrate was repeated until maximum amount of the solid was recovered. The combined solid was triturated with diethylether by stirring for 6 hours, followed by filtration to afford 5.5 g (46% yield) of the desired compound as a colorless solid with m.p: 152-153° C. $^1H$ NMR (400 MHz, $CDCl_3$): δ 2.17 (s 1H), 2.86-2.92 (m, 1H), 2.99-3.02 (m, 1H), 3.74-3.86 (m, 8H), 4.18-4.32 (m, 3H), 6.38-6.44 (m, 2H), 6.67 (d, 1H, J=8.0 Hz), 7.04 (d, 1H, J=8.0 Hz), 7.12 (d, 1H, J=8.0 Hz), 7.18-7.41 (m, 4H), 8.09 (s, 1H), 8.21 (d, 1H, J=8.0 Hz). MS m/z: 407.1 (M+1). Chiral purity: 99.99%

EXAMPLE: 25

Synthesis of (2S)-1-(9H-carbazol-4-yloxy)-3-[(2,4-dimethoxybenzyl)amino]propan-2-ol

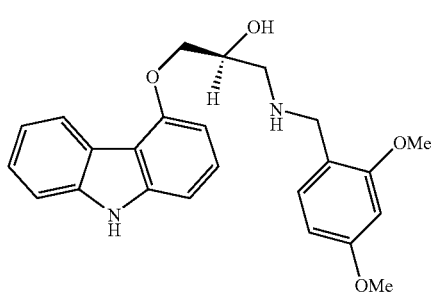

Step 1: Preparation of (S)-(−)-4-(2,3-epoxypropoxy)carbazole

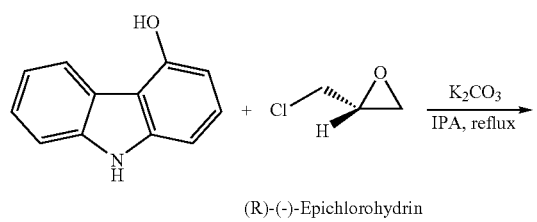

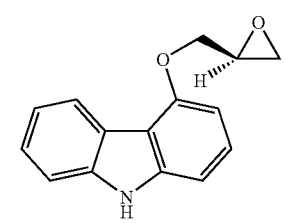

(S)-(+)-4-(2,3-epoxypropoxy)-carbazole

To a solution of 4-Hydroxycarbazole (10.98 g, 0.06 mole) dissolved in IPA (60 mL) was added $K_2CO_3$ (20.73 g, 0.15 mole), followed by (R)-(−)-epichlorohydrin (7 ml, 0.09 mole) and the reaction mixture was slowly heated to 80-90° C. and then refluxed for 5 hours. Subsequently the reaction mixture was cooled to room temperature, worked up and purified following the procedure similar to one described in step I for the synthesis of example 23, to afford the desired compound as a light brown colored solid (7.56 g, 53%).

Step 2: Preparation of (2S)-1-(9H-carbazol-4-yloxy)-3-[(2,4-dimethoxybenzyl)amino]propan-2-ol

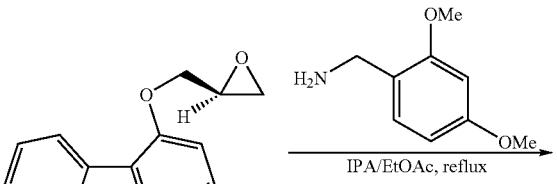

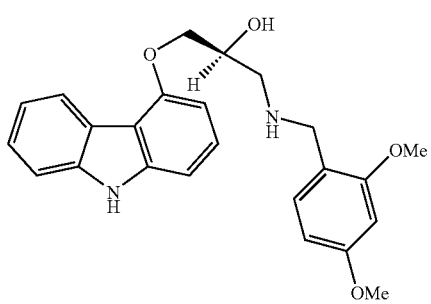

(S-isomer)

To a solution of (S)-(+)-4-(2,3-Epoxypropoxy)-carbazole (7.56 g, 0.031 mole) in EtOAc/IPA (40/80 mL) was added 2,4-dimethoxybenzylamine (9.48 mL, 0.063 mole) and the reaction mixture was slowly heated to 80-90° C. and then refluxed for 5 hours. Subsequently the reaction mixture was cooled to room temperature and purified following the procedure similar to one described in step 11 for the synthesis of example 23, to afford the desired compound as colorless solid (6 g, 48%) with m.p: 152-154° C. $^1$H NMR (400 MHz, $CDCl_3$): δ 2.17 (s 1H), 2.88-2.92 (m, 1H), 2.98-3.00 (m, 1H), 3.74-3.87 (m, 8H), 4.18-4.32 (m, 3H), 6.38-6.45 (m, 2H), 6.67 (d, 1H, J=8.0 Hz), 7.05 (d, 1H, J=8.0 Hz), 7.12 (d, 1H, J=8.0 Hz), 7.18-7.40 (m, 4H), 8.08 (s, 1H), 8.21 (d, 1H, J=8.0 Hz). MS m/z: 407.1 (M+1). Chiral purity: 99.96%

EXAMPLE: 26

Synthesis of 1-(9H-carbazol-4-yloxy)-3-{4-[(5-nitro-2-furyl)methyl]piperazin-1-yl}propan-2-ol

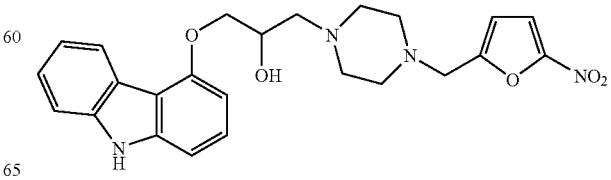

Step 1: Preparation of 3-[(4-Benzylpiperazin-1-yl)]-1-(9H-carbazol-4-yloxy)propan-2-ol

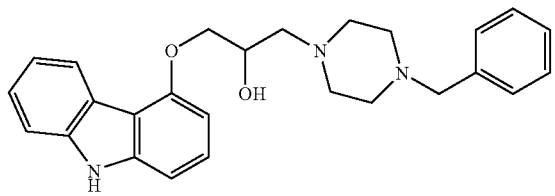

To a solution of 4-(2,3-Epoxypropoxy)-carbazole (5 g, 21 mmol) in THF (25 mL) at room temperature was added N-benzyl piperazine (5.5 g, 31.3 mmol), and the reaction mixture was stirred under reflux. After 12 hours, the reaction mass was cooled to room temperature, diluted with ethyl acetate (200 mL), washed with water and brine solution. The organic layer was dried over anhydrous $Na_2SO_4$ and concentrated to afford the crude compound as a light brown colored paste. Diisopropyl ether (100 mL) was added to the crude compound, which was stirred at room temperature, and then filtered to afford a off-white solid, which was further washed with isopropyl ether (3×50 mL) at 40° C. to afford 8.0 g (92% yield) of the desired compound as a colorless solid.

Step 2: Preparation of 1-(9H-carbazol-4-yloxy)-3-piperazin-1-ylpropan-2-ol

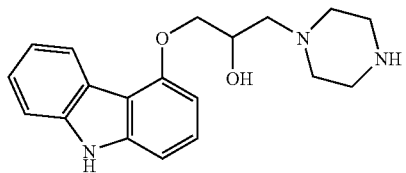

To a solution of 3-[(4-Benzylpiperazin-1-yl)]-1-(9H-carbazol-4-yloxy)propan-2-ol (prepared by following the procedure described in step I, example 26, 8.0 g, 19.3 mmol) in methanol (100 mL) was added 10% Pd/C (1.6 g) in a 500 mL Parr shaker flask. The flask was evacuated and 40 psi of $H_2$ pressure was applied and shaken for 8 hours. The reaction mixture was filtered on a celite bed (2.0 g) and resulting solution was concentrated to afford the crude compound as colorless paste. The crude compound was stirred with hexane (100 mL) at room temperature, decanted and similarly triturated with isopropyl alcohol (3×50 mL), followed by diethyl ether (2×50 mL), to afford 5.5 g (88% yield) of the title compound as a colorless solid.

Step 3
Preparation of 1-(9H-carbazol-4-yloxy)-3-{4-[(5-nitro-2 furyl)methyl]pipera-zin-1-yl}propan-2-ol

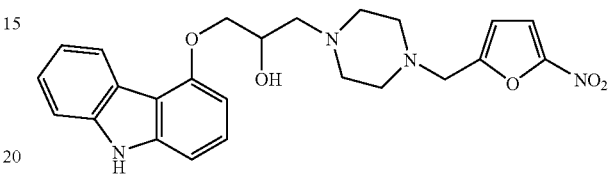

To a mixture of 1-(9H-carbazol-4-yloxy)-3-piperazin-1-yl propan-2-ol (0.5 g 1.54 mmol) in THF (10 mL), was added 2-3 drops of glacial acetic acid, followed by 5-nitrofurfural (0.325 g, 2.3 mmol). To the above solution $Na(OAc)_3BH$ (0.98 g, 4.6 mmol) was added carefully at room temperature and the reaction mixture was stirred at room temperature for 6 hours. Subsequently the reaction mixture was diluted with dichloromethane (50 mL), washed with water and brine solution. The organic layer was dried over anhydrous $Na_2SO_4$, concentrated, and purified by silica gel column chromatography using dichloromethane/MeOH (9:1) to afford the title compound as a yellow colored solid (0.2 g, 29% yield) with m.p.: 54-59° C. $^1H$ NMR (400 MHz, $CDCl_3$): δ 2.40-2.65 (m, 6H), 2.70-2.80 (m, 4H), 3.67 (s, 2H), 4.20-4.25 (m, 1H), 4.27-4.34 (m, 2H) 6.49 (d, 1H, J=3.6 Hz), 6.67 (d, 1H, J=8.0 Hz), 7.06 (d, 1H, J=8.0 Hz), 7.20-7.50 (m, 5H), 8.27 (s, 1H), and 8.30 (d, 1H, J=8 Hz). MS m/z: 451 (M+1).

Following Compounds were Prepared According to the Procedure Given in Example 26.

| 27 | 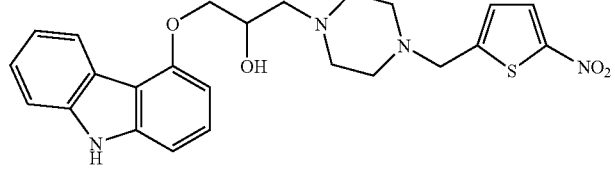 | $^1H$ NMR(400 MHz, $CDCl_3$) δ (ppm): 2.20-2.50 (m, 6H), 2.52-2.82(m, 4H), 3.72(s, 2H), 4.20-4.36(m, 3H), 6.67(d, 1H, J=8.0 Hz), 6.87(d, 1H, J=2.4 Hz), 7.06(d, 1H, J=8.0 Hz), 7.20-7.41(m, 4H), 7.80(d, 1H, J=4.0 Hz), 8.10(s, 1H), and 8.26(d, 1H, J=8.0 Hz). MS m/z: 466.9($M^+$). |
|---|---|---|
|  | m.p.: 70-75° C. |  |
| 28 | 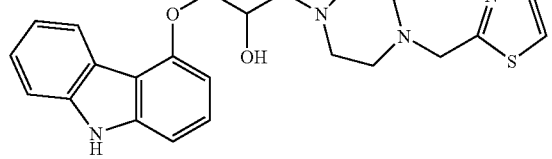 | $^1H$ NMR(400 MHz, $CDCl_3$) δ (ppm): 2.60-3.00 (m, 10H), 3.92(s, 2H), 4.20-4.24(m, 1H), 4.32-4.36(m, 3H), 6.68(d, 1H, J=8.0 Hz), 7.07(d, 1H, J=8.0 Hz), 7.20-7.44(m, 5H), 7.73(d, 1H, J=3.2 Hz), 8.12(s, 1H), and 8.24(d, 1H, J=8.0 Hz). MS m/z: 422.8($M^+$). |
|  | m.p.: 57-62° C. |  |

| | | |
|---|---|---|
| 29 | 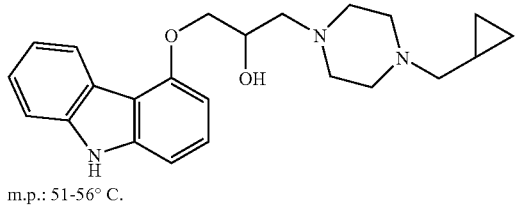<br>m.p.: 51-56° C. | $^1$H NMR(400 MHz, CDCl$_3$) δ (ppm): 0.15-0.35 (m, 2H), 0.60(d, 2H, J=8.0 Hz), 1.43 (s, 1H), 2.05(s, 2H), 2.47(d, 2H, J=8.0 Hz), 2.51-3.30(m, 8H), (t, 1H, J=6.0 Hz), 4.29 (t, 1H, J=4.0 Hz), 4.37 (t, 1H, J=8.0 Hz), 6.67(d, 1H, J=8.0 Hz), 7.07(d, 1H, J=8.0 Hz), 7.20-7.50(m, 4H), 8.16(s, 1H), and 8.24(d, 2H, J=8.0 Hz). MS m/z: 380.1(M$^+$). |
| 30 | 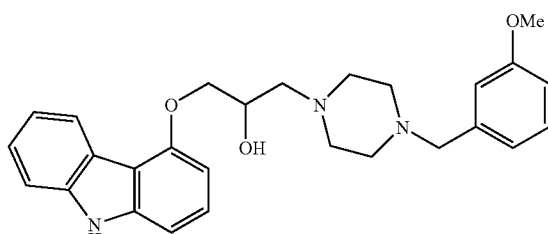<br>m.p.: 64-69° C. | $^1$H NMR(400 MHz, DMSO-d$_6$) δ (ppm): 2.40-3.10(m, 10H), 3.70-3.73(m, 6H), 3.81 (s, 2H), 4.00-4.30(m, 3H), 6.20-6.60(m, 2H), 6.68(d, 1H, J=8.0 Hz), 6.83(d, 1H, J=2.0 Hz), 6.90-7.20(m, 1H), 7.25-7.40(m, 2H), 7.44(d, 1H, J=8.0 Hz), 8.23(d, J=8.0 Hz), 9.92(s, 1H), and 11.29(s, 1H). MS m/z: 476.4(M + 1). |
| 31 | 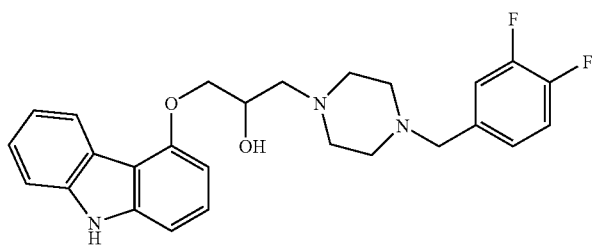<br>m.p.: 50-55° C. | $^1$H NMR(400 MHz, CDCl$_3$) δ (ppm): 2.05 (d, 2H, J=8.0 Hz), 2.40-2.80(m, 4H), 2.80-3.30 (m, 4H), 3.47(s, 2H), 5.20-5.75(m, 3H), 6.62(d, 2H, J=2.0 Hz), 6.90-7.50(m, 7H), 8.18(d, 1H, J=8.0 Hz), 8.30(s, 1H), and 9.92(s, 1H). MS m/z: 452.0(M + 1). |
| 32 | 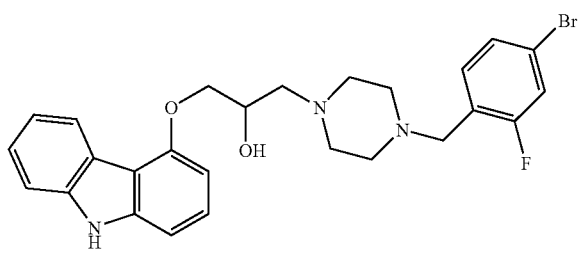<br>m.p.: 68-70° C. | $^1$H NMR(400 MHz, DMSO) δ (ppm): 1.20-1.40 (m, 2H), 2.25-2.75(m, 6H), 3.20-3.70 (m, 6H), 4.00-4.25(m, 3H), 4.50(s, 1H), 6.67(d, 1H, J=8.0 Hz), 8.21(d, 1H, J=8.0 Hz), 11.25(s, 1H). MS m/z: 513.1(M + 1). |
| 33 | 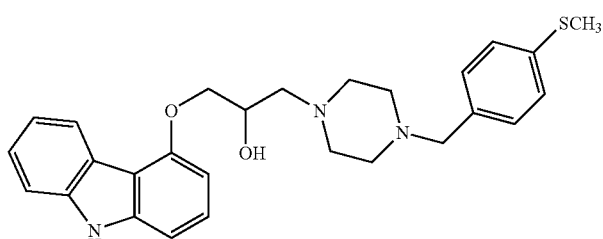<br>m.p.: 69-71° C. | $^1$H NMR(400 MHz, DMSO) δ (ppm): 1.00-1.25 (m, 2H), 2.25-2.90(m, 7H), 3.30-3.75 (m, 6H), 4.10-4.30(m, 3H), 5.00(s, 1H), 6.67(d, 1H, J=8.0 Hz), 7.06(d, 1H, J=8.0 Hz), 7.10-7.25(m, 1H), 7.26-7.40(m, 6H), 7.44(d, 1H, J=8.0 Hz), 8.22(d, 1H, J=8.0 Hz), 11.25(s, 1H). MS m/z: 462.2(M + 1). |
| 34 | 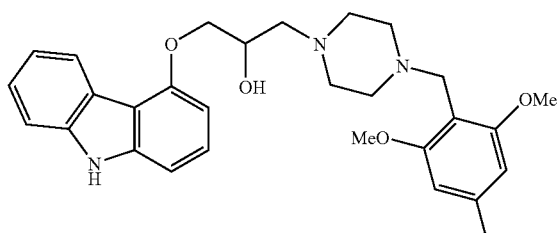<br>m.p.: 119-122° C. | $^1$H NMR(400 MHz, CDCl$_3$) δ (ppm): 2.50-3.20 (m, 8H), 3.30-3.60(m, 2H), 3.83(s, 9H), 4.10-4.40(m, 5H), 6.13(s, 2H), 6.62 (d, 1H, J=8.0 Hz), 7.08(d, 1H, J=8.0 Hz), 7.20-7.60(m, 3H), 8.18(d, 1H, J=8.0 Hz), 8.32(s, 1H), 11.20(s, 1H). MS m/z: 506.2(M + 1). |

EXAMPLE: 35

Synthesis of 1-(9H-carbazol-4-yloxy)-3-{4-(5-nitro-2-furoyl)piperazin-1-yl}propan-2-ol

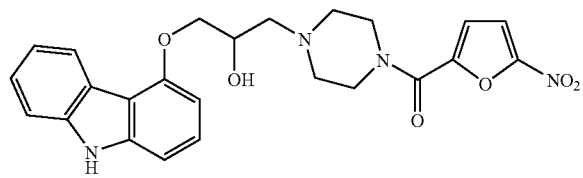

To a solution of 5-Nitrofuroic acid (1.56 g, 9.9 mmol) in DMF (30 mL) was added DIPEA (4.3 mL, 24.8 mmol), EDCI (3.18 g, 16.5 mmol), HOBt (0.44 g, 3.3 mmol) followed by the 1-(9H-carbazol-4-yloxy)-3-piperazin-1-ylpropan-2-ol (2.7 g, 8.3 mmol, prepared following the procedure described above in step 11, example 26). The reaction mixture was stirred at room temperature for 12 hours and was diluted with DCM (100 mL), washed with water and brine solution. The organic layer was dried on anhydrous $Na_2SO_4$, concentrated and purified by silica gel column chromatography, using hexane/EtOAc (4:6) to afford the title compound as yellow colored solid (2.0 g, 51% yield) with m.p: 178-181° C. $^1$H NMR (400 MHz, DMSO): δ 2.30-2.60 (m, 4H), 2.67-2.69 (m, 2H), 3.63-3.69 (m, 4H), 4.13-4.21 (m, 3H), 5.08 (s, 1H), 6.69 (d, 1H, J=8.0 Hz), 7.06 (d, 1H, J=8.0 Hz), 7.14 (t, 1H, J=8.0 Hz), 7.24-7.36 (m, 3H), 7.44 (d, 1H, J=8.0 Hz), 7.66 (d, 1H, J=4.0 Hz), 8.22 (d, 1H, 8.0 Hz), and 11.25 (s, 1H). MS m/z: 464.8 (M+1).

Following Compounds were Prepared According to the Procedure Given in Example 35

| Example | Structure | Analytical data |
|---|---|---|
| 36 | m.p.: 140-144° C. | $^1$H NMR(400 MHz, DMSO-$d_6$) δ (ppm): 2.51-2.53(m, 4H), 3.34(s, 2H), 3.67(s, 3H), 4.10-4.22(m, 4H), 5.20(s, 1H), 6.69 (d, 1H, J=8.0 Hz), 7.07(d, 1H, J=8.0 Hz), 7.15(d, 1H, J=8.0 Hz), 7.20-7.50(m, 4H), 8.23(d, 1H, J=8.0 Hz), and 11.25(s, 1H). MS m/z: 465.1(M + 1). |
| 37 | m.p.: 85.1-89.1° C. | $^1$H NMR(400 MHz, CDCl$_3$) δ (ppm): 2.58-2.63 (m, 2H), 2.70-2.82(m, 4H), 3.75-4.05 (m, 4H), 4.20-4.40(m, 3H), 6.50(s, 1H), 6.68(d 1H J=8.0 Hz), 7.02(d, 1H, J=3.2 Hz), 7.07(d, 1H, J=8.0 Hz), 7.20-7.45(m, 4H), 7.49(s, 1H), 8.14(s, 1H), and 8.26(d, 1H, J=8.0 Hz). MS m/z: 420.4(M + 1). |
| 38 | m.p.: 215-218° C. | $^1$H NMR(400 MHz, DMSO-$d_6$): δ 2.51-2.57 (m, 4H), 2.58-2.60(m, 2H), 3.60-3.80 (m, 4H), 4.05-4.25(m, 3H), 5.09(s, 1H), 6.70(d, 1H J=8.0 HZ), 6.78(d, 1H, J=8.0 Hz), 7.00-7.08(m, 2H), 7.13-7.19(m, 2H), 7.25-7.34(m, 2H), 7.40-7.44(m, 2H), 7.60 (d, 1H, J=8.0 Hz), 8.24(d, 1H, J=8.0 Hz), 11.25(s, 1H), and 11.57(s, 1H). MS m/z: 469.1(M + 1). |
| 39 | m.p.: 80-83° C. | $^1$H NMR(400 MHz, CDCl$_3$) δ (ppm): 2.59 (d, 2H, J=4.8 Hz), 2.70-2.90(m, 4H), 3.35 (s, 1H), 3.70-3.90(m, 4H), 4.20-4.40(m, 3H), 6.69(d, 1H, J=8.0 Hz), 6.60-7.20(m, 2H), 7.21-7.50(m, 6H), 8.12(s, 1H), and 8.25(d, 1H, J=8.0 Hz). MS m/z: 436.1 (M + 1). |

| Example | Structure | Analytical data |
|---|---|---|
| 40 | (carbazol-4-yloxy-2-hydroxypropyl piperazine, N-acyl with 5-(4-nitrophenyl)furan-2-yl)<br>m.p.: 101-104° C. | $^1$H NMR(400 MHz, CDCl$_3$) δ (ppm): 2.51-2.70 (m, 2H), 2.75-2.90(m, 4H), 3.75-4.20 (m, 4H), 4.25-4.50 (m, 3H), 6.69(d, 1H, J=8.0 Hz), 6.94(d, 1H, J=4.0 Hz), 7.05-7.20 (m, 2H), 7.21-7.50(m, 4H), 7.81(d, 2H, J=8.0 Hz), 8.15(s, 1H), and 8.20-8.40(m, 3H). MS m/z: 541.1(M + 1). |
| 41 | (carbazol-4-yloxy-2-hydroxypropyl piperazine, N-acyl with pyrazinyl) | $^1$H NMR(400 MHz, DMSO-d$_6$) δ (ppm): 2.40-2.80 (m, 6H), 3.50-3.80(m, 4H), 3.90-4.30 (m, 3H), 5.15(s, 1H), 6.62(s, 1H), 6.69(d, 1H, J=8.0 Hz), 6.98(s, 1H), 7.06 (d, 1H, J=8.0 Hz), 7.11-7.17(m, 1H), 7.20-7.40 (m, 2H), 7.44(d, 1H, J=8.0 Hz), 7.83 (s, 1H), 8.23(d, 1H J=8.0 Hz), and 11.26 (s, 1H). MS m/z: 432.1(M$^+$ + 1). |
| 42 | (carbazol-4-yloxy-2-hydroxypropyl piperazine, N-acyl with 3,4-dimethoxyphenyl)<br>m.p.: 98-101° C. | $^1$H NMR(400 MHz, CDCl$_3$) δ (ppm): 2.40-2.65 (m, 4H), 2.74-2.75(m, 4H), 3.68-3.72 (m, 2H), 3.90-3.91(m, 6H), 4.23-4.40(m, 3H), 6.68(d, 1H, J=8.0 Hz), 6.86(d, 1H, J=8.0 Hz), 6.98-7.00(m, 2H), 7.06(d, 1H, J=8.0 Hz), 7.20-7.40 (m, 4H), 8.13(s, 1H), and 8.25(d, 1H, J=8.0 Hz). MS m/z: 490.0 (M$^+$ + 1). |
| 43 | (carbazol-4-yloxy-2-hydroxypropyl piperazine, N-acyl with 4-methoxyphenylacetyl)<br>m.p.: 166-169° C. | $^1$H NMR(400 MHz, CDCl$_3$) δ (ppm): 2.34-2.37 (m, 1H), 2.45-2.55(m, 3H), 2.60-2.73 (m, 3H), 3.49(s, 4H), 3.67-3.72(m, 3H), 3.79(s, 3H), 4.20-4.30(m, 3H), 6.66(d, 1H, J=8.0 Hz), 6.86(d, 1H, J=8.0 Hz), 7.06 (d, 1H, J=8.0 Hz), 7.12-7.43(m, 6H), 8.13 (s, 1H), and 8.22(d, 1H, J=8.0 Hz). MS m/z: 474.0(M$^+$). |
| 44 | (carbazol-4-yloxy-2-hydroxypropyl piperazine, N-acyl with pentafluorophenylacetyl)<br>m.p.: 93-96° C. | $^1$H NMR(400 MHz, CDCl$_3$) δ (ppm): 2.45-2.70 (m, 2H), 2.73-2.82(m, 4H), 3.60-3.65 (m, 6H), 4.25-4.40(m, 3H), 6.69(d, 1H, J=8.0 Hz), 7.07(d, 1H, J=8.0 Hz), 7.20-7.45 (m, 4H), 8.11(s, 1H), and 8.25(d, 1H, J=8.0 Hz). MS m/z: 533.9(M$^+$). |
| 45 | (carbazol-4-yloxy-2-hydroxypropyl piperazine, N-acyl with 3,4-methylenedioxycinnamoyl)<br>m.p.: 90-93° C. | $^1$H NMR(400 MHz, CDCl$_3$) δ (ppm): 2.40-2.65 (m, 2H), 2.75-2.90(m, 4H), 3.65-3.95 (m, 4H), 4.23-4.40(m, 3H), 6.00(s, 2H), 6.65-6.75(m, 2H), 6.80(d, 1H, J=8.0 Hz), 6.98-7.10(m, 3H), 7.23-7.42(m, 4H), 7.61 (d, 1H, J=16.0 Hz), 8.13(s, 1H), and 8.26 (d, 1H, J=8.0 Hz). MS m/z: 499.9(M$^+$). |
| 46 | (carbazol-4-yloxy-2-hydroxypropyl piperazine, N-acyl with quinoxalin-2-yl)<br>m.p.: 89-92° C. | $^1$H NMR(400 MHz, CDCl$_3$) δ (ppm): 2.60-3.00 (m, 6H), 3.80-4.10(m, 4H), 4.20-4.45 (m, 3H), 6.69(d, 1H, J=8.0 Hz), 7.07(d, 1H, J=8.0 Hz), 7.23-7.41(m, 4H), 7.80-7.87 (m, 2H), 8.00-8.16(m, 3H), 8.25(d, 1H, J=8.0 Hz), and 9.20(s, 1H). MS m/z: 481.9(M$^+$). |

| Example | Structure | Analytical data |
|---|---|---|
| 47 | (carbazole-O-CH2-CH(OH)-CH2-N(piperazine)-C(=O)-pyridine-CN); m.p.: 92-95° C. | $^1$H NMR(400 MHz, CDCl$_3$) δ (ppm): 2.54-2.86 (m, 6H), 3.21(s, 1H), 3.45(s, 2H), 3.84-3.90 (m, 2H), 4.22-4.37 (m, 3H), 6.68 (d, 1H, J=8.0 Hz), 7.07(d, 1H, J=8.0 Hz), 7.20-7.45(m, 4H), 7.77(d, 1H, J=8.0 Hz), 7.85-7.91(m, 1H), 8.10(s, 1H), 8.22(d, 1H, J=8.0 Hz), and 8.75(s, 1H). MS m/z: 455.9(M$^+$). |
| 49 | (carbazole-O-CH2-CH(OH)-CH2-N(piperazine)-C(=O)-CH2-pyridine); m.p.: 62-65° C. | $^1$H NMR(400 MHz, CDCl$_3$) δ (ppm): 2.35-2.80 (m, 6H), 3.45-3.64(m, 2H), 3.66-3.75 (m, 4H), 4.20-4.32(m, 3H), 6.66(d, 1H, J=8.0 Hz), 7.05(d, 1H, J=8.0 Hz), 7.20-7.41 (m, 5H), 7.60-7.63(m, 1H), 8.20-8.25(m, 2H), and 8.47-8.54(m, 2H). MS m/z: 445.0 (M$^+$). |
| 49 | (carbazole-O-CH2-CH(OH)-CH2-N(piperazine)-C(=O)-CH2-thiophene) | $^1$H NMR(400 MHz, DMSO-d$_6$) δ (ppm): 2.35-2.65(m, 4H), 3.17-3.20(m, 2H), 3.30-3.50 (m, 6H), 4.10-4.20(m, 3H), 5.00(s, 1H), 6.70(d, 1H, J=8.0 Hz), 6.99(d, 1H J=8.0 Hz), 7.08(d, 1H, J=8.0 Hz), 7.12-7.50 (m, 6H), 8.23(d, 1H, J=8.0 Hz), 11.29(s, 1H). MS m/z: 450.5(M + 1). |
| 50 | (carbazole-O-CH2-CH(OH)-CH2-N(piperazine)-C(=O)-benzodioxole); m.p.: 70-73° C. | $^1$H NMR(400 MHz, CDCl$_3$) δ (ppm): 2.50-2.70 (m, 4H), 2.75-2.85(m, 4H), 3.50-3.80 (m, 4H), 4.25-4.40(m, 4H), 6.00(s, 2H), 6.67(d, 1H, J=8.0 Hz), 6.70-6.80(m, 1H), 6.85-7.10(m, 2H), 7.15-7.20(m, 1H), 7.25-7.50 (m, 4H), 8.18(s, 1H), 8.30-8.40(m, 2H), MS m/z: 474.1(M + 1). |
| 51 | (carbazole-O-CH2-CH(OH)-CH2-N(piperazine)-C(=O)-CH2CH2-indole); m.p.: 112-114° C. | $^1$H NMR(400 MHz, DMSO) δ (ppm): 2.25-2.60 (m, 4H), 2.65-2.80(m, 3H), 2.85-3.10 (m, 2H), 3.20(s, 1H), 3.25-3.60(m, 4H), 4.00-4.25(m, 3H), 5.10(s, 1H), 6.68(d, 1H, J=8.0 Hz), 6.80-7.25(m, 5H), 7.25-7.40 (m, 3H), 7.45-7.65(m, 2H), 8.21(d, 1H, J=8.0 Hz), 10.76(s, 1H), 11.23(s, 1H). MS m/z: 497.2(M + 1). |
| 52 | (carbazole-O-CH2-CH(OH)-CH2-N(piperazine)-C(=O)-fluoroindole); m.p.: 243-2466° C. | $^1$H NMR(400 MHz, DMSO) δ (ppm): 2.40-2.80 (m, 6H), 3.50-3.90(m, 4H), 4.10-4.40 (m, 3H), 5.07(d, 1H, J=4.0 Hz), 6.60-6.80 (m, 2H), 7.10-7.25(m, 3H), 7.26-7.60(m, 5H), 8.24(d, 1H, J=8.0 Hz). MS m/z: 486.5(M + 1). |

| Example | Structure | Analytical data |
|---|---|---|
| 53 | (structure) m.p.: 111-113° C. | $^1$H NMR(400 MHz, CDCl$_3$) δ (ppm): 2.30-2.60 (m, 2H), 2.70-2.90(m, 4H), 3.50(s, 1H), 3.70-3.90(m, 4H), 4.20-4.50(m, 3H), 5.30(s, 1H), 6.67(d, 1H, J=8.0 Hz), 6.75-7.20 (m, 4H), 7.25-7.50(m, 4H), 8.10(s, 1H), 8.23(d, 1H, J=8.0 Hz). MS m/z: 478.2(M + 1). |
| 54 | (structure) m.p.: 93-96° C. | $^1$H NMR(400 MHz, CDCl$_3$) δ (ppm): 2.80-3.30 (m, 6H), 4.00-4.50(m, 7H), 4.57(s, 1H), 6.64(d, 1H, J=8.0 Hz), 7.06(d, 1H, J=8.0 Hz), 7.20-7.50(m, 7H), 7.52(d, 1H, J=8.0 Hz), 7.67(d, 1H, J=8.0 Hz), 8.19(d, 1H, J=8.0 Hz). MS m/z: 470.1(M$^+$). |
| 55 | (structure) m.p.: 79-81° C. | $^1$H NMR(400 MHz, DMSO) δ (ppm): 2.25-2.60 (m, 4H), 2.65-2.70(m, 2H), 3.30-3.60 (m, 4H), 3.69(s, 2H), 4.10-4.25(m, 3H), 5.02(s, 1H), 6.68(d, 1H, J=8.0 Hz), 7.00-7.20 (m, 4H), 7.25-7.45(m, 3H), 7.44(d, 2H, J=8.0 Hz), 8.21(d, 1H, J=8.0 Hz), 11.24(s, 1H). MS m/z: 462.1(M$^+$). |
| 56 | (structure) m.p.: 78-80° C. | $^1$H NMR(400 MHz, CDCl$_3$) δ (ppm): 2.60-3.25 (m, 4H), 4.02-4.25(m, 4H), 4.30-4.75 (m, 3H), 4.89(s, 1H), 5.30(s, 1H0, 6.98-7.20 (m, 4H), 7.25-7.50(m, 3H), 8.10-8.20 (m, 2H), 12.60(s, 1H). MS m/z: 516.0 (M + 1). |
| 57 | (structure) | $^1$H NMR(400 MHz, DMSO) δ (ppm): 2.50-2.80 (m, 2H), 2.85-3.10(m, 4H), 3.15-3.25 (m, 2H), 3.30-3.75(m, 6H), 4.10-4.30(m, 3H), 6.72(d, 1H, J=8.0 Hz), 7.10-7.20(m, 2H), 7.25-7.39(m, 2H), 7.47(d, 1H, J=8.0 Hz), 8.24(d, 1H, J=7.6 Hz), 11.30(s, 1H). MS m/z: 397.2(M + 1). |

EXAMPLE: 58

Synthesis of 2-{4-[3-(9H-carbazol-4-yloxy)-2-hydroxypropyl]-piperazin-1-yl}-N-(5-methyl-1,3-thiazol-2-yl)acetamide

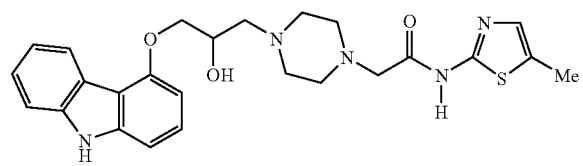

Step 1: Preparation of 2-bromo-N-(5-methyl-1,3-thiazol-2-yl)acetamide

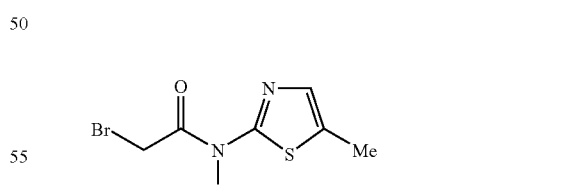

To a solution of 2-amino-5-methylthiazole (1 g, 8.75 mmol) in dichloromethane (56 mL) cooled to 0° C., was added bromoacetyl bromide (0.9 mL, 10.5 mmol) and TEA (1.83 mL, 13.1 mmol) dropwise, simultaneously and with stirring at same temperature for 1 hour. The reaction mixture was diluted with dichloromethane, washed with water and brine solution. The organic layer was dried over anhydrous Na$_2$SO$_4$ and concentrated to afford 1.6 g (78% yield) of crude compound as an off-white solid.

Step 2
Preparation of 2-{4-[3-(9H-carbazol-4-yloxy)-2 hydroxypropyl]piperazin-1-yl}-N-(5-methyl-1,3-thiazol-2-yl)acetamide

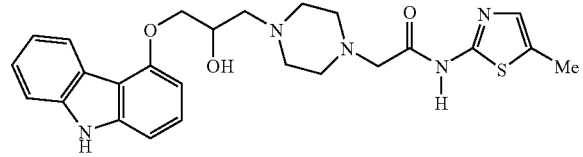

To a solution of 2-Bromo-N-(5-methyl-1,3-thiazol-2-yl)acetamide (prepared following the procedure described in step I, example 58, 0.2 g, 0.92 mmol) in THF (10 mL) was added NaI (0.06 g, 0.38 mmol), and the reaction mixture was stirred at room temperature for 1 hour, subsequently K$_2$CO$_3$ (0.05 g, 0.38 mmol) was added and stirring was continued further for 10-15 minutes. To the above solution, 1-(9H-carbazol-4-yloxy)-3-piperazin-1-ylpropan-2-ol (prepared following the procedure described in step 11, example 26, 0.25 g, 0.76 mmol) in THF (10 mL) was added dropwise, followed by TEA (0.32 mL, 2.3 mmol) and the above was stirred at room temperature for 3 hours. The reaction mixture was then concentrated and diluted with EtOAc (50 mL), washed with water and brine. The organic layer was dried over anhydrous Na$_2$SO$_4$, concentrated and purified by silica gel column chromatography, using dichloromethane/MeOH (9.2:0.8) to afford of the title compound as yellow colored hygroscopic solid (0.152 g, 42% yield). $^1$H NMR (400 MHz, CDCl$_3$): δ 2.42 (s, 3H), 2.51-3.00 (m, 10H), 3.26 (s, 2H), 4.23-4.36 (m, 3H), 6.68 (d, 1H, J=8.0 Hz), 7.06-7.10 (m, 2H), 7.27-7.42 (m, 3H), 8.20 (s, 1H), 8.26 (d, 1H, J=8.0 Hz), and 10.16 (s, 1H). MS m/z: 480.1 (M+1).

Following Compounds were Prepared According to the Procedure Given in Example 58.

| | | |
|---|---|---|
| 59 | 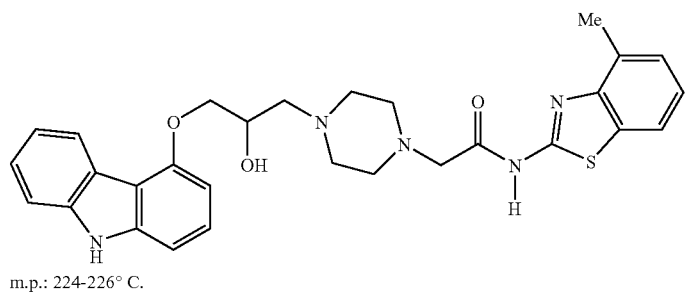 m.p.: 224-226° C. | $^1$H NMR(400 MHz, DMSO-d$_6$) δ (ppm): 2.40-2.80(m, 13H), 3.33(s, 2H), 4.10-4.25 (m, 3H) 4.98(s, 1H), 6.68(d, 1H, J=8.0 Hz), 7.06(d, 1H, J=8.0 Hz), 7.20-7.40(m, 5H), 7.43(d, 1H, J=2.0 Hz), 7.78(d, 1H, J=2.0 Hz), 8.23(d, 1H, J=8.0 Hz), 11.24(s, 1H), and 12.20(s, 1H). MS m/z: 530.2 (M + 1). |
| 60 | 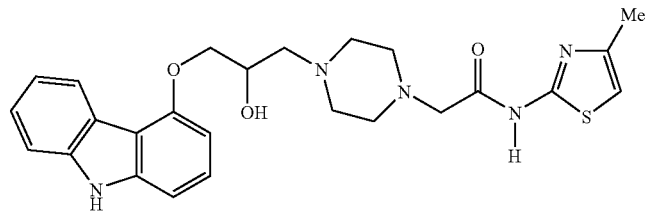 | $^1$H NMR(400 MHz, CD$_3$OD) δ (ppm): 2.31 (s, 3H), 2.80-3.20(m, 4H), 3.20-3.60(m, 8H), 4.20-4.40(m, 3H), 4.50-4.70 (brs, 1H), 6.68-6.72(m, 2H), 7.08(d, 1H, J=8.0 Hz), 7.15(s, 1H), 7.70-7.80(m, 3H), 7.40(s, 1H), and 8.28(d, 1H, J=8.0 Hz). MS m/z: 480.2(M + 1). |
| 61 | 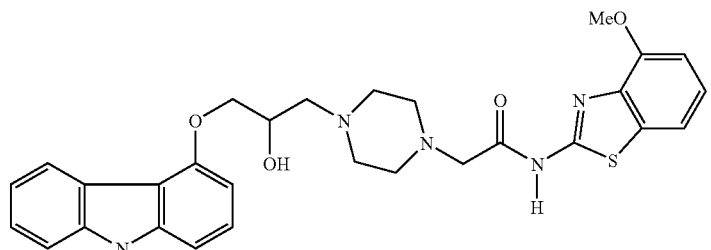 m.p.: 289-292° C. | $^1$H NMR(400 MHz, DMSO-d$_6$) δ (ppm): 2.90-3.25(m, 4H), 3.30-3.75(m, 8H), 3.91 (s, 3H), 4.22(s, 2H), 4.55(s, 1H), 6.08(s, 1H), 6.71(d, 1H, J=8.0 Hz), 7.01(d, 1H, J=8.0 Hz), 7.09-7.36(m, 5H), 7.46(d, 1H, J=8.0 Hz), 7.54(d, 1H, J=8.0 Hz), 11.30(s, 1H), and 12.31(s, 1H). MS m/z: 546.2 (M + 1). |
| 62 | 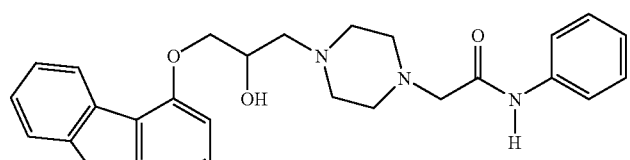 m.p.: 69-71° C. | $^1$H NMR(400 MHz, CDCl$_3$) δ (ppm): 2.50-2.90 (m, 10H), 3.17(s, 2H), 3.65(s, 1H), 4.20-4.40(m, 3H), 6.69(d, 1H, J=8.0 Hz), 6.90-7.20(m, 3H), 7.25-7.42(m, 5H), 7.58 (d, 2H, J=8.0 Hz), 8.13(s, 1H), 8.27(d, 1H, J=8.0 Hz), 9.09(s, 1H), 11.30(s, 1H), and 12.31(s, 1H). MS m/z: 459.2(M + 1). |

| | | |
|---|---|---|
| 63 | 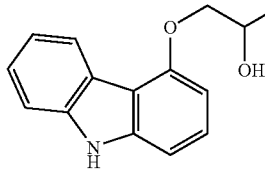 | ¹H NMR(400 MHz, CDCl₃) δ (ppm): 2.40-2.75 (m, 6H), 2.80-2.90(m, 6H), 2.95-3.20 (m, 2H), 3.60-4.10(m, 6H), 4.25-4.65(m, 3H), 6.25-6.50(m, 2H), 6.51-6.75(m, 1H), 7.00-7.50(m, 5H), 8.20-8.30(m, 1H), and 8.60(s, 1H). MS m/z: 533.2(M⁺). |

EXAMPLE: 64

Synthesis of 1-(9H-carbazol-4-yloxy)-3-{[1-(5-nitro-2-furoyl)piperidin-4-yl]amino}propan-2-ol

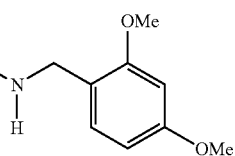

Step 1: Preparation of 3-[(1-benzylpiperidin-4-yl)amino]-1-(9H-carbazol-4-yloxy)pro-pan-2-ol

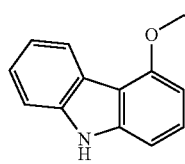

To a solution of 4-(2,3-Epoxypropoxy)-carbazole (1 g, 4.1 mmol) in THF (30 mL) cooled to 5-10° C., was added LiClO₄ (0.44 g, 4.1 mmol) and the reaction mixture was stirred for 15 minutes. 4-amino-1-benzylpiperidine (1.26 mL, 6.2 mmol) was added dropwise to the above reaction mixture at room temperature and stirring was continued for 12 hours. To the reaction mixture 50 mL of saturated NH₄Cl was added and stirring was continued for 5 minutes, subsequently the solution was extracted with dichloromethane (100 mL), washed with water and brine solution. The organic layer was dried over anhydrous Na₂SO₄ and concentrated to afford the crude compound as light brown colored paste. The crude compound was purified by silica gel column chromatography, using DCM/MeOH (7:3) to afford the title compound as pale yellow colored solid (1.2 g, 65% yield).

Step 2
Preparation of 1-(9H-carbazol-4-yloxy)-3-(piperidin-4-ylamino)propan-2-ol

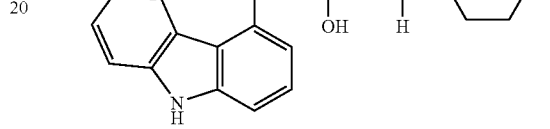

To a solution of 3-[(1-Benzylpiperidin-4-yl)amino]-1-(9H-carbazol-4-yloxy)propan-2-ol (prepared by following the procedure described in step I, example 64, 0.5 g, 1.16 mmol) in methanol (100 mL) was added 10% Pd/C (0.15 g) in a 500 mL Parr shaker flask. The flask was evacuated and 40 psi of H₂ pressure was applied and shaken for 10 hours. The reaction mixture was filtered on a celite bed (2.0 g) and resulting solution was concentrated to afford the crude compound as pale brown colored paste. The crude compound was triturated with hexane (2×20 mL), to afford the required compound as pale yellow colored solid (0.31 g, 87% yield).

Step 3
Preparation of 1-(9H-carbazol-4-yloxy)-3-{[1-(5-nitro-2-furoyl)piperidin-4-yl]amino}propan-2-ol

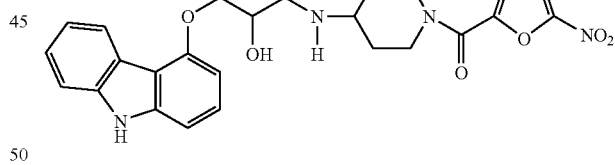

To a solution of 5-Nitrofuroic acid (0.14 g, 0.88 mmol) in DMF (6 mL) was added TEA (0.17 mL, 1.2 mmol), EDCI (0.2 g, 1.0 mmol), HOBt (0.031 g, 0.23 mmol), followed by 1-(9H-carbazol-4-yloxy)-3-(piperidin-4-ylamino)propan-2-ol (0.2 g, 0.6 mmol, prepared by following the procedure described in step 11, example 64). The reaction was stirred at room temperature for 12 hours and was diluted with DCM (25 mL), washed with water and brine solution. The organic layer was dried over anhydrous Na₂SO₄, concentrated and purified by silica gel column chromatography using DCM/MeOH (9.5:0.5) to afford the title compound as red colored paste (45 mg, 32% yield). ¹H NMR (400 MHz, DMSO): δ 1.20-1.80 (m, 3H), 1.90-2.30 (m, 2H), 2.50-3.60 (m, 6H), 4.00-4.60 (m, 3H), 6.72 (d, 1H, J=8.0 Hz), 6.90-7.60 (m, 6H), 7.77 (d, 1H, J=3.6 Hz), 8.22 (d, 1H, J=8.0 Hz), and 11.30 (s, 1H). MS m/z: 478.1 (M⁺).

Following Compounds were Prepared According to the Procedure Given in Example 64.

| 65 | 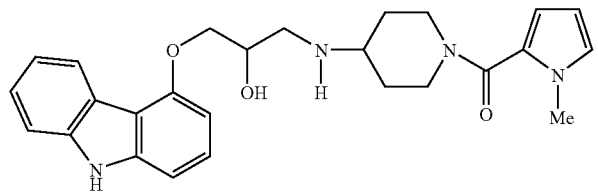 | $^1$H NMR(400 MHz, DMSO-d$_6$) δ (ppm): 1.00-1.40(m, 5H), 1.75-1.80(m, 2H), 2.80-2.90 (m, 2H), 2.95-3.10(m, 2H), 3.59(s, 3H), 4.10-4.20(m, 3H), 6.00(s, 1H), 6.22 (d, 1H, J=2.0 Hz), 6.68(d, 1H, J=8.0 Hz), 6.85(s, 1H), 7.00-7.15(m, 2H), 7.25-7.40 (m, 2H), 7.44(d, 1H, J=8.0 Hz), 8.21(d, 1H, J=8.0 Hz), and 11.26(s, 1H). MS m/z: 447.2(M + 1). |
|---|---|---|
| 66 | 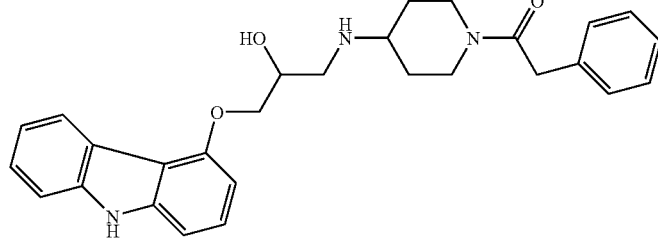<br>m.p.: 79-82° C. | $^1$H NMR(400 MHz, CDCl$_3$) δ (ppm): 0.84-0.89 (m, 1H), 1.00-1.35(m, 3H), 1.80-1.95 (m, 2H), 2.70-2.77(m, 2H), 2.90-3.15(m, 3H), 3.79(d, 1H, J=13.6 Hz), 4.20-4.30 (m, 3H), 4.46(d, 1H, J=13.6 Hz), 6.66(d, 1H, J=8.0 Hz), 6.95-7.20(m, 3H), 7.15-7.45 (m, 5H), 8.14(s, 1H), and 8.22(d, 1H, J=8.0 Hz). MS m/z: 475.2(M$^+$). |
| 67 | 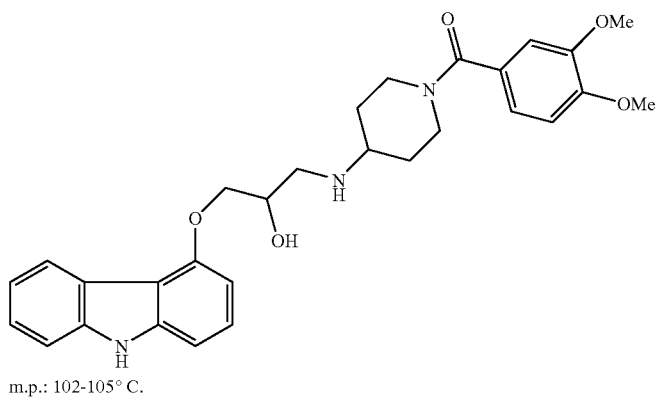<br>m.p.: 102-105° C. | $^1$H NMR(400 MHz, CDCl$_3$) δ (ppm): 1.25-1.60 (m, 2H), 1.80-2.15(m, 2H), 2.75-2.80 (m, 1H), 2.85-3.25(m, 6H), 3.85-3.95(m, 6H), 4.25-4.35(m, 3H), 6.68(d, 1H, J=8.0 Hz), 6.85(d, 1H, J=8.0 Hz), 6.96(d, 2H, J=8.0 Hz), 7.07(d, 1H, J=8.0 Hz), 7.20-7.45 (m, 4H), and 8.24(d, 1H, J=8.0 Hz). MS m/z: 404.0(M$^+$ + 1). |
| 68 | 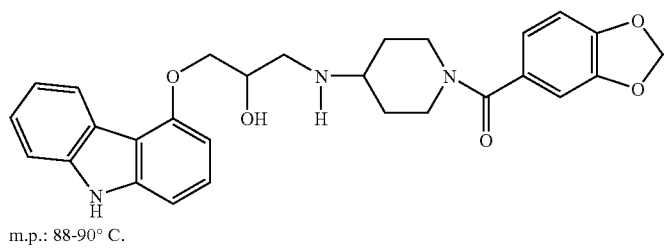<br>m.p.: 88-90° C. | $^1$H NMR(400 MHz, DMSO) δ (ppm): 1.20-1.40 (m, 3H), 1.75-2.20(m, 4H), 2.70-3.20 (m, 4H), 4.00-4.40(m, 4H), 6.07(s, 2H), 6.68(d, 1H, J=8.0 Hz), 6.70-7.10(m, 3H), 7.15-7.25(m, 2H), 7.30-7.45(m, 4H), 7.44 (d, 1H, J=8.0 Hz), 8.20(d, 1H, J=8.0 Hz), 11.24(d, 1H, J=8.0 Hz). MS m/z: 488.1 (M$^+$). |
| 69 | 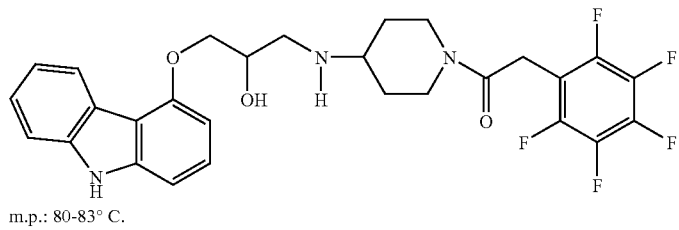<br>m.p.: 80-83° C. | $^1$H NMR(400 MHz, DMSO) δ (ppm): 1.90-2.25 (m, 2H), 2.50-2.75(m, 2H), 3.10-3.40 (m, 4H), 3.75-4.25(m, 3H), 4.30-4.50(m, 5H), 6.71(d, 1H, J=8.0 Hz), 7.00-7.25(m, 2H), 7.26-7.40(m, 2H), 7.46(d, 1H, J=8.0 Hz), 7.60-7.80(m, 2H), 8.21(d, 1H, J=8.0 Hz). MS m/z: 546.0(M − 1). |

| | | |
|---|---|---|
| 70 | 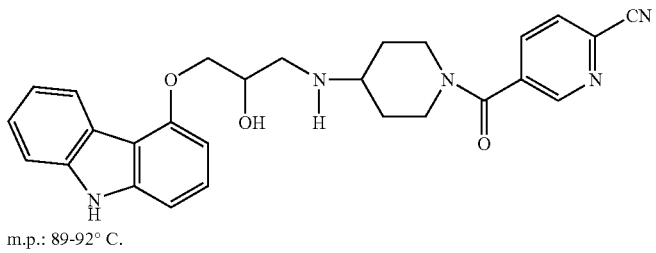 m.p.: 89-92° C. | ¹H NMR(400 MHz, DMSO) δ (ppm): 1.25-1.50 (m, 2H), 1.75-2.05(m, 2H), 2.70-2.90 (m, 2H), 3.00-3.25(m, 3H), 3.40-3.60(m, 1H), 4.10-4.40(m, 4H), 5.30(s, 1H), 6.68 (d, 1H, J=8.0 Hz), 7.00-7.25(m, 2H), 7.30-7.40 (m, 2H), 7.44(d, 1H, J=8.0 Hz), 8.05 (d, 1H, J=8.0 Hz), 8.07-8.14(m, 1H), 8.20 (d, 1H, J=8.0 Hz), 8.76(s, 1H), 11.25(s, 1H). MS m/z: 468.1(M − 1). |
| 71 | 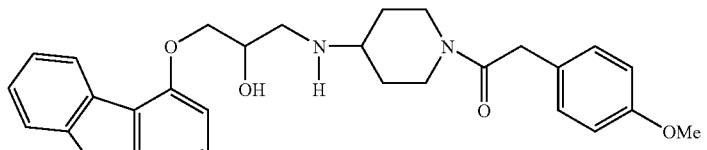 m.p.: 54-57° C. | ¹H NMR(400 MHz, DMSO) δ (ppm): 1.10-1.50 (m, 2H), 1.80-2.20(m, 2H), 2.25-2.40 (m, 1H), 2.50-2.80(m, 1H), 2.90-3.30(m, 3H), 3.50-3.90(m, 5H), 3.95-4.10(m, 1H), 4.20-4.60(m, 4H), 6.68(d, 1H, J=8.0 Hz), 6.86(d, 2H, J=8.0 Hz), 11.28(s, 1H). MS m/z: 486.1(M − 1). |

EXAMPLE: 72

Synthesis of N-[3-(9H-carbazol-4-yloxy)-2-hydroxypropyl]-3,4-dimethoxy-N-methylbenzamide

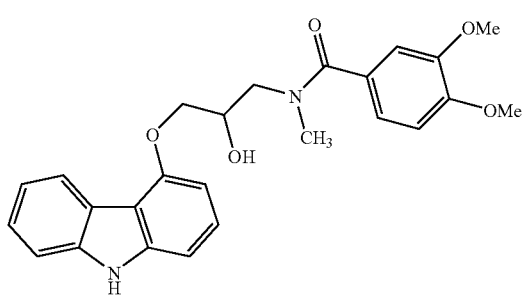

Step 1: Preparation of 1-(9H-carbazol-4-yloxy)-3-(methylamino)propan-2-ol

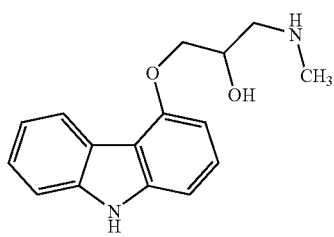

To a solution of 4-(2,3-Epoxypropoxy)carbazole (1 g, 4.18 mmol) in THF (10 mL) cooled to 0° C. was added LiClO₄ (0.445 g, 4.18 mmol) followed by 11% w/w of methylamine in THF (12 ml, 41.8 mmol) and the reaction mixture was stirred at room temperature for 12 hours. To the reaction mixture 30 mL of saturated NH₄Cl was added and was stirred for 5 minutes, then the solution was extracted with dichloromethane (100 mL), washed with water and brine solution. The organic layer was dried over anhydrous Na₂SO₄ and concentrated to afford (0.9 g, 80%) of the crude compound as pale yellow colored paste.

Step 2: Preparation of N-[3-(9H-carbazol-4-yloxy)-2-hydroxypropyl]-3,4-dimethoxy-N-methylbenzamide

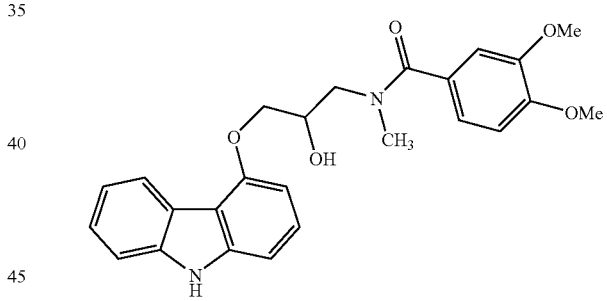

To a solution of 3,4-Dimethoxybenzoic acid (0.2 g, 1.11 mmol) in DMF (5 mL) was added DIPEA (0.48 mL, 2.8 mmol), EDCI (0.355 g, 1.85 mmol), HOBt (0.05 g, 0.37 mmol) followed by 1-(9H-carbazol-4-yloxy)-3-(methylamino)propan-2-ol (0.25 g, 0.925 mmol) prepared following the procedure described above in step I, example 72. The reaction was stirred at room temperature for 12 hours and was diluted with DCM (50 mL), washed with water and brine solution. The organic layer was dried over anhydrous Na₂SO₄, concentrated. The crude compound was purified by dissolution in dichloromethane (3 mL) and precipitation by adding diisopropyl ether (5 mL) and hexane (10 mL). The resulting white solid was filtered, and dried to afford the desired compound (0.15 g, 38%) with m.p.: 77-80° C. ¹H NMR (400 MHz, CDCl₃) δ (ppm): 3.10-3.40 (m, 3H), 3.70-4.10 (m, 7H), 4.07 (s, 1H), 4.20-4.25 (m, 1H), 4.38 (s, 1H), 4.56 (s, 1H), 4.76 (s, 1H), 6.74 (s, 1H), 6.87 (s, 1H), 6.90-7.15 (m, 4H), 7.20-7.49 (m, 3H), 8.17 (s, 1H), 8.30 (s, 1H). MS m/z: 435.0 (M⁺).

EXAMPLE: 73

Synthesis of 1-(9H-carbazol-4-yloxy)-3-[3,5-dimethoxybenzyl(methyl)amino]propan-2-ol

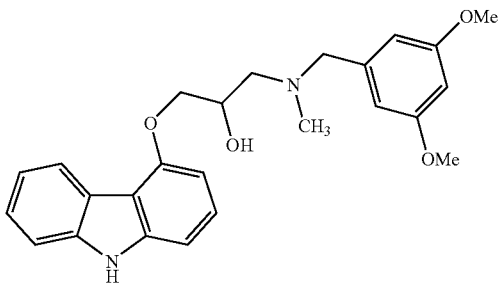

The reaction of 1-(9H-carbazol-4-yloxy)-3-(methylamino)propan-2-ol (0.20 g, 0.74 mmol) with 3,5-dimethoxybenzaldehyde (0.185 g, 1.11 mmol) in the presence of 2-3 drops of glacial acetic acid and Na(OAc)$_3$BH (0.157 g, 0.578 mmol) following the procedure similar to the one described in example 26, afforded the title compound as a brown colored paste (0.045 g, 13% yield) with $^1$H NMR (400 MHz, DMSO): δ 2.25(s, 3H), 3.40-3.60 (m, 2H), 3.51 (s, 2H), 3.65 (s, 6H), 4.10-4.13 (m, 1H), 4.15-4.25 (m, 2H), 5.00 (s, 1H), 6.31 (s, 1H), 6.49 (d, 2H, J=1.6 Hz), 6.67 (d, 1H, J=8.0 Hz), 7.05-7.12 (m, 2H), 7.25-7.35 (m, 2H), 7.43 (d, 1H, J=8 Hz), 8.17 (d, 1H, J=8.0 Hz), 11.23 (s, 1H). MS m/z: 421.0 (M+1).

EXAMPLE: 74

Synthesis of 1-(9H-carbazol-4-yloxy)-3-[4-(3-trifluoromethyl phenylsulfonyl)piperazin-1-yl]propan-2-ol

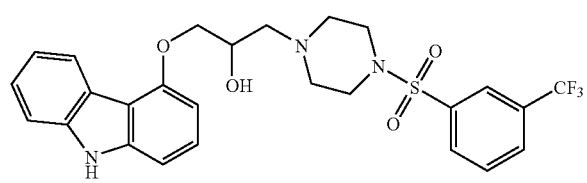

To a solution of 1-(9H-carbazol-4-yloxy)-3-piperazin-1-ylpropan-2-ol (0.2 g, 0.614 mmol) in DMF (4 mL), was added DIPEA (0.05 mL, 0.301 mmol) followed by the drop-wise addition of 3-trifluoromethylbenzenesulfonyl chloride (0.098 g, 0.61 mmol) at room temperature and the reaction mixture was stirred for 3 hours. Subsequently the reaction mixture was diluted with ethyl acetate (30 mL), washed with water and brine solution. The organic layer was dried on anhydrous Na$_2$SO$_4$, concentrated, and purified by precipitating the compound from dichloromethane by adding hexane, to give the required compound as a pale yellow colored solid (0.102 g, 30% yield). $^1$H NMR (400 MHz, DMSO): δ 2.30-2.90 (m, 6H), 3.00-3.30 (m, 4H), 4.00-4.30 (m, 4H), 5.00 (s, 1H), 6.61 (d, 1H, J=8 Hz), 7.00-7.20 (m, 2H), 7.25-7.40 (m, 2H), 7.42 (d, 1H, J=8.0 Hz), 7.80-8.00 (m, 2H), 8.06 (d, 1H, J=8 Hz), 8.20-8.30 (m, 2H), 11.26 (d, 1H, J=12 Hz). MS m/z: 534.1 (M+1).

Following Compounds were Prepared Following the Procedure Given in Example: 74

| Example | Structure | Analytical data |
|---|---|---|
| 75 | (carbazole-O-CH$_2$-CH(OH)-CH$_2$-N-piperazine-N-SO$_2$-C$_6$H$_4$-OAc); m.p.: 183-185° C. | $^1$H NMR(400 MHz, DMSO-d$_6$) δ (ppm): 2.40-2.80(m, 8H), 2.85-3.10(m, 4H), 4.07 (s, 3H), 4.98(s, 1H), 6.61(d, 1H, J=8.0 Hz), 7.00-7.20(m, 2H), 7.22(t, 1H, J=8.0 Hz), 7.31(t, 1H, J=8.0 Hz), 7.42(d, 1H, J=8.0 Hz), 7.86(d, 2H, J=8.0 Hz), 8.10-8.30 (m, 3H), 11.22(s, 1H). MS m/z: 508.1 (M$^+$). |

It is appreciated that in any of the above-mentioned reactions, any reactive group in the substrate molecule may be protected according to conventional chemical practice. Suitable protecting groups in any of the above-mentioned reactions are those used conventionally in the art. The methods of formation and removal of such protecting groups are those conventional methods appropriate to the molecule being protected. Protecting groups are removed under conditions, which will not affect the remaining portion of the molecule.

The pharmaceutically acceptable salts are prepared by reacting the compound of formula (I) with 1 to 10 equivalents of a base such as sodium hydroxide, sodium methoxide, sodium hydride, potassium t-butoxide, calcium hydroxide, magnesium hydroxide and the like, in solvents like ether, tetrahydrofuran, methanol, t-butanol, dioxane, isopropanol, ethanol etc. Mixture of solvents may be used. Organic bases such as diethanolamine, α-phenylethylamine, benzylamine, piperidine, morpholine, pyridine, hydroxyethylpyrrolidine, hydroxyethylpiperidine, choline, guanidine and the like, ammonium or substituted ammonium salts, aluminum salts. Amino acids such as glycine, alanine, cysteine, lysine, arginine, phenylalanine etc may be used for the preparation of amino acid salts. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid, oxalic acid and the like in solvents like ethyl acetate, ether, alcohols, acetone, tetrahydrofuran, dioxane etc. Mixture of solvents may also be used.

It should be noted that compounds of the invention may contain groups that may exist in tautomeric forms, and though one form is named, described, displayed and/or claimed herein, all the tauomeric forms are intended to be inherently included in such name, description, display and/or claim.

The stereoisomers of the compounds forming part of this invention may be prepared by using the reactants in their single enantiomeric form as has been the in the present case. 4-Hydroxycarbazole on treatment with (S)-(+)-epichlorohydrin furnished (R)-(−)-4-(2,3-epoxypropoxy)carbazole, which on reaction with the respective amine yielded the pure R isomer (example 24). Similarly use of the (R)-(−)-epichlorohydrin under similar conditions resulted in the S isomer (example 25).

The stereoisomers of the compounds can also be made by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or by using chiral bases such as brucine, cinchona alkaloids, their derivatives and the like. Commonly used methods are compiled by Jaques et al in "Enantiomers, Racemates and Resolution" (Wiley Interscience, 1981).

Prodrugs of the compounds of formula (I) are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art.

Various polymorphs of the compounds of the general formula (I), forming part of this invention may be prepared by crystallization of the compounds of formula (I) under different conditions. For example, using different commonly used solvents, or their mixtures for recrystallization; crystallizations at different temperatures; various modes of cooling, ranging from very fast to very slow cooling during crystallizations. Heating or melting the compounds followed by cooling gradually or immediately, one can also obtain polymorphs. The presence of polymorphs may be determined by solid probe NMR spectroscopy, IR spectroscopy, differential scanning calorimetry and powder X-ray diffraction or other such techniques.

The present invention also provides a pharmaceutical composition, containing one or more of the compounds of the general formula (I) as defined above, their derivatives, analogs, tautomeric forms, stereoisomers, polymorphs, hydrates, metabolites, prodrugs, pharmaceutically acceptable salts, and pharmaceutically acceptable solvates in combination with the usual pharmaceutically employed carriers, diluents and the like, useful for the treatment and/or prevention of cancer, cancer cachexia and inflammatory diseases including immunological diseases.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. The compositions may be prepared by processes known in the art. The amount of the active ingredient in the composition may be less than 70% by weight. Such compositions typically contain from 1 to 25%, preferably 1 to 15% by weight of active compound, the remainder of the composition being pharmaceutically acceptable carriers, diluents, excipients or solvents.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly, with intramuscular administration being preferred in humans.

The pharmaceutical compositions of the invention are effective in lowering IL-6 levels, through pSTAT3 inhibition, as shown by tests in in-vitro. The pharmaceutical compositions of the present invention are also effective in treating and/or preventing cancer, cancer cachexia and inflammatory diseases including immunological diseases. Generally, the effective dose for treating a particular condition in a patient may be readily determined and adjusted by the physician during treatment to alleviate the symptoms or indications of the condition or disease. Generally, a daily dose of active compound in the range of about 0.01 to 1000 mg/kg of body weight is appropriate for administration to obtain effective results. The daily dose may be administered in a single dose or divided into several doses. In some cases, depending upon the individual response, it may be necessary to deviate upwards or downwards from the initially prescribed daily dose. Typical pharmaceutical preparations normally contain from about 0.2 to about 500 mg of active compound of formula I and/or its pharmaceutically active salts or solvates per dose.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition. Thus compounds of the present invention can be used in the treatment of cancer as a monotherapy in those cancer cells, which have constitutively active STAT-3; or also in combination of these pSTAT3 inhibitors with other clinically relevant cytotoxic agents or non-cytotoxic signal transduction inhibitors.

The term "therapeutically effective amount" or "effective amount" refers to that amount of a compound or mixture of compounds of formula (I) that is sufficient to effect treatment, as defined below, when administered alone or in combination with other therapies to an animal in need of such treatment. More specifically, it is that amount that is sufficient to lower the cytokines such as IL-6, through pSTAT3 inhibition, and to treat inflammatory diseases including immunological diseases, cancer and cancer cachexia.

The term "animal" as used herein is meant to include all mammals, and in particular humans. Such animals are also referred to herein as subjects or patients in need of treatment. The therapeutically effective amount will vary depending upon the subject and disease condition being treated, the weight and age of the subject, the severity of the disease condition, the particular compound of formula (I) chosen, the dosing regimen to be followed, timing of administration, the manner of administration and the like, all of which can readily be determined by one of ordinary skill in the art.

The term "treatment" or "treating" means any treatment of a disease in a mammal, including:

a) Preventing the disease, that is, causing the clinical symptoms of the disease not to develop;

b) Inhibiting the disease, that is, slowing or arresting the development of clinical symptoms; and/or c) Relieving the disease, that is, causing the regression of clinical symptoms.

From the foregoing description, one skilled in the art can easily ascertain the essential characteristics of this invention, and without departing from the spirit and scope thereof, can make various changes and modifications of the invention to adapt it to various usages and conditions.

The present invention is provided by the examples given below, which are provided by the way of illustration only, and should not be considered to limit the scope of the invention. Variation and changes, which are obvious to one skilled in the art, are intended to be within the scope and nature of the invention, which are defined in the appended claims.

Anti-Cancer Experimental Methods

Anti-Cancer Screen

Experimental drugs are screened for anti-cancer activity in three cell lines for their $GI_{50}$, TGI and $LC_{50}$ values (using five concentrations for each compound). The cell lines are maintained in DMEM containing 10% fetal bovine serum. 96 well micro titer plates are inoculated with cells in 100 µL for 24 hours at 37° C., 5% CO2, 95% air and 100% relative humidity. 5000 HCT116 cells/well, 5000 NCIH460 cells/well and 5000 U251 cells/well are plated. A separate plate with these cell lines is also inoculated to determine cell viability before the addition of the compounds ($T_0$), (See Table I).

Addition of Experimental Drugs:

Following 24-hours incubation, experimental drugs are added to the 96 well plates. Each plate contains one of the above cell lines and the following in triplicate: five different concentrations (0.01, 0.1, 1, 10 and 100 µM) of four different compounds, appropriate dilutions of a cytotoxic standard and control (untreated) wells. Compounds are dissolved in DMSO to make 20 mM stock solutions on the day of drug addition and frozen at −20° C. Serial dilutions of these 20 mM stock solutions are made in complete growth medium such that 100 µL of these drug solutions in medium, of final concentrations equaling 0.01, 0.1, 1, 10 and 100 µM can be added to the cells in triplicate. Standard drugs whose anti-cancer activity has been well documented and which are regularly used are Doxorubicin and SAHA, (See Table I).

End-Point Measurement:

For $T_0$ measurement, 24 hours after seeding the cells, 10 µL of 3-(4,5-Dimethyl-2-thiazolyl)-2,5-diphenyl-2H-tetrazolium (MTT) solution per well is added and incubation carried out for 3 hours at 37° C., 5% $CO_2$, 95% air and 100% relative humidity, protected from light. Cells incubated with compounds for 48 hours are treated similarly except with the addition of 20 µL MTT solution per well and a subsequent incubation under the same conditions. After 3 hours of MTT incubation, well contents are aspirated carefully followed by addition of 150 µL DMSO per well. Plates are agitated to ensure solution of the formazan crystals in DMSO and absorbance read at 570 nm, (See Table I).

Calculation of $GI_{50}$, TGI and $LC_{50}$:

Percent growth is calculated for each compound's concentration relative to the control and zero measurement wells ($T_0$; viability right before compound addition). If a test well's O.D. value is greater than the $T_0$ measurement for that cell line % Growth=(test−zero)/(control−zero)×100

If a test well's O.D. value is lower than the $T_0$ measurement for that cell line, then % Growth=(test−zero)/zero×100

Plotting % growth versus experimental drug concentration, $GI_{50}$ is the concentration required to decrease % growth by 50%; TGI is the concentration required to decrease % growth by 100% and $LC_{50}$ is the concentration required to decrease % growth by 150%, (See Table I).

TABLE I

| Example No | NCIH460 | | | HCT116 | | | MDAMB-231/U 251 | | | Mean |
|---|---|---|---|---|---|---|---|---|---|---|
| | $GI_{50}$ | TGI | $LC_{50}$ | $GI_{50}$ | TGI | $LC_{50}$ | $GI_{50}$ | TGI | $LC_{50}$ | $GI_{50}$ |
| 1 | 0.78 | 18 | 62 | 8.5 | 39 | 79 | 5 | 9.8 | 60 | 4.8 |
| 3 | 27 | 54 | 80 | 7 | 36 | 72 | 55 | 77 | >100 | 29.7 |
| 4 | 18 | 47 | 80 | 32 | 57 | 82 | 34 | 59 | 84 | 28.0 |
| 6 | 10 | 42 | 75 | >100 | >100 | >100 | >100 | >100 | >100 | 10.5 |
| 8 | 15 | 45 | 75 | 5.8 | 22 | 90 | 5 | 50 | >100 | 8.6 |
| 15 | >100 | >100 | >100 | >100 | >100 | >100 | 8 | >100 | >100 | 8 |
| 19 | 7.5 | 35 | 70.5 | 27 | 52 | 79 | 51.5 | 67 | 85 | 28.67 |
| 23 | 0.79 | 35 | 70 | 18 | 47 | 77 | 1 | 10 | 65 | 6.6 |
| 24 | 0.76 | 53 | 67 | 8.3 | 53 | 80 | 18 | 51 | 79 | 9 |
| 25 | 0.67 | 55 | 68 | 5.6 | 48 | 79 | 13 | 49 | 81 | 6.4 |
| 26 | 2 | 22 | 70 | 30 | 48 | 68 | 30 | 85 | >100 | 20.7 |
| 27 | 45 | 98 | >100 | 30 | 60 | 90 | 2.8 | 48 | >100 | 25.93 |
| 30 | 30 | 60 | 90 | 25 | 72 | 84 | 2.5 | 9 | 70 | 19.17 |

TABLE I-continued

| Example No | NCIH460 | | | HCT116 | | | MDAMB-231/U 251 | | | Mean |
| | $GI_{50}$ | TGI | $LC_{50}$ | $GI_{50}$ | TGI | $LC_{50}$ | $GI_{50}$ | TGI | $LC_{50}$ | $GI_{50}$ |
| --- | --- | --- | --- | --- | --- | --- | --- | --- | --- | --- |
| 31 | 35 | 90 | 65 | 38 | 66 | 92 | 4 | 7 | 10 | 25.67 |
| 35 | 0.8 | 7.5 | 60 | 6 | 42 | 85 | 3 | >100 | >100 | 3.27 |
| 59 | 9.5 | >100 | >100 | >100 | >100 | >100 | 47 | >100 | >100 | 28.25 |
| 60 | 24 | 61 | 85 | 26 | 62 | 100 | >100 | >100 | >100 | 25.00 |
| 66 | 14 | 54 | 79 | 26 | 49 | 84 | 15 | 48 | 77 | 18.33 |
| 70 | 23 | 50 | 78 | 5 | 23 | 67 | 3.5 | 8.9 | 57 | 10.5 |

Protocol for Measuring IL-6 in Culture Supernatants

Human Lung Cancer cell line (NCIH 460) is used for IL-6 measurement. 5000 cells/well were seeded in a 96 well plate and incubated in $CO_2$ incubator at 37° C. for 24 hours. After 24 hours of incubation the medium from all wells were completed removed and added 100 µl of fresh DMEM containing 10% FCS. 100 µl of different concentrations of the drug were added and incubated for 5 hours in $CO_2$ incubator at 37° C. After 5 hours of incubation the supernatants were collected and stored at −80° C. The concentration of IL-6 in the supernatant was measured using ELISA kit and the $IC_{50}$ value of the compound was determined from the dose response curve, (See Table II).

TABLE II

| | IL-6 Inhibition (%) | | | |
| Example | 0.1 µM | 1 µM | 10 µM | $IC_{50}$ (µM) |
| --- | --- | --- | --- | --- |
| 1 | 45.71 | 55.29 | — | 5 |
| 23 | — | — | 29.28 | 24 |
| 24 | — | — | — | No activity |
| 25 | 35.96 | 50.87 | — | 0.78 |
| 35 | — | 45.03 | 80.42 | — |

Western Blot Analysis to Determine the Inhibition of pSTAT3 in Prostate (DU 145) and Ovarian Cancer (SKOV-3) Cell Lines Western blot analysis was performed as described by Kammer W et. al (J Biol Chem 271, 23634-23637, and J Biol Chem 273, 31222-31229). Briefly, 60 µg of whole cell extract was solubilized in Laemmeli buffer (50 mM Tris/HCl, pH 6.8, 2% SDS, 10% glycerol, 1 mM DTT, 1× Protease inhibitor cocktail, SET-3 (Calbiochem), 1 mM Sodium Ortho-vanadate) boiled for 5-10 minutes, and separated on a 10 or 12% acrylamide SDS gel. After protein transfer, the nitrocellulose membranes were blocked in blocking buffer for 2 hour (1×TBS, 0.1% Tween-20, 5% BSA). Membranes were incubated for 20 hours in blocking buffer containing, STAT3 P-Tyr705 (Santa Cruz Biotech), STAT3 (H-190, Santa Cruz Biotech) and Actin (C-2, Santa Cruz Biotech) antibody at 1:300 dilution. Detection was performed with HRP conjugated antimouse/antirabbit IgG (Santa Cruz Biotech) at a dilution of 1:3,000 for 1 hour. Visualization was performed using an Enhanced Chemiluminescence detection kit (Amersham). See Appended Diagrams: FIGS. 1 and 2.

Enzyme-Linked Immunosorbent Assay (ELISA) to Measure the Levels of pSTAT3 in HepG2 Cell Lines Assay was performed based on the protocol described by the manufacturer, as in the ELISA kit from R&D System (DuoSet IC, Cat. No: DYC1799-2). Briefly the assay was performed as such Plate Preparation/Assay Procedure:

Capture Antibody was diluted to a working concentration of 2.0 µg/mL in PBS. 100 µl/well of the antibody was used to coat using 96 well microplate; plate was sealed and incubated overnight at room temperature. After washing the plate wells with wash buffer, they were blocked using reagent diluent (300 µl) and incubated for 1-2 hours. The plates were made ready after 2-3 washes with wash buffer. Nuclear extracts from HepG2 cells were collected as per the manufacturers protocol. Volume was made to 30 µl using lysis buffer B after adding 3 µl of the biotin labeled ds oligonucleotide to 50 µg of the nuclear extract, in a sterile microfuge tube. Samples were then incubated at room temperature for about 30 minutes. 3 µl of unlabeled ds oligonucleotide was used for the determination of specificity by competition. 200 µl of the reagent diluent was added to each sample and mixed gently. From the above samples, 100 µl was added into each well, plate sealed and incubated for 2 hours at room temperature. After washing the plate with wash buffer, 100 µl of the Streptavidin-HRP antibody was added into each well and incubated at room temperature for 20 minutes in the dark. 100 µl of TMB substrate was used for detection after washing the plate 5 times with wash buffer. The reaction was stopped by adding 50 µl of stop solution to each well and the OD was determined using a microplate reader at 450 nm.

The results revealed that the examples 1 and 25 work through pSTAT3 inhibition (See Appended Diagrams: FIGS. 1 and 2).

Method for In-Vivo Anti-Cancer Activity Using Xenograft Model

Experiments were carried out using 6-8 week old female athymic SCID (Severe Combined Immune Deficient) mice. The mice were kept in laminar flow rooms (housed in Individually Ventilated Cages) at constant temperature and humidity. They had free access to food and water. Tumors were obtained form ATCC and maintained by s.c. passages of tumor fragments (about 2×2×2 mm) in healthy mice according to standard reported procedures. Each experimental group included six/eight mice bearing bilateral tumors. Tumors were implanted on day 0, and tumor growth was followed by biweekly measurements of tumor diameters with a Vernier caliper. Tumor Volume (TV) was calculated according to the following formula: TV $(mm^3) = d^2$ XD/2, where d and D are the shortest diameter and the longest diameter of the tumor, respectively. The drug treatment started when tumors were just measurable (Mean TV=150-200 $mm^3$).

All test compound/standard drugs were delivered by gavage in a volume of 10 ml/kg. Drugs were administered every day for single time to a period of 21 days. Control mice were treated with the drug solvent/vehicle. Tumor size is measured every alternate days and body weight is recorded daily. A post-drug treatment is also considered for 30 more days after withdrawal of dosing to demonstrate efficacy.

Test Compound Efficacy was Assessed by Various Parameters Like:
- a) Tumor Volume Inhibition (TVI): A TVI value higher than 80% is indicative of active compounds.
- b) T/C % is also another indicator for the activity. A reproducible 20% T/C is considered as therapeutically active.
- c) Log Cell Kill (LCK): A LCK value greater than 1 is indicative of active compounds.
- d) Relative Tumor Volume (RTV), Tumor Delay and % Tumor volume change are also considered as valuable additional parameters for assessment.
- e) Toxic effects of drug treatment were assessed by Body Weight Loss %
- f) Lethal toxicity was defined as any death in treated groups occurring before any control death. Mice were inspected daily for mortality and toxic clinical signs.

Results of the Xenograft Study:

The compound of example 1 showed good in-vivo anti-cancer activity, with IL-6 inhibition and the mechanism of action was through pSTAT3 inhibition. It showed 52% inhibition against NCI H460 Xenograft model. This encouraged us to further analog the compound of example 1 and we synthesized compounds of examples 24 and 25 and checked them for in-vivo anti-cancer activity using similar NCI H460 Xenograft model. (See Appended Diagrams: FIG. 3). These studies revealed that the compound of example 24 showed good anti-cancer activity; the compound of example 25 showed good anti-cancer activity, very good IL-6 inhibition, and also it operates through pSTAT3 inhibition; furthermore in the compounds of examples 24 and 25 no body weight loss was observed (See Appended Diagrams: FIG. 4).

We Claim:

1. A heterocyclic compound of the general formula (I)

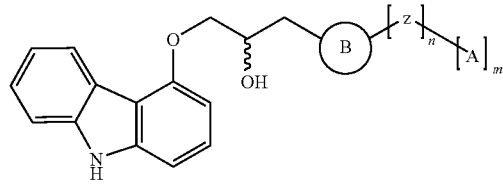
(I)

its tautomeric forms, stereoisomers, and their pharmaceutically acceptable salts;

wherein B represents a substituted or unsubstituted group selected from

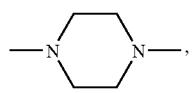
(I)

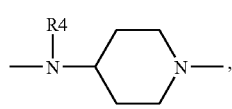
(II)

(III)

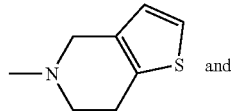
(IV)

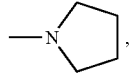
(V)

and $R_4$ represents hydrogen, an alkyl or benzyl, wherein Z represents —$CH_2$,

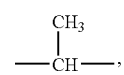

—C=O,

(I)

(II)

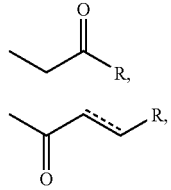
(III)

wherein - - - represents an optional bond,

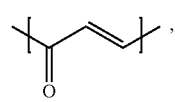
(IV)

and R represents $CH_2$, $CH_3$ or NH, wherein n is an integer from 0 to 1, wherein when B is formulae (I), (II), (IV) or (V), then A represents hydrogen, alkoxy groups selected from linear or branched ($C_1$-$C_4$) alkoxy groups; or substituted or unsubstituted groups selected from aryl groups, heteroaryl groups, heterocyclyl groups, and cycloalkyl groups, wherein when B is formula (III), then A represents substituted or unsubstituted groups selected from aryl groups, heteroaryl groups and cycloalkyl groups;

wherein m is an integer from 0 to 1, wherein when A includes a cyclic ring, A represents a substituted or unsubstituted 5 to 10 membered ring system, and the rings are monocyclic or bicyclic aromatic, optionally containing 1 to 4 hetero atoms selected from O, S and N, and the ring A is optionally substituted with halogens, hydroxy, nitro, cyano, azido, nitroso, amino, amidino, hydrazine, formyl, alkyl groups, aryl, cycloalkyl, alkoxy groups, aryloxy groups, aralkyl, aralkoxy, acyl, acyloxyacyl, carbalkoxy, carboxyalkyl, carboxamido, aminocarbonyl, carbonyl, alkylenedioxy, heterocyclyl, heteroaryl groups, heteroaralkyl, heteroaryloxy, heteroaralkoxy, monoalkylamino, dialkylamino, acylamino, alkoxycarbonyl, aryloxycarbonyl, alkylsulfonyl, arylsulfonyl, alkylsulfinyl, arylsulfinyl, alkylthio, arylthio, sulfanyl, sulfinyl, sulfonyl, sulfamoyl, thiol, alkoxyalkyl groups, or carboxylic acids and its derivatives, and wherein the substituents of A are optionally further substituted by groups comprising nitro or halogens, provided that when n is 0, A is other than aryl or cycloalkyl.

2. The heterocyclic compound of claim 1, selected from a group consisting of:

1-(9H-carbazol-4-yloxy)-3-[(2,4-dimethoxybenzyl)-amino]propan-2-ol;
1-(9H-carbazol-4-yloxy)-3-piperazin-1-ylpropan-2-ol;
1-(9H-carbazol-4-yloxy)-3-(6,7-dihydrothieno[3,2-c]pyridin-5(4H)-yl)propan-2-ol;
1-(9H-carbazol-4-yloxy)-3-[benzyl(methyl)amino]propan-2-ol;
1-(9H-carbazol-4-yloxy)-3-pyrrolidin-1-ylpropan-2-ol;
3-[(4-Benzylpiperazin-1-yl)]-1-(9H-carbazol-4-yloxy) propan-2-ol;
1-(9H-carbazol-4-yloxy)-3-{[(1R)-1-phenylethyl]amino}propan-2-ol;
1-(4-Acetylpiperazin-1-yl)-3-(9H-carbazol-4-yloxy)propan-2-ol;
t-Butyl 4-[2-hydroxy-3-(9H-carbazol-4-yloxy)propyl]piperazine-1-carboxylate;
3-[(1-Benzylpiperidin-4-yl)amino]-1-(9H-carbazol-4-yloxy)propan-2-ol;
1-(9H-carbazol-4-yloxy)-3-[(4,6-dimethylpyrimidin-2-yl)amino]propan-2-ol;
4-{[(3-(9H-carbazol-4-yloxy)-2-hydroxypropyl)amino]methyl}benzoic acid;
1-[4-(1,3-Benzodioxol-5-ylmethyl)piperazin-1-yl]-3-(9H-carbazol-4-yloxy)propan-2-ol;
1-[Benzyl-2,4-(dimethoxybenzyl)amino]-3-(9H-carbazol-4-yloxy)propan-2-ol;
1-(1H-Benzimidazol-2-ylamino)-3-(9H-carbazol-4-yloxy)propan-2-ol;
3-(9H-carbazol-4-yloxy)-1-[(5-mercapto-1,3,4-thiadiazol-2-yl)amino]propan-2-ol;
3-(9H-carbazol-4-yloxy)-1-{[5-(2-furyl)-1H-pyrazol-3-yl]amino}propan-2-ol;
3-(9H-carbazol-4-yloxy)-1-(2,1,3-benzothiadiazol-5-ylamino)propan-2-ol;
1-(9H-carbazol-4-yloxy)-3-benzylaminopropan-2-ol;
(2R)-1-(9H-carbazol-4-yloxy)-3-[(2,4-dimethoxy-benzyl)amino]propan-2-ol;
(2S)-1-(9H-carbazol-4-yloxy)-3-[(2,4-dimethoxy-benzyl)amino]propan-2-ol;
1-(9H-carbazol-4-yloxy)-3-{4-[(5-nitro-2-furyl)methyl]piperazin-1-yl}propan-2-ol;
1-(9H-carbazol-4-yloxy)-3-{4-[(5-nitro-2-thienyl)methyl]piperazin-1-yl}propan-2-ol;
1-(9H-carbazol-4-yloxy)-3-{4-[(thiazol-2-yl)methyl]piperazin-1-yl}propan-2-ol;
1-(9H-carbazol-4-yloxy)-3-[4-(cyclopropylmethyl)piperazin-1-yl]propan-2-ol;
1-(9H-carbazol-4-yloxy)-3-[4-(3,5-dimethoxybenzyl)piperazin-1-yl]propan-2-ol;
1-(9H-carbazol-4-yloxy)-3-[4-(3,4-difluorobenzyl)piperazin-1-yl]propan-2-ol
1-(9H-carbazol-4-yloxy)-3-[4-(4-bromo-2-fluorobenzyl)piperazin-1-yl]propan-2-ol
1-(9H-carbazol-4-yloxy)-3-[4-(4-methylthiobenzyl)piperazin-1-yl]propan-2-ol;
1-(9H-carbazol-4-yloxy)-3[4-(2,4,6-trimethoxybenzyl)piperazin-1-yl]propan-2-ol;
1-(9H-carbazol-4-yloxy)-3-{4-(5-nitro-2-furoyl)piperazin-1-yl}pro-pan-2-ol;
1-(9H-carbazol-4-yloxy)-3-[4-(5-nitro-1H-pyrazole-3-carbonyl) piperazin-1-yl]propan-2-ol;
1-(9H-carbazol-4-yloxy)-3-[4-(2-furoyl)piperazin-1-yl]propan-2-ol;
1-(9H-carbazol-4-yloxy)-3-[4-(1H-indole-2-carbonyl)piperazin-1-yl]propan-2-ol;
1-(9H-carbazol-4-yloxy)-3-[4-(thiophene-2-carbonyl)piperazin-1-yl]propan-2-ol;
1-(9H-carbazol-4-yloxy)-3-{4-[5-(4-nitrophenyl)-2-furoyl]piperazin-1-yl}propan-2-ol;
1-(9H-carbazol-4-yloxy)-3-[4-(pyrazine-2-carbonyl)piperazin-1-yl]propan-2-ol;
1-(9H-carbazol-4-yloxy)-3-[4-(3,4-dimethoxybenzoyl)piperazin-1-yl]propan-2-ol;
1-(9H-carbazol-4-yloxy)-3-{4-[(4-methoxyphenyacetyl]piperazin-1-yl}propan-2-ol;
1-(9H-carbazol-4-yloxy)-3-[4-(pentafluorophenyl)acetylpiperazin-1-yl]propan-2-ol;
1-(9H-carbazol-4-yloxy)-3-{4-[(2E)-3-(1,3-benzodioxol-5-ypacryloyl]piperazin-1-yl}propan-2-ol;
1-(9H-carbazol-4-yloxy)-3-[4-(quinoxaline-2-carbonyl)piperazin-1-yl]propan-2-ol;
1-(9H-carbazol-4-yloxy)-3-[4-(6-cyanonicotine-3-carbonyl)piperazin-1-yl]propan-2-ol;
1-(9H-carbazol-4-yloxy)-3-[4-(pyridin-3-ylacetyl)piperazin-1-yl]propan-2-ol;
1-(9H-carbazol-4-yloxy)-3-[4-(thiophen-3-ylacetyl)piperazin-1-yl]propan-2-ol;
1-(9H-carbazol-4-yloxy)-3-[4-(1,3-benzodioxol-5-ylearbonyl)piperazin-1-yl]propan-2-ol;
1-(9H-carbazol-4-yloxy)-3-{4-[3-(1H-indole-2-carbonyl)propanoyl]piperazin-1-yl}propan-2-ol;
1-(9H-carbazol-4-yloxy)-3-[4-(4-fluoro-1H-indole-2-carbonyl)piperazin-1-yl]propan-2-ol;
1-(9H-carbazol-4-yloxy)-3-[4-(3-fluoro-4-hydroxyphenyl)acetylpiperazin-1-yl]propan-2-ol;
3-[4-(1-Benzofuran-2-ylcarbonyl)piperazin-1-yl]-1-(9H-carbazol-4-yloxy)-propan-2-ol;
1-(9H-carbazol-4-yloxy)-3-[4-(4-fluorophenyl)acetylpiperazin-1-yl]propan-2-ol;
3-[4-(5-Bromothiophene-2-carbonyl)piperazin-1-yl]-1-(9H-carbazol-4-yloxy)propan-2-ol;
3-[4-(3-Aminopropanoyl)piperazin-1-yl]-1-(9H-carbazol-4-yloxy)propan-2-ol;
2-{4-[3-(9H-carbazol-4-yloxy)-2-hydroxypropyl]-piperazin-1-yl}-N-(5-methyl-1,3-thiazol-2-yl)ac etamide;
2-{4-[3-(9H-carbazol-4-yloxy)-2-hydroxypropyl]-piperazin-1-yl}-N-(4-methyl-1,3-benzothiazol-2-yl)acetamide;
2-{4-[3-(9H-carbazol-4-yloxy)-2-hydroxypropyl]-piperazin-1-yl}-N-(4-methyl-1,3-thiazol-2-yl)acetamide;
2-{4-[3-(9H-carbazol-4-yloxy)-2-hydroxypropyl]-piperazin-1-yl}-N-(4-methoxy-1,3-benzothiazol-2-yl)acetamide;
2-{4-[3-(9H-carbazol-4-yloxy)-2-hydroxypropyl]-piperazin-1-yl}-N-phenyl acetamide;
2-{4-[3-(9H-carbazol-4-yloxy)-2-hydroxypropyl]-piperazin-1-yl}-N-(2,4-dimethoxybenzyl) acetamide;
1-(9H-carbazol-4-yloxy)-3-{[1-(5-nitro-2-furoyl)piperidin-4-yl]amino}propan-2-ol;
1-(9H-carbazol-4-yloxy)-3-{[1-(1-methyl-1H-pyrrole-2-carbonyl)piperidin-4-yl]amino}propan-2-ol;

1-(9H-carbazol-4-yloxy)-3-{[1-(4-fluorophenyl)acetyl)
piperidin-4-yl]amino}propan-2-ol;
1-(9H-carbazol-4-yloxy)-3-{[1-(3,4-dimethoxybenzoyl)
piperidin-4-yl]amino}propan-2-ol;
3-{[1-(1,3-Benzodioxol-5-ylcarbonyl)piperidin-4-yl]
amino}-1-(9H-carbazol-4-yloxy) propan-2-ol;
1-(9H-carbazol-4-yloxy)-3-{[1-(pentafluorophenyl)
acetylpiperidin-4-yl]amino}propan-2-ol;
1-(9H-carbazol-4-yloxy)-3-{[1-(6-cyanonicotine-3-carbonyl)piperidin-4-yl]amino}propan-2-ol;
1-(9H-carbazol-4-yloxy)-3-{[1-(4-methoxyphenylacetyppiperidin-4-yl]amino}propan-2-ol;
N-[3-(9H-carbazol-4-yloxy)-2-hydroxypropyl]-3,4-dimethoxy-N-methylbenzamide;
1-(9H-carbazol-4-yloxy)-3-[3,5-dimethoxybenzyl(methyl)amino]propan-2-ol;
1-(9H-carbazol-4-yloxy)-3-[4-(3-trifluoromethylphenylsulfonyl)piperazin-1-yl]propan-2-ol and 3-[4-(4-Acetylphenylsulfonyl) piperazin-1-yl]-1-(9H-carbazol-4-yloxy)propan-2-ol.

3. The racemic compound of formula (I), wherein A is a 2,4-di-methoxy phenyl ring, m is 1, Z is —CH$_2$, n is 1, B is —NH, and pharmaceutically acceptable salts thereof

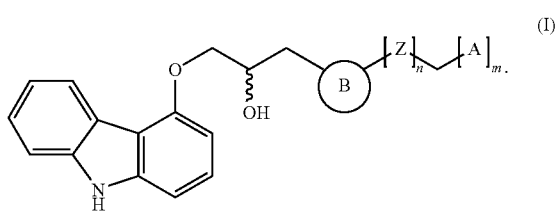

4. The compound of formula:

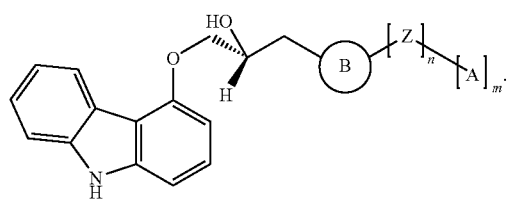

wherein A is a 2,4-di-methoxy phenyl ring, m is 1, Z is —CH$_2$, n is 1, B is —NH, the configuration at the chiral center is R, and pharmaceutically acceptable salts thereof.

5. The compound of formula:

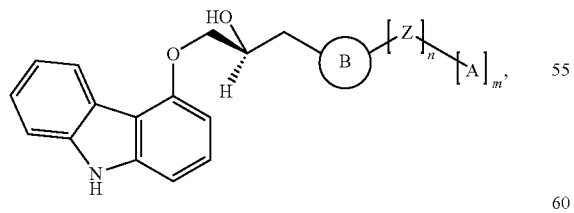

wherein A is a 2,4-di-methoxy phenyl ring, m is 1, Z is —CH$_2$, n is 1, B is —NH, the configuration at the chiral center is S, and pharmaceutically acceptable salts thereof.

6. A pharmaceutical composition comprising a compound of formula (I) according to claim 1 along with a pharmaceutically acceptable carrier, diluent, excipient or solvent.

7. The pharmaceutical composition according to claim 6, wherein the composition is in a form of a tablet, capsule, powder, syrup, solution, aerosol or suspension.

8. The pharmaceutical composition according to claim 6, wherein the amount of the compound of formula (I) in the composition is less than 70% by weight.

9. A method of lowering plasma concentrations of IL-6, comprising administering an effective amount of a compound according to claim 1, to a mammal in need thereof.

10. A method of treating inflammatory diseases selected from the group consisting of multiple myeloma, rheumatoid arthritis, psoriasis, and cachexia, mediated by IL-6, through pSTAT3 inhibition, comprising administering an effective amount of a compound according to claim 1 to a mammal in need thereof.

11. A method for the treatment of cancer as a monotherapy in cancer cells selected from the group consisting of lung cancer cells, prostate cancer cells, and ovarian cancer cells, which have constitutively active pSTAT3 comprising administering a compound according to claim 1 to a mammal in need of the treatment.

12. A method for the treatment of cancer in cancer cells selected from the group consisting of lung cancer cells, prostate cancer cells, and ovarian cancer cells, which have constitutively active pSTAT3 comprising administering a combination of a compound according to claim 1 with other clinically relevant cytotoxic agents or non-cytotoxic signal transduction inhibitors to a mammal in need of the treatment.

13. A heterocyclic compound of the general formula (I)

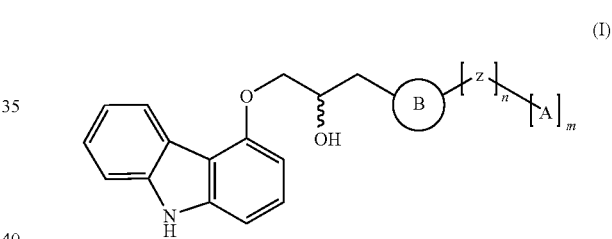

its tautomeric forms, stereoisomers, and their pharmaceutically acceptable salts;
wherein B represents a substituted or unsubstituted group selected from

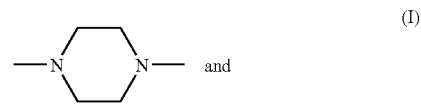

and R$_4$ represents hydrogen,
wherein Z represents —CH$_2$ or —C═O,
wherein n is 1,
wherein A represents substituted or unsubstituted aryl or furyl groups,
wherein m is 1,
and A is optionally substituted with halogens, hydroxy, nitro, cyano, azido, nitroso, amino, amidino, hydrazine, formyl, alkyl groups, aryl, cycloalkyl, alkoxy groups, aryloxy groups, aralkyl, aralkoxy, acyl, acyloxyacyl, carboalkoxy, carboxyalkyl, carboxamido, aminocarbonyl, carbonyl, alkylenedioxy, heterocyclyl, heteroaryl groups, heteroaralkyl, heteroaryloxy, heteroaralkoxy, monoalkylamino, dialkylamino, acylamino, alkoxycarbonyl, aryloxycarbonyl, alkylsulfonyl, arylsulfonyl, alkylsulfinyl, arylsulfinyl, alkylthio, arylthio, sulfanyl, sulfinyl, sulfonyl, sulfamoyl, thiol, alkoxyalkyl groups, or carboxylic acids and its derivatives, and wherein the substituents of A are optionally further substituted by groups comprising nitro or halogens.

14. The heterocyclic compound of claim 13, selected from a group consisting of:

1-(9H-carbazol-4-yloxy)-3-[(2,4-dimethoxybenzyl)-amino]propan-2-ol;

(2R)-1-(9H-carbazol-4-yloxy)-3-[(2,4-dimethoxy-benzy-pamino]propan-2-ol;

(2S)-1-(9H-carbazol-4-yloxy)-3-[(2,4-dimethoxy-benzy-pamino]propan-2-ol;

1-(9H-carbazol-4-yloxy)-3-{4-[(5-nitro-2-furypmethyl] piperazin-1-yl}propan-2-ol;

1-(9H-carbazol-4-yloxy)-3[4-(3,5-dimethoxybenzyl)piperazin-1-yl]propan-2-ol;

1-(9H-carbazol-4-yloxy)-3[4-(3,4-difluorobenzyl)piperazin-1-yl]propan-2-ol; and 1-(9H-carbazol-4-yloxy)-3-{4-(5-nitro-2-furoyl)piperazin-1-yl}propan-2-ol.

15. The heterocyclic compound of claim 1, wherein the compound is 1-(9H-carbazol-4-yloxy)-3-[(2,4-dimethoxy-benzyl)-amino]propan-2-ol.

16. The heterocyclic compound of claim 1, wherein the compound is (2R)-1-(9H-carbazol-4-yloxy)-3-[(2,4-dimethoxy-benzyl)amino]propan-2-ol.

17. The heterocyclic compound of claim 1, wherein the compound is (2S)-1-(9H-carbazol-4-yloxy)-3-[(2,4-dimethoxy-benzyl)amino]propan-2-ol.

18. The heterocyclic compound of claim 1, wherein the compound is 1-(9H-carbazol-4-yloxy)-3-{4-(5-nitro-2-furoyl)piperazin-1-yl}propan-2-ol.

* * * * *